(12) United States Patent
Chinnaiyan et al.

(10) Patent No.: US 11,013,754 B2
(45) Date of Patent: May 25, 2021

(54) COMPOSITIONS AND METHODS FOR TREATING CANCER

(71) Applicant: The Regents of the University of Michigan, Ann Arbor, MI (US)

(72) Inventors: Arul Chinnaiyan, Northville, MI (US); Rohit Malik, Pennington, NJ (US); Yajia Zhang, Ann Arbor, MI (US); Marcin Cieslik, Ann Arbor, MI (US); Sethuramasundaram Pitchiaya, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 69 days.

(21) Appl. No.: 16/378,825

(22) Filed: Apr. 9, 2019

(65) Prior Publication Data
US 2019/0307787 A1 Oct. 10, 2019

Related U.S. Application Data

(60) Provisional application No. 62/655,308, filed on Apr. 10, 2018.

(51) Int. Cl.
*A61K 31/7105* (2006.01)
*C12N 15/113* (2010.01)
*G01N 33/574* (2006.01)

(52) U.S. Cl.
CPC ........ *A61K 31/7105* (2013.01); *C12N 15/113* (2013.01); *G01N 33/57434* (2013.01); *C12N 2310/11* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 2014/0073525 A1 | 3/2014 | Chang et al. | |
| 2016/0160295 A1 | 6/2016 | Chinnaiyan et al. | |
| 2019/0153449 A1 | 5/2019 | Chinnaiyan et al. | |
| 2019/0307787 A1 | 10/2019 | Chinnaiyan et al. | |

FOREIGN PATENT DOCUMENTS

| | | | |
|---|---|---|---|
| WO | WO-2014187856 A1 * | 11/2014 | ........... C12N 15/113 |
| WO | WO 2014/205555 | 12/2014 | |
| WO | WO 2016/094420 | 6/2016 | |
| WO | WO 2017/007941 A1 | 1/2017 | |
| WO | WO 2018/006074 A2 | 1/2018 | |
| WO | WO 2019/103967 | 5/2019 | |
| WO | WO 2019/199733 | 10/2019 | |

OTHER PUBLICATIONS

Abate-Shen et al., "Molecular genetics of prostate cancer." Genes Dev. Oct. 1, 2000;14(19):2410-34.
Barretina et al. "The Cancer Cell Line Encyclopedia Enables Predictive Modelling of Anticancer Drug Sensitivity" Nature. Mar. 28, 2012;483(7391):603-7.
Bejerano et al., "Ultraconserved elements in the human genome." Science. May 28, 2004;304(5675):1321-5.
Bell et al. "Insulin-like Growth Factor 2 mRNA-binding Proteins (IGF2BPs): Post-Transcriptional Drivers of Cancer Progression?" Cell Mol Life Sci. Aug. 2013;70(15):2657-75.
Birney et al."Identification and Analysis of Functional Elements in 1% of the Human Genome by the ENCODE Pilot Project" Nature. Jun. 14, 2007;447(7146):799-816.
Bozgeyik et al., "OncoLncs: Long Non-Coding RNAs with Oncogenic Functions" Mol Biol 2016, 5:3, 1000162, p. 1-13.
Cabili et al., "Integrative annotation of human large intergenic noncoding RNAs reveals global properties and specific subclasses." Genes Dev. Sep. 15, 2011;25(18):1915-27.
Calin et al., "Ultraconserved Regions Encoding ncRNAs are Altered in Human Leukemias and Carcinomas" Cancer Cell. Sep. 2007;12(3):215-29.
Cancer Genome Atlas, "Comprehensive molecular portraits of human breast tumours."Nature. Oct. 4, 2012;490(7418):61-70.
Chen et al., "LIFR is a breast cancer metastasis suppressor upstream of the Hippo-YAP pathway and a prognostic marker." Nat Med. Oct. 2012;18(10):1511-7.
Cong et al., "Multiplex Genome Engineering Using CRISPR/Cas Systems" Science. Feb. 15, 2013;339(6121):819-23.
Consortium "The Genotype-Tissue Expression (GTEx) Project" Nat Genet. Jun. 2013;45(6):580-5.
Crea, Francesco et al. "Identification of a long non-coding RNA as a novel biomarker and potential therapeutic target for metastatic prostate cancer" Oncotarget, vol. 5, No. 3, Feb. 15, 2014, pages.
Curtis et al., "The genomic and transcriptomic architecture of 2,000 breast tumours reveals novel subgroups."Nature. Apr. 18, 2012;486(7403):346-52.
Derrien et al., "The Gencode v7 catalog of human long noncoding RNAs: analysis of their gene structure, evolution, and expression." Genome Res. Sep. 2012;22(9):1775-89.
Dimitrieva et al., "UCNEbase—a database of ultraconserved non-coding elements and genomic regulatory blocks." Nucleic Acids Res. Jan. 2013;41(Database issue):D101-9.
Dovey et al., "Oncogenic NRAS Cooperates With p53 Loss to Generate Melanoma in Zebrafish" Zebrafish. Dec. 2009;6(4):397-404.
El-Shewy et al., "The Insulin-Like Growth Factor Type 1 and Insulin-Like Growth Factor Type 2/mannose-6-phosphate Receptors Independently Regulate ERK1/2 Activity in HEK293 Cells" J Biol Chem. Sep. 7, 2007;282(36):26150-7.
Engreitz et al., "RNA-RNA Interactions Enable Specific Targeting of Noncoding RNAs to Nascent Pre-mRNAs and Chromatin Sites" Cell . Sep. 25, 2014;159(1):188-199.
EP Search Report, EP Patent Application No. 15867280.8, dated Jun. 19, 2018, 14 pages.

(Continued)

*Primary Examiner* — Tracy Vivlemore
(74) *Attorney, Agent, or Firm* — Casimir Jones, S.C.; Tanya A. Arenson

(57) ABSTRACT

Provided herein are compositions and methods for treating cancer. In particular, provided herein are compositions, methods, and uses of inhibitors of ARlnc1 for treating cancer.

9 Claims, 18 Drawing Sheets

Specification includes a Sequence Listing.

(56) References Cited

OTHER PUBLICATIONS

Epstein et al., "The pathological interpretation and significance of prostate needle biopsy findings: implications and current controversies." J Urol. Aug. 2001;166(2):402-10.
Etzioni et al., "Cancer surveillance series: interpreting trends in prostate cancer-part III: Quantifying the link between population prostate-specific antigen testing and recent declines in prostate cancer mortality." J Natl Cancer Inst. Jun. 16, 1999;91(12):1033-9.
Faghihi et al., "Expression of a Noncoding RNA is Elevated in Alzheimer's Disease and Drives Rapid Feed-Forward Regulation of Beta-Secretase" Nat Med. Jul. 2008;14(7):723-30.
Finn et al., "Pfam: the protein families database." Nucleic Acids Res. Jan. 2014;42(Database issue):D222-30.
GenBank Accession No. AL391244, retrieved Dec. 13, 2012, 16 pages.
Giraldez et al., "MicroRNAs Regulate Brain Morphogenesis in Zebrafish" Science. May 6, 2005;308(5723):833-8.
Gluck et al., "TP53 genomics predict higher clinical and pathologic tumor response in operable early-stage breast cancer treated with docetaxel-capecitabine ± trastuzumab." Breast Cancer Res Treat. Apr. 2012;132(3):781-91.
Gong et al., "lncRNAs Transactivate STAU1-mediated mRNA Decay by Duplexing With 3' UTRs via Alu Elements" Nature . Feb. 10, 20112;470(7333):284-8.
Grasso et al., "The mutational landscape of lethal castration-resistant prostate cancer." Nature. Jul. 12, 2012;487(7406):239-43.
Gupta et al., "Long Non-Coding RNA HOTAIR Reprograms Chromatin State to Promote Cancer Metastasis" Nature. Apr. 15, 2010;464(7291):1071-6.
Guttman et al., "Ab initio reconstruction of cell type-specific transcriptomes in mouse reveals the conserved multi-exonic structure of lincRNAs." Nat Biotechnol. May 2010;28(5):503-10.
Hafner et al., "Transcriptome-wide Identification of RNA-binding Protein and microRNA Target Sites by PAR-CLIP" Cell . Apr. 2, 2010;141(1):129-41.
Hämmerle et al., "Posttranscriptional Destabilization of the Liver-Specific Long Noncoding RNA HULC by the IGF2 mRNA-binding Protein 1 (IGF2BP1)" Hepatology. Nov. 2013;58(5):1703-12.
Hofmann et al., "Genome-wide analysis of cancer/testis gene expression." Proc Natl Acad Sci U S A. Dec. 23, 2008;105(51):20422-7. 6 pages.
Hosono et al., "Oncogenic Role of Thor, a Conserved Cancer/Testis Long Non-coding RNA" Cell. Dec. 14, 2017;171(7):1559-1572. e20.
Hudson et al., "Transcription Signatures Encoded by Ultraconserved Genomic Regions in Human Prostate Cancer" Mol Cancer. Feb. 14, 2013;12:13.
Hwang et al., "Efficient Genome Editing in Zebrafish Using a CRISPR-Cas System" Nat Biotechnol. Mar. 2013;31(3):227-9.
International Search Report dated mailed May 6, 2016, PCT/US2015/064525, Filed Dec. 8, 2015. 17 Pages.
International Search Report of related PCT/US2018/061802, dated mailed Feb. 19, 2019, 18 pages.
International Search Report of related PCT/US2019/026466, dated mailed Jul. 2, 2019, , 12 pages.
Iyer et al., "The Landscape of Long Noncoding RNAs in the Human Transcriptome" Nat Genet. Mar. 2015;47(3):199-208.
Jacobsen et al., "Incidence of prostate cancer diagnosis in the eras before and after serum prostate-specific antigen testing." JAMA. Nov. 8, 1995;274(18):1445-9.
Kauffmann et al., "High Expression of DNA Repair Pathways is Associated With Metastasis in Melanoma Patients" Oncogene. Jan. 24, 2008;27(5):565-73.
Kim et al., "Widespread Transcription at Neuronal Activity-Regulated Enhancers" Nature. May 13, 2010;465(7295):182-7.
Kretz et al., "Control of Somatic Tissue Differentiation by the Long Non-Coding RNA TINCR" Nature. Jan. 10, 2013;493(7431):231-5.
Kwan et al., "The Tol2kit: A Multisite Gateway-Based Construction Kit for Tol2 Transposon Transgenesis Constructs" Dev Dyn. Nov. 2007;236(11):3088-99.
Langenau et al., "Co-injection Strategies to Modify Radiation Sensitivity and Tumor Initiation in Transgenic Zebrafish" Oncogene. Jul. 10, 2008;27(30):4242-8.
Lee et al., "EBV Noncoding RNA Binds Nascent RNA to Drive Host PAXS to Viral DNA" Cell. Feb. 12, 2015;160(4):607-618.
Lennox et al., "Cellular Localization of Long Non-Coding RNAs Affects Silencing by RNAi More Than by Antisense Oligonucleotides" Nucleic Acids Res. Jan. 29, 2016;44(2):863-77.
Li et al., "A combined analysis of genome-wide association studies in breast cancer." Breast Cancer Res Treat. Apr. 2011;126(3):717-27.
Lieschke et al., "Animal Models of Human Disease: Zebrafish Swim Into View"Nat Rev Genet. May 2007;8(5):353-67.
Livingstone "IGF2 and Cancer" Endocr Relat Cancer. Oct. 24, 2013;20(6):R321-39.
Luke et al., "TERRA: Telomeric Repeat-Containing RNA" EMBO J. Sep. 2, 2009;28(17):2503-10.
Maattanen et al., "European randomized study of prostate cancer screening: first-year results of the Finnish trial." Br J Cancer. Mar. 1999;79(7-8):1210-4.
Malik et al., "The lncRNA PCAT29 Inhibits Oncogenic Phenotypes in Prostate Cancer" Mol Cancer Res. Aug. 2014;12(8):1081-7.
Mattick et al. "Non-coding RNA" Hum Mol Genet . Apr. 15, 2006;15 Spec No. 1:R17-29.
Mehra "A Novel RNA in Situ Hybridization Assay for the Long Noncoding RNA SChLAP1 Predicts Poor Clinical Outcome After Radical Prostatectomy in Clinically Localized Prostate Cancer" Neoplasia . Dec. 2014;16(12):1121-7.
Mehra "Discovery and Characterization of PRCAT47: A Novel Prostate Lineage and Cancer-Specific Long Noncoding RNA" annual reward of W81XWH-16-1-0314, Jul. 1, 2017,p. 1-27, retrieved May 27, 2019 from the internet: https://apps.dtic.mil/dtic/tr/fulltext/u2/1050260.pdf.
Mele et al., "Human Genomics. The Human Transcriptome Across Tissues and Individuals" Science. May 8, 2015;348(6235):660-5.
Michailidou et al., "Large-scale genotyping identifies 41 new loci associated with breast cancer risk."Nat Genet. Apr. 2013;45(4):353-61.
Necsulea et al., "The evolution of lncRNA repertoires and expression patterns in tetrapods."Nature. Jan. 30, 2014;505(7485):635-40.
Nelson et al., "A Peptide Encoded by a Transcript Annotated as Long Noncoding RNA Enhances SERCA Activity in Muscle" Science. Jan. 15, 2016;351(6270):271-5.
Nielsen et al., "A Family of Insulin-Like Growth Factor II mRNA-binding Proteins Represses Translation in Late Development" Mol Cell Biol. Feb. 1999;19(2):1262-70.
Niknafs et al., "The lncRNA Landscape of Breast Cancer Reveals a Role for Dscam-AS1 in Breast Cancer Progression" Nat Commun . Sep. 26, 2016;7:12791. 13 pages.
Pauli et al., "Toddler: An Embryonic Signal That Promotes Cell Movement via Apelin Receptors" Science . Feb. 14, 2014;343(6172):1248636.
Petrylak et al., "Docetaxel and Estramustine Compared With Mitoxantrone and Prednisone for Advanced Refractory Prostate Cancer" N Engl J Med. Oct. 7, 2004;351(15):1513-20.
Pickard, M.R. et al. "Long non-coding RNA GAS5 regulates apoptosis in prostate cancer cell lines" Biochimica et Biophysica Acta Molecular Basis of Disease, vol. 1832, No. 10, Oct. 1, 2013, pp. 1613-1623.
Prensner et al. "The Hong noncoding RNA SChLAP1 promotes aggressive prostate cancer and antagonizes the SWI/SNF complex" Nature Genetics, vol. 45, No. 11, Sep. 29, 2013, pp. 1392-1398.
Prensner et al., "The emergence of lncRNAs in cancer biology" Cancer Discov. Oct. 2011; 1(5): 391-407.
Prensner et al., "Transcriptome sequencing across a prostate cancer cohort identifies PCAT-1, an unannotated lincRNA implicated in disease progression." Nat Biotechnol. Jul. 31, 2011;29(8):742-9.
Qin et al., "Systematic Identification of Long Non-Coding RNAs With Cancer-Testis Expression Patterns in 14 Cancer Types" Oncotarget . Oct. 19, 2017;8(55):94769-94779.

(56) References Cited

OTHER PUBLICATIONS

Rhodes et al., "Oncomine 3.0: genes, pathways, and networks in a collection of 18,000 cancer gene expression profiles." Neoplasia. Feb. 2007;9(2):166-80.
Rinn et al., "Functional Demarcation of Active and Silent Chromatin Domains in Human HOX Loci by Noncoding RNAs" Cell . Jun. 29, 2007;129(7):1311-23.
Rinn et al., "Genome Regulation by Long Noncoding RNAs" Annu Rev Biochem. 2012;81:145-66.
Ruijter et al., "Molecular genetics and epidemiology of prostate carcinoma." Endocr Rev. Feb. 1999;20(1):22-45.
Sahu et al., "Long Noncoding RNAs in Cancer: From Function to Translation" Trends Cancer. Oct. 1, 2015;1(2):93-109.
Salmena et al., "A ceRNA Hypothesis: The Rosetta Stone of a Hidden RNA Language?" Cell. Aug. 5, 2011;146(3):353-8.
Sanchez-Rivera et al., "Applications of the CRISPR-Cas9 System in Cancer Biology" Nat Rev Cancer. Jul. 2015;15(7):387-95.
Sauvageau et al., "Multiple Knockout Mouse Models Reveal lincRNAs are Required for Life and Brain Development" Elife. Dec. 31, 2013;2:e01749.
Schroder et al., "Evaluation of the digital rectal examination as a screening test for prostate cancer. Rotterdam section of the European Randomized Study of Screening for Prostate Cancer." J Natl Cancer Inst. Dec. 2, 1998;90(23):1817-23.
Shukla et al., "Identification and Validation of PCAT14 as Prognostic Biomarker in Prostate Cancer" Neoplasia. Aug. 2016;18(8):489-99.
Simpson et al. "Cancer/testis Antigens, Gametogenesis and Cancer"Nat Rev Cancer. Aug. 2005;5(8):615-25.
St. Laurent et al., "The Landscape of Long Noncoding RNA Classification" Trends Genet. May 2015;31(5):239-51.
Stacey et al., "Common variants on chromosomes 2q35 and 16q12 confer susceptibility to estrogen receptor-positive breast cancer." Nat Genet. Jul. 2007;39(7):865-9.
Steijger et al., "Assessment of transcript reconstruction methods for RNA-seq." Nat Methods. Dec. 2013;10(12):1177-84.
Subramanian et al., "Gene Set Enrichment Analysis: A Knowledge-Based Approach for Interpreting Genome-Wide Expression Profiles"Proc Natl Acad Sci U S A. Oct. 25, 2005;102(43):15545-50.
Takayama et al., "Androgen-responsive Long Noncoding RNA CTBP1-AS Promotes Prostate Cancer" EMBO J. Jun. 12, 2013;32(12):1665-80.
Tapparel et al., "The TPTE Gene Family: Cellular Expression, Subcellular Localization and Alternative Splicing" Gene. Dec. 24, 2003;323:189-99.
Taylor et al., "Integrative genomic profiling of human prostate cancer." Cancer Cell. Jul. 13, 2010;18(1):11-22.
Thomas et al., "multistage genome-wide association study in breast cancer identifies two new risk alleles at 1p11.2 and 14q24.1 (RAD51L1)." Nat Genet. May 2009;41(5):579-84.
Turnbull et al., "Genome-wide association study identifies five new breast cancer susceptibility loci." Nat Genet. Jun. 2010;42(6):504-7.
Ulitsky et al., "Conserved Function of lincRNAs in Vertebrate Embryonic Development Despite Rapid Sequence Evolution" Cell. Dec. 23, 2011;147(7):1537-50.
Ulitsky et al., "lincRNAs: Genomics, Evolution, and Mechanisms" Cell. Jul. 3, 2013;154(1):26-46.
Wang et al., "A Long Noncoding RNA Maintains Active Chromatin to Coordinate Homeotic Gene Expression" Nature . Apr. 7, 2011;472(7341):120-4.
Wang et al., "CPAT: Coding-Potential Assessment Tool using an alignment-free logistic regression model." Nucleic Acids Res. Apr. 1, 2013;41(6):e74.
Wang et al., "Molecular Mechanisms of Long Noncoding RNAs" Mol Cell. Sep. 16, 2011;43(6):904-14.
Weidensdorfer et al., "Control of C-Myc mRNA Stability by IGF2BP1-associated Cytoplasmic RNPs" RNA. Jan. 2009;15(1):104-15.
Welter et al., "The NHGRI GWAS Catalog, a curated resource of SNP-trait associations." Nucleic Acids Res. Jan. 2014;42(Database issue):D1001-6.
Winnepenninckx et al. "Gene Expression Profiling of Primary Cutaneous Melanoma and Clinical Outcome" J Natl Cancer Inst. Apr. 5, 2006;98(7):472-82.
Wright et al., "CopraRNA and IntaRNA: Predicting Small RNA Targets, Networks and Interaction Domains" Nucleic Acids Res . Jul. 2014;42(Web Server issue):W119-23.
Wutz et al., "Chromosomal Silencing and Localization Are Mediated by Different Domains of Xist RNA" Nat Genet. Feb. 2002;30(2):167-74.
Yu et al., "Gene expression alterations in prostate cancer predicting tumor aggression and preceding development of malignancy." J Clin Oncol. Jul. 15, 2004;22(14):2790-9.
Zhang et al., "Analysis of the Androgen Receptor-Regulated lncRNA Landscape Identifies a Role for ARLNC1 in Prostate Cancer Progression" Nat Genet. Jun. 2018;50(6):814-824.
Zhou Du et al. "Integrative genomic analyses reveal clinically relevant long noncoding RNAs in human cancer" Nature Structural & Molecular Biology, vol. 20, No. 7, Jun. 2, 2013, pp. 908-913.

\* cited by examiner

SEQUENCE LISTING

```
<160> NUMBER OF SEQ ID NOS: 307

<210> SEQ ID NO 1
<211> LENGTH: 54
<212> TYPE: DNA
<213> ORGANISM: Artificial Sequence
<220> FEATURE:
<223> OTHER INFORMATION: Synthetic

<400> SEQUENCE: 1
gatcactaat acgactcact atagggagag gagaccctca tttccttcca gctt            54

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
aagagccatg gaaccagcac ctgaa                                           25

<210> SEQ ID NO 3
<211> LENGTH: 25
<212> TYPE: DNA
<213> ORGANISM: Artificial Sequence
```

```
<220> FEATURE:
<223> OTHER INFORMATION: Synthetic

<400> SEQUENCE: 3
gggaacgagt tccagtggac aaggt                                    25

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ggctcttcct gagccgaaaa taagg                                    25

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
ctcgttccca tctaccctcc actct                                    25

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
ccatcaccat cttccaggag cga                                      23

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggtggtgaag acgccagtgg a                                        21

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
caccattggc aatgagcggt tc                                       22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
aggtctttgc ggatgtccac gt                                       22
```

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
acggctcaga tagcatacaa gag                                          23

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
gttacgagca gtgatgccta cc                                           22

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
cagtggatgg gctgaaaaat                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ggagcttggt gagctggtag                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ccttgtccac tggaactcgt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tataaccttg ggggccatga                                              20

<210> SEQ ID NO 16
<211> LENGTH: 25
<212> TYPE: DNA
<213> ORGANISM: Artificial Sequence
<220> FEATURE:
<223> OTHER INFORMATION: Synthetic

```
<400> SEQUENCE: 16
caggagtgta cgggaatgtg atggt                                           25

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
gattagccgt ctgccctcat ttgt                                            24

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gctcgtctca gagaagctgg                                                 20

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
gctcagatcc tgcaggtaca a                                               21

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
ggctctggac aggtggtaaa ga                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21
cggtaatgca ccaccttggt gt                                              22

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
acgctggaca gggggcaaaa g                                               21

<210> SEQ ID NO 23
```

<211> LENGTH: 21
<212> TYPE: DNA
<213> ORGANISM: Artificial Sequence
<220> FEATURE:
<223> OTHER INFORMATION: Synthetic

<400> SEQUENCE: 23
gggcagggca catggttcac t                                         21

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
gcgaaggaga agaccacgac at                                        22

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
taggcttccc tgcctctcca aa                                        22

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
tcgtgggcga ggggctgta                                            19

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27
catccgaacg ccttcatcat agtgt                                     25

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
gcaagaaggc ttcctggctc at                                        22

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
ccttcccgat acattcctgg ct                                              22

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
aaaattttac atgccctgta atgga                                           25

<210> SEQ ID NO 31
<211> LENGTH: 24
<212> TYPE: DNA
<213> ORGANISM: Artificial Sequence
<220> FEATURE:
<223> OTHER INFORMATION: Synthetic

<400> SEQUENCE: 31
tctgtatgga aaggatggt agca                                             24

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
cagtccctac tgagtactct ttctctc                                         27

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
cacagtgaaa tgtgtaatcc ttgc                                            24

<210> SEQ ID NO 34
<211> LENGTH: 22
<212> TYPE: DNA
<213> ORGANISM: Artificial Sequence
<220> FEATURE:
<223> OTHER INFORMATION: Synthetic

<400> SEQUENCE: 34
tcacagtgct gccgagtgtc ta                                              22

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
ccataggttg atggctggtt tcc                                             23

<210> SEQ ID NO 36
<211> LENGTH: 22
<212> TYPE: DNA

```
<213> ORGANISM: Artificial Sequence
<220> FEATURE:
<223> OTHER INFORMATION: Synthetic

<400> SEQUENCE: 36
gaggaggtga aagaccagag ca                                              22

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
tagcatctcg gctggacttc ga                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
gcaatactcg ccttacggct ct                                              22

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
gggtctggaa tacacacctt gg                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
cgctatgtca cctcctgttt gc                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
actctgagga cgagaagccc tt                                              22

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
gacctctgtc ttacttgtgg agc                                             23
```

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
cgtcagatgg tgccagcaat ag                                    22

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
ctcttctgga acctctataa agc                                   23

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
catttccaga tgatcctgca gcaa                                  24

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
ttcccattgt ggctcctatc                                       20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gtggctggca cagagtagtg                                       20

<210> SEQ ID NO 48
<211> LENGTH: 55
<212> TYPE: DNA
<213> ORGANISM: Artificial Sequence
<220> FEATURE:
<223> OTHER INFORMATION: Synthetic

<400> SEQUENCE: 48
gatcactaat acgactcact atagggagag gagaagcatt ggaaaccta tttcc    55

<210> SEQ ID NO 49
<211> LENGTH: 29
<212> TYPE: DNA
<213> ORGANISM: Artificial Sequence
<220> FEATURE:

<223> OTHER INFORMATION: Synthetic

<400> SEQUENCE: 49
gaactcgagg ccaagttttg gctgaagag                                29

<210> SEQ ID NO 50
<211> LENGTH: 22
<212> TYPE: DNA
<213> ORGANISM: Artificial Sequence
<220> FEATURE:
<223> OTHER INFORMATION: Synthetic

<400> SEQUENCE: 50
gagttcatgg gtggcaaagt at                                       22

<210> SEQ ID NO 51
<211> LENGTH: 57
<212> TYPE: DNA
<213> ORGANISM: Artificial Sequence
<220> FEATURE:
<223> OTHER INFORMATION: Synthetic

<400> SEQUENCE: 51
gatcactaat acgactcact atagggagag gagagtcgtt ttacaacgtc gtgactg    57

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
gtacggggta tacatgtctg aca                                      23

<210> SEQ ID NO 53
<211> LENGTH: 60
<212> TYPE: DNA
<213> ORGANISM: Artificial Sequence
<220> FEATURE:
<223> OTHER INFORMATION: Synthetic

<400> SEQUENCE: 53
gatcactaat acgactcact atagggagag gagaaaaagt actgtagcct tcagtaattc    60

<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
ttggcacaga agcagtacac ac                                       22

<210> SEQ ID NO 55
<211> LENGTH: 26
<212> TYPE: DNA
<213> ORGANISM: Artificial Sequence
<220> FEATURE:
<223> OTHER INFORMATION: Synthetic

<400> SEQUENCE: 55
aaaagtactg tagccttcag taattc                                   26

```
<210> SEQ ID NO 56
<211> LENGTH: 56
<212> TYPE: DNA
<213> ORGANISM: Artificial Sequence
<220> FEATURE:
<223> OTHER INFORMATION: Synthetic

<400> SEQUENCE: 56
gatcactaat acgactcact atagggagag gagattggca cagaagcagt acacac      56

<210> SEQ ID NO 57
<211> LENGTH: 30
<212> TYPE: DNA
<213> ORGANISM: Artificial Sequence
<220> FEATURE:
<223> OTHER INFORMATION: Synthetic

<400> SEQUENCE: 57
gaaatagtgc ctttgtgtat attctgccta                                   30

<210> SEQ ID NO 58
<211> LENGTH: 30
<212> TYPE: DNA
<213> ORGANISM: Artificial Sequence
<220> FEATURE:
<223> OTHER INFORMATION: Synthetic

<400> SEQUENCE: 58
taggcagaat atacacaaag gcactatttc                                   30

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
caaaggcact atttccagat                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
gaacacagat tcaccttttc                                              20

<210> SEQ ID NO 61
<211> LENGTH: 54
<212> TYPE: DNA
<213> ORGANISM: Artificial Sequence
<220> FEATURE:
<223> OTHER INFORMATION: Synthetic

<400> SEQUENCE: 61
gatcactaat acgactcact atagggagag gagatgtata ttctgcctaa ggca        54

<210> SEQ ID NO 62
<211> LENGTH: 54
<212> TYPE: DNA
<213> ORGANISM: Artificial Sequence
<220> FEATURE:
<223> OTHER INFORMATION: Synthetic
```

<400> SEQUENCE: 62
gatcactaat acgactcact atagggagag gagacggata taagttaggt aaaa      54

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
ttaactctgg tctccccaac a      21

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gagattaaag ctgaatttgc tggt      24

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tgttgcaatg tcaccacctt      20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
agcaggtaaa gcgacaggaa      20

<210> SEQ ID NO 67
<211> LENGTH: 25
<212> TYPE: DNA
<213> ORGANISM: Artificial Sequence
<220> FEATURE:
<223> OTHER INFORMATION: Synthetic

<400> SEQUENCE: 67
gcctggatct gagagagata tcatc      25

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
acaccttttt ttttctggat tgttg      25

<210> SEQ ID NO 69
<211> LENGTH: 19

```
<212> TYPE: RNA
<213> ORGANISM: Artificial Sequence
<220> FEATURE:
<223> OTHER INFORMATION: Synthetic

<400> SEQUENCE: 69
gcaguaagug gaagaguuc                                                  19

<210> SEQ ID NO 70
<211> LENGTH: 19
<212> TYPE: RNA
<213> ORGANISM: Artificial Sequence
<220> FEATURE:
<223> OTHER INFORMATION: Synthetic

<400> SEQUENCE: 70
gcaguaagug gaagaguuc                                                  19

<210> SEQ ID NO 71
<211> LENGTH: 19
<212> TYPE: RNA
<213> ORGANISM: Artificial Sequence
<220> FEATURE:
<223> OTHER INFORMATION: Synthetic

<400> SEQUENCE: 71
cuuccugagc cgaaaauaa                                                  19

<210> SEQ ID NO 72
<211> LENGTH: 19
<212> TYPE: RNA
<213> ORGANISM: Artificial Sequence
<220> FEATURE:
<223> OTHER INFORMATION: Synthetic

<400> SEQUENCE: 72
aggaaacucc auagaccuu                                                  19

<210> SEQ ID NO 73
<211> LENGTH: 2786
<212> TYPE: DNA
<213> ORGANISM: Artificial Sequence
<220> FEATURE:
<223> OTHER INFORMATION: Synthetic

<400> SEQUENCE: 73
aaaagtactg tagccttcag taattctttc catgagtatt tgctcgtgct atttttttt       60 cagtctttat ttttcccaaa ttatccttcc cctctcttaa tttgaatgaa tagaaggttc     120
tagatttatg ggttttttttt ttttaatct ttttctttt tgagacagac tctcactctc      180
gggctggagt gcagcggcat gatctcggct cactgcaacc tctgcctccc gggttcatgt     240
aattctcatg cctcagcctc ccaagtagct gggattacag gcacacgcca ccatgcctgg     300
ctgatttaag attattttt tcacaaaact ttgaagacat atcttcttat cttctggctt      360
ctgttgttgt tcatttacag gttttcaggt gctggttcca tggctcttcc tgagccgaaa    420
ataaggaaac tccatagacc ttgtccactg gaactcgttc ccatctaccc tccactctat    480
ccagccccat gaggacaagg aacatgattg gttttgctca ctgccgtatc ttccgtacct    540
agtacgtaac aggacatcaa taaatattag ttgaatggaa gattaaatca acaaaatggg    600
tgatggatct ctgcagtaag tggaagagtt cttcatggcc cccaaggtta tatccatcta   660
gaacttcagc acgtaatttc atctggaaat agtgcctttg cggatataag ttaggtaaaa   720
```

```
ctgaagatga gatcatactg gattaggatg ggatctaaat ccaatgaaaa tgtcttcata    780
aaaaacagga agaacccat agaaacacaa ggaagaaggt catgtgaaga tggaggcaga     840
gattggaggg atgcagccac cggcccagga atgccagcag ccacccagaa gctggaagga    900
aatgagggat tctctcctag aacctttaga gagaacatgg tcctgtgaac agcttgattt    960
tggacttgcc catagcttgt atactcttac tttggataca attttatcca aacttggcta   1020
aacagtttct cagcctatgg aaaatttaaa atggagaaga ttcaactcga ttcttacaga   1080
ttcaaagcaa gaaaatgatg ggaacatagg aggagaccaa gaaagcctat aaaaagcaaa   1140
aatatgaagt gaacattgtg gtagctttaa gatgtttagt gtagctgcag gcacccatata  1200
cacatgaaaa cccccaaggg gaatccccat atcacagtgt agtgtgatat ttgacattcg   1260
tgatcatcta gagatgtaca gaaaaggtga atctgtgttc tgtatattct gcctaaggca   1320
aagaaatgtt tagctctctt taaaatagtt ccataatttt ttctaaaaag ctttgcttga   1380
aaactgtaag cttcccatat ctggagcatt tcactttaaa tatttggata aatatgttat   1440
cttcttactt ggacatttca tgtgtttagg gattgtcttc taaattcttc ctaattcata   1500
tagctgctaa cacttcccgc agagctaaac cattacagat atgaaataaa gacctattga   1560
tttgacttac ttttacttgt aaaaccttct gagtgttata acctcattta atctttcagc   1620
atttacagtt tcaagagttt tgtcacaat tagaagaatt cagctgcacc tccaagtgac    1680
agcagttgct ctggttggtg ggtgatctca ggaggcttga gaattgcttt gtctgtgagg   1740
gaagtaagac attttcagag ccccactta aaggtgtga actggctaga taatgaaccc     1800
cagggctaac gctgctatag cagtgggaag gaggtgatgg gttttcagtt tggacctcaa   1860
acatcaatac cctcctggta cggggaggaa cagagtccct cctttacttc tccattagaa   1920
agaatgagat ggcaagacaa tgaaacaggc aaagtgaaca gagatgcaag acaaaattca   1980
ggtgagagag ccagagcatc actcagccat tcctgacatg taaaacaggc aactagaaat   2040
ttgcagaaag gaagcgaagt ctccataaag atgtttttaa agtgagcttg aagtatttgg   2100
agacaattca gtgttacata aaatctgcaa atctctggat aaagaagcag agatcccagc   2160
atgggacaaa tggagcctca aaagtgggaa gaagacagag aagaccaggg cagaatgcat   2220
ctcttccttt ctcttggctt tcctggataa ggactgcatc attcctgtgg aaggacaggc   2280
catcagctcc gaaacactgt atgtattttc cagtatatac tgctagctgt gtgatgttgg   2340
gaaaatttgt taccctgtct aaccccact tccctcatct gtaaaatgga ataatgata    2400
gtacctacct atctcatagg tggcaactac aaggggcagc acactcaggg aattaaggaa   2460
gtttcagtga acatcaactt tatgaacaca gtgttcataa aggcaggtca gtgcagtggt   2520
ttgggagcca ggagaagcac gtgggccgga gtgtgcctgc aggagacaag gtcagagatg   2580
ttgctaataa tggagaataa aggatgcatt ctcattactg accttggagt cgttcattca   2640
ttcccagaat gtgttttgtc agcttactaa aacactaagt taaataatcc caggttttgt   2700
ttattataga tactaggact tagtggaccc aaggttaatg acatccagag tagacaaaca   2760
tcaagtgtgt actgcttctg tgccaa                                        2786
```

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74

-continued

```
ctagaacctt ctattcattc                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
gaacaacaac agaagccaga                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
catggaacca gcacctgaaa                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
tggagtttcc ttattttcgg                                               20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gaacgagttc cagtggacaa                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
taaccttggg ggccatgaag                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
gtgctgaagt tctagatgga                                               20

<210> SEQ ID NO 81
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 81
agcagctata tgaattagga                                                 20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
gtttagctct gcgggaagtg                                                 20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
ggtctttatt tcatatctgt                                                 20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
caaccagagc aactgctgtc                                                 20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
atgtcttact tccctcacag                                                 20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
cttctaaagt ggggctctga                                                 20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
tcattatcta gccagttcac                                                 20
```

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
cactgctata gcagcgttag                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
aactgaaaac ccatcacctc                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
gggtattgat gtttgaggtc                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
taaaggaggg actctgttcc                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tgccatctca ttctttctaa                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
tcactttgcc tgtttcattg                                               20

<210> SEQ ID NO 94
<211> LENGTH: 20
<212> TYPE: DNA
<213> ORGANISM: Artificial Sequence
<220> FEATURE:

<223> OTHER INFORMATION: Synthetic

<400> SEQUENCE: 94
tcaggaatgg ctgagtgatg                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
ttctagttgc ctgttttaca                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
gtctccaaat acttcaagct                                               20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
caggaatgat gcagtcctta                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
tacatacagt gtttcggagc                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
aacttcctta attccctgag                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
gcctttatga acactgtgtt                                               20

```
<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
aacatctctg accttgtctc                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
catcctttat tctccattat                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
tgtttgtcta ctctggatgt                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
gcacagaagc agtacacact                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
aaagctcctc ggtaggtctt                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
cacgctctgg aacagattct                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic
```

<400> SEQUENCE: 107
tgaaggttgc tgttcctcat                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
cagcagggac aacgtggatg                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
tgcttaagcc ggggaaagtg                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
aggatgtctt taaggtcagc                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
aagtgccccc taagtaattg                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
ttggcgttgt cagaaatggt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
cgacactgcc ttacacaact                                               20

<210> SEQ ID NO 114
<211> LENGTH: 20

-continued

<212> TYPE: DNA
<213> ORGANISM: Artificial Sequence
<220> FEATURE:
<223> OTHER INFORMATION: Synthetic

<400> SEQUENCE: 114
aaaagtgggg cgtacatgca                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
caatggggca caaggagtgg                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
agcagagaac ctttgcattc                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
cagtatcttc agtgctcttg                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
cccttgaaag gggaatactc                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
ttctagccct ttggtgtaac                                              20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
tagacggcag ttcaagtgtc                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
ccggacttgt agagagacag                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
gtagtcgcga ctctggtacg                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
ccagagccag tggaaagttg                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
ttgatgcgag cgtggggatg                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
aagagagtgt gccaggatga                                               20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
catacaactg gccttcttcg                                               20

<210> SEQ ID NO 127
<211> LENGTH: 20
<212> TYPE: DNA
<213> ORGANISM: Artificial Sequence

```
<220> FEATURE:
<223> OTHER INFORMATION: Synthetic

<400> SEQUENCE: 127
acacatcagg tgcggtgaag                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
gactgggata gggcactctg                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
ccatttcgct tttgacacaa                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
taaggtccgg agtagctatc                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
caatgggcaa aacatggtcc                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
cttctggggt ggaaagtaat                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
catctccaca gatcaggcag                                              20
```

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
tccatagtga cacccagaag                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
tcagcggctc ttttgaagaa                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
caagtttctt cagcttccgg                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
tcctcctgta gtttcagatt                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
tgtgacactg tcagcttctg                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ctgacattca tagccttcaa                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic

```
<400> SEQUENCE: 140
gcttccagga cattcagaaa                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
acacactaca cctggctcaa                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
caaggctgca aaggagtcgg                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ccagttcatt gaggctagag                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
cacttgacca cgtgtacaag                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
cacgtgtaag ttgcggaagc                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
aggagtactg aatgacagcc                                              20

<210> SEQ ID NO 147
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 147
catggcaaac accatgagcc                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
cattggtgaa ggatcgccag                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
aagtagagca tcctggagtt                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
attgaaaacc agatcagggg                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
ctgtacatcc gggacttgtg                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
ttgagagagg tgcctcattc                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
```
tgatttggag ccatccaaac                                                    20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tcatgcacag gaattcctgg                                                    20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
atgctgaaga gtagcagtgc                                                    20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
tttttgattt ttcagcccat                                                    20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
ccttgatgta gttcattcga                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
gcatgcaatg atacgatcga                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
agcaggatgt gggattttttt                                                   20

<210> SEQ ID NO 160
<211> LENGTH: 20
<212> TYPE: DNA

```
<213> ORGANISM: Artificial Sequence
<220> FEATURE:
<223> OTHER INFORMATION: Synthetic

<400> SEQUENCE: 160
ttggtgagct ggtagaagcg                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
aagtgaactg atgcagctct                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
ccatgtgtga cttgattagc                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
atcatttccg gaaagtccac                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
cttgcacaga gatgatctct                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
tttcccagaa aggatcttgg                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
ggtgtggaaa tagatgggct                                               20
```

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
gcctatgcag atatccaata                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
aagggtacag atgctttctc                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
gacctgtggg aattcataca                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
agaggttcct ttcttcatta                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
taggtagctc tttgtactca                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
gctatgcatc ttatatcctt                                               20

<210> SEQ ID NO 173
<211> LENGTH: 20
<212> TYPE: DNA
<213> ORGANISM: Artificial Sequence
<220> FEATURE:

<223> OTHER INFORMATION: Synthetic

<400> SEQUENCE: 173
tctttaattg ctcaggttcc                                           20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
caagtgccag ttaagtgtga                                           20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
ggccttatta agatgggatc                                           20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
cttatccatt ggtgtttctg                                           20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
cacttagagg cacatgggaa                                           20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
ttaaagtcca gttaggttcc                                           20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
tttctcttct cacttctagt                                           20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
ttatcttggg aggttccaat                                                    20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
tcctgagccg aaaataagga                                                    20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
catggtctta tgtatctgcg                                                    20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
caaaggcgtt ggtgatgttg                                                    20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
gtctttgtcg acttccaatg                                                    20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
gcttcaatga ttcctctcaa                                                    20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
atggtcaaca ttgcgttctt                                               20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cacccactta tcaagttttt                                               20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
tttggatttt tgctgagctc                                               20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
ggttattgtt gttgcgtaga                                               20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
cccaaatcca cttttcattg                                               20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
attgctggtt gccatatata                                               20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
gctcattgat ttgttgagca                                               20

<210> SEQ ID NO 193
<211> LENGTH: 20

-continued

<212> TYPE: DNA
<213> ORGANISM: Artificial Sequence
<220> FEATURE:
<223> OTHER INFORMATION: Synthetic

<400> SEQUENCE: 193 aactttttgaa gcgctgcttg                                                    20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
aactatgtag cccaatttgt                                                     20

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
ttggaaagcg tgttctgcat                                                     20

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
gtgcgtcagg attcgacaaa                                                     20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
cgggaagact ctgggcaagg                                                     20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
cgggcgcaca aaccagagag                                                     20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
gcaactccag ctgacaaaga                                              20

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
cgaaacccgc tacatagtgg                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
aactcctgga gctcaaggtc                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
acttccgcag acgtaagaga                                              20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
tgcgctaaga actgaggcag                                              20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
ataccagcaa caggacattc                                              20

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
gggatagttg gcttaagtca                                              20

<210> SEQ ID NO 206
<211> LENGTH: 20
<212> TYPE: DNA
<213> ORGANISM: Artificial Sequence

```
<220> FEATURE:
<223> OTHER INFORMATION: Synthetic

<400> SEQUENCE: 206
ggcactttcc tattgtaact                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
cacgtggttg ctacaagtta                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
cagcattgtc actgctctag                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
aacatgaagc acctgctaca                                               20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
acagcgtgaa acttgtagag                                               20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
gcttttgtag gttcatgact                                               20

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
gctgagcatc ttcaaagatt                                               20
```

```
<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
ggtcttggag aaatttcaga                                              20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
gcatgatcct gttttgttca                                              20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
tgcagcttgg gtgtgtattc                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
gccaaaccaa aatagggcta                                              20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
tgtggctgaa gatctcatgg                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
ggaagatttt tatctcctgc                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 219
acttgcagct gatgaaagct                                           20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
tcggttttct caaatagcca                                           20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
gtcacccaca gaatccaatt                                           20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
tgatgtgcaa agcggtcatc                                           20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
gaaggtaagg atgataccca                                           20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
tttgactggc acaaaaggtt                                           20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
ggtgatgaca tatcaagagc                                           20

<210> SEQ ID NO 226
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 226
agccaagaca agtggcaatt                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
ccaacaaact ggtcccttct                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
gtactctgat tttacacgct                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
aacctcttga gctgtctcag                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
ctttacttca tcagctcgtc                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
cttcgctgtt tccattcttg                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
```
aagtcactgg tcaccgaaca                                               20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
atgggatgac ttgtgttgga                                               20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
agcaactgca ttcagagtct                                               20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
ataaaattct gctgtaggggg                                              20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
ctgttcggtg agttctttat                                               20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
gtacattcag gaggaagtgc                                               20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
catcgcctac agaaaagcgt                                               20

<210> SEQ ID NO 239
<211> LENGTH: 20
<212> TYPE: DNA

```
<213> ORGANISM: Artificial Sequence
<220> FEATURE:
<223> OTHER INFORMATION: Synthetic

<400> SEQUENCE: 239
gcacttacga tgtaggaagc                                              20

<210> SEQ ID NO 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
gttgggtgtt gcatgaaaag                                              20

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
ctgtgttctt ccgcttataa                                              20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
aaggtttgtt gtctagagct                                              20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
aatgctggta acactgtggt                                              20

<210> SEQ ID NO 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
gtgagagcag cagcaaactc                                              20

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
tgctactgtt attgggaagc                                              20
```

```
<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
ttccagcaca ttaatggtgg                                               20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
ttggtgtttg acaccgagaa                                               20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
ggactctaaa cattgaggct                                               20

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
taacctagca atggcacaga                                               20

<210> SEQ ID NO 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
ctgtctacat gttttggtcc                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
ctggagctat gatgctagat                                               20

<210> SEQ ID NO 252
<211> LENGTH: 20
<212> TYPE: DNA
<213> ORGANISM: Artificial Sequence
<220> FEATURE:
```

<223> OTHER INFORMATION: Synthetic

<400> SEQUENCE: 252
ctgtatcttt ctgcagtgtg                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
aaacatggtt agaggagccg                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
tggatgatca cagggttgat                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
atcacacaag ggcacgaact                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
agatggtgcc agcaatagat                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
tgataaaaat cccccagcct                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
tctccacagt attctgagat                                               20

```
<210> SEQ ID NO 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
gatggctctc ttggcaaaaa                                               20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
aaaaacagct cttcgccagt                                               20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
tgcccaatac aaccatccag                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
catcttcaca gttcctaaca                                               20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
tgtctgcgta gtagctgttc                                               20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
aggtgttcat ggagttcatg                                               20

<210> SEQ ID NO 265
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 265
tcgtagtcat ggtgttcatg                                               20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
gttggcatag gacatgttga                                               20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
cgcagtcatg ctgttcatgg                                               20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
tagctgcgct tgaacgtctt                                               20

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
gagatgtacg agtagggcgg                                               20

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270
ctggatggcc atggtgatga                                               20

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271
atgatccact ggtagatctc                                               20

<210> SEQ ID NO 272
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 272
tgccggtaat aggggaagag                                                  20

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
agccgttctc gaacatgttg                                                  20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
tgcttctcgc acttgaagcg                                                  20

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275
ctggagtctt caactccgag                                                  20

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
aacgggtggt tgaaggagta                                                  20

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
ggacatgagg ttgttgatgg                                                  20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
```

-continued ttgaagtcca gcttatgctg                                         20

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
tattgcagtg cctgttcgta                                         20

<210> SEQ ID NO 280
<211> LENGTH: 20
<212> TYPE: DNA
<213> ORGANISM: Artificial Sequence
<220> FEATURE:
<223> OTHER INFORMATION: Synthetic

<400> SEQUENCE: 280
caacgtagag ccgtaaggcg                                         20

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
atacacacct tggtagtacg                                         20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
aagtgtttag gacgggtctg                                         20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
ttgcactggg ggaaaggttg                                         20

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
aaattggttt ggggttgtct                                         20

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
ggatcattaa acttcgcagg                                           20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286 gtaggggtc aggtaaggag                                            20

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
attgccacag acctgtaaac                                           20

<210> SEQ ID NO 288
<211> LENGTH: 20
<212> TYPE: DNA
<213> ORGANISM: Artificial Sequence
<220> FEATURE:
<223> OTHER INFORMATION: Synthetic

<400> SEQUENCE: 288
cttttaagag cctctagtgt                                           20

<210> SEQ ID NO 289
<211> LENGTH: 20
<212> TYPE: DNA
<213> ORGANISM: Artificial Sequence
<220> FEATURE:
<223> OTHER INFORMATION: Synthetic

<400> SEQUENCE: 289
agcaaatggc tctgatgttt                                           20

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
gcatgtgcat aattaagtcc                                           20

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
acggaggatg tctacacatc                                           20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
gcaactcttg agaatgtatc                                               20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
ttggggtcct tgtaactttc                                               20

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
attcctgagg aattgattcc                                               20

<210> SEQ ID NO 295
<211> LENGTH: 20
<212> TYPE: DNA
<213> ORGANISM: Artificial Sequence
<220> FEATURE:
<223> OTHER INFORMATION: Synthetic

<400> SEQUENCE: 295
agaagcagag ttcttgaggg                                               20

<210> SEQ ID NO 296
<211> LENGTH: 20
<212> TYPE: DNA
<213> ORGANISM: Artificial Sequence
<220> FEATURE:
<223> OTHER INFORMATION: Synthetic

<400> SEQUENCE: 296
atgacatgac catggcactc                                               20

<210> SEQ ID NO 297
<211> LENGTH: 20
<212> TYPE: DNA
<213> ORGANISM: Artificial Sequence
<220> FEATURE:
<223> OTHER INFORMATION: Synthetic

<400> SEQUENCE: 297
ctctcctcca acattgtaat                                               20

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
aaatccagct ccctataact                    20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
ttgaatcttg gaccacgttt                    20

<210> SEQ ID NO 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
atggccacta tcaataggat                    20

<210> SEQ ID NO 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
agcacacgat ggcaatgatt                    20

<210> SEQ ID NO 302
<211> LENGTH: 20
<212> TYPE: DNA
<213> ORGANISM: Artificial Sequence
<220> FEATURE:
<223> OTHER INFORMATION: Synthetic

<400> SEQUENCE: 302
tccaactgtg gaaagtgcat                    20

<210> SEQ ID NO 303
<211> LENGTH: 20
<212> TYPE: DNA
<213> ORGANISM: Artificial Sequence
<220> FEATURE:
<223> OTHER INFORMATION: Synthetic

<400> SEQUENCE: 303
gtctggctat actaacacca                    20

<210> SEQ ID NO 304
<211> LENGTH: 20
<212> TYPE: DNA
<213> ORGANISM: Artificial Sequence
<220> FEATURE:
<223> OTHER INFORMATION: Synthetic

<400> SEQUENCE: 304
gaacattttc cacggcttaa                    20

<210> SEQ ID NO 305

```
<211> LENGTH: 20
<212> TYPE: DNA
<213> ORGANISM: Artificial Sequence
<220> FEATURE:
<223> OTHER INFORMATION: Synthetic

<400> SEQUENCE: 305
gtccttaact gcaaatgatc                                                    20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
aaacacagaa ggcttaagcc                                                    20

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
ttaattctat cagccacagc                                                    20
```

COMPOSITIONS AND METHODS FOR TREATING CANCER

This application claims priority to U.S. provisional patent application Ser. No. 62/655,308, filed Apr. 10, 2018, which is incorporated herein by reference in its entirety.

STATEMENT REGARDING FEDERALLY SPONSORED RESEARCH OR DEVELOPMENT

This invention was made with government support under grants CA186786 and CA214170 awarded by the National Institutes of Health and under W81XWH-13-1-0284 and W81XWH-16-1-0314 awarded by the U.S. Army, Medical Research and Materiel Command. The government has certain rights in the invention.

FIELD

Provided herein are compositions and methods for treating cancer. In particular, provided herein are compositions, methods, and uses of inhibitors of ARlnc1 for treating cancer.

BACKGROUND 27,000 Americans will die from prostate cancer (PCa) in 2017. PCa is the most common cancer in men and the number two killer overall. For patients with metastatic PCa that fail hormone therapy, the last line of defense are the taxane-derived chemotherapeutic agents docetaxel (Taxotere) or cabazitaxel (Jevtana). Response to taxane therapy is not durable. Progression-free survival on docetaxel treatment approaches 0% by 3 years (see, e.g., Petrylak D P, et al., New Engl J Med. 2004; 351(15):1513-20).

There is a need for additional diagnostic and treatment options, particularly treatments customized to a patient's tumor.

SUMMARY

Provided herein are compositions and methods for treating cancer. In particular, provided herein are compositions, methods, and uses of inhibitors of ARlnc1 for treating cancer.

For example, in some embodiments, provided herein is a method of treating cancer, comprising: administering an agent that blocks the expression or activity of ARlnc1 to a subject diagnosed with cancer under conditions such that a sign or symptom of the cancer is reduced. The present disclosure is not limited to particular agents. Examples include, but are not limited to, a nucleic acid (e.g., antisense, siRNA, miRNA, shRNA, etc.) that inhibits expression of ARlnc1. The present disclosure is not limited to a particular cancer. In some embodiments, the cancer is prostate cancer. In some embodiments, the cancer expresses ARlnc1. For example, in some embodiments, ARlnc1 is overexpressed in the cancer relative to the level of expression in non-cancerous cells. In some embodiments, the method further comprises the step of assaying a sample of the cancer for the level of expression of ARlnc1.

Further embodiments provide a method, comprising: a) assaying a sample from a subject diagnosed with cancer, wherein the sample comprises cancer tissue or cells, for the level of expression of ARlnc1; and b) administering an agent that blocks the expression or activity of ARlnc1 when expression or overexpression of ARlnc1 is present in the sample.

Additional embodiments provide the use of an agent that inhibits expression of ARlnc1 to treat cancer in a subject.

Certain embodiments provide a composition comprising an agent that inhibits expression of ARlnc1 for use in the treatment of cancer in a subject.

Also provided herein is a composition, comprising: a) an agent that inhibits expression of ARlnc1; and b) a pharmaceutically acceptable carrier.

Additional embodiments are described herein.

(e) Scatter plot representing the average number of ARLNC1 transcripts per cell in a panel of prostate cancer cell lines, including MDA-PCa-2b, LNCaP, VCaP, 22Rv1, PC3, RWPE, and DU145. (f) Representative gray-scale images of MDA-PCa-2b cells stained for DAPI (nucleus) and ARLNC1, AR or GAPDH transcripts (smFISH). (g) Percentage of nuclear/cytoplasmic RNA levels of ARLNC1, ACTB, and U1, measured by qRT-PCR after subcellular fractionation of MDA-PCa-2b and LNCaP cells.

Figure 12:
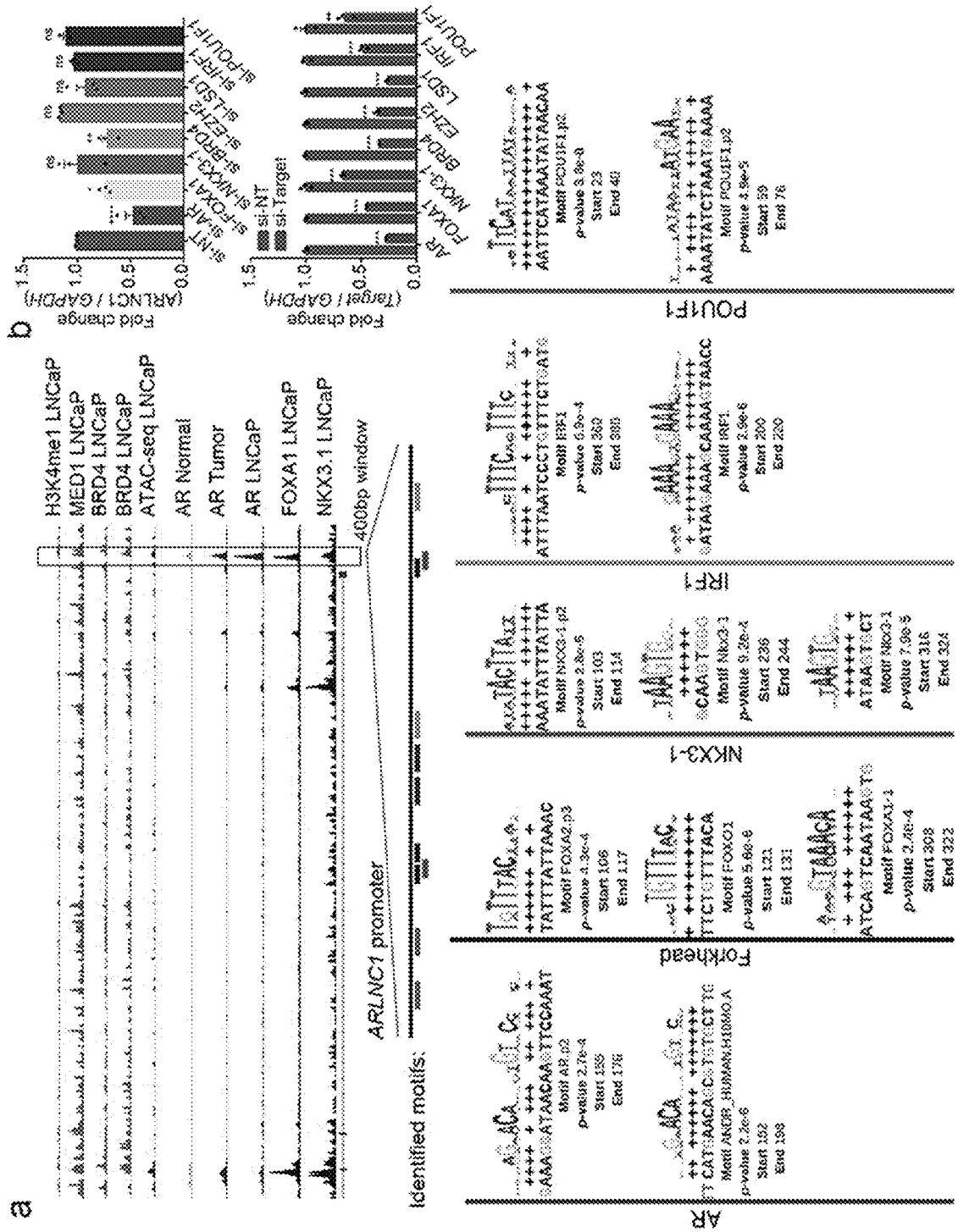
Figure 12:
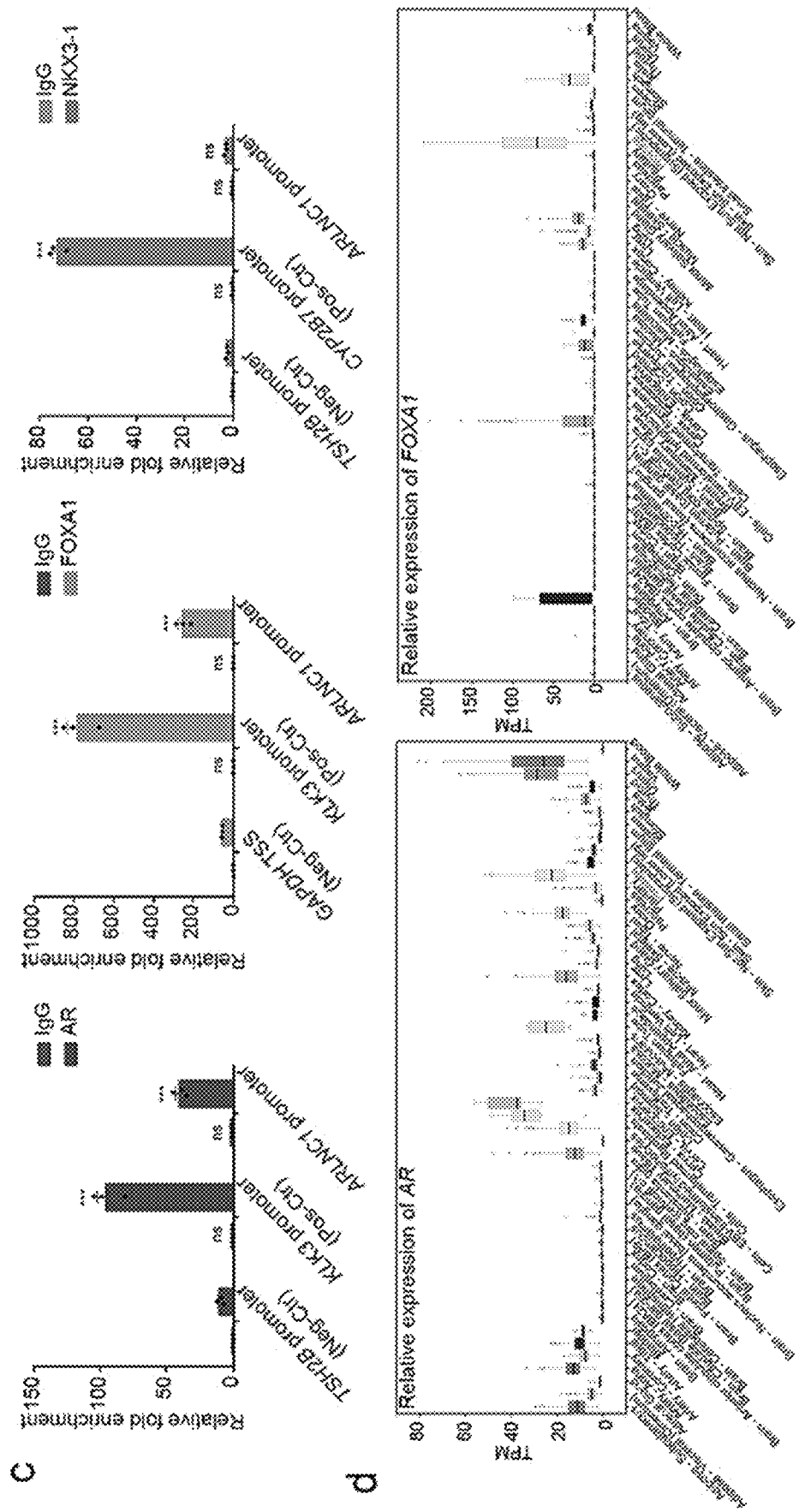

FIG. 12 shows that ARLNC1 expression is regulated by AR and FOXA1. (a) ChIP-seq peaks of H3K4me1, MED1, BRD4, FOXA1, and NKX3-1 from LNCaP cells at the ARLNC1 promoter region. (b) Top panel: qPCR analysis of ARLNC1 expression in LNCaP cells, following treatment with siRNAs targeting AR, FOXA1, NKX3-1, BRD4, EZH2, LSD1, IRF1, and POU1F1. (c) ChIP-PCR analysis in MDA-PCa-2b cells showing relative enrichment (ChIP/input) of AR, FOXA1, NKX3-1 or IgG over ARLNC1 promoter region or control region. (d) Relative expression (TPM) of AR (Left) and FOXA1 (Right) across a panel of normal tissues in GTEx normal tissue RNA-seq cohort (n=8,745 samples).

Figure 13:
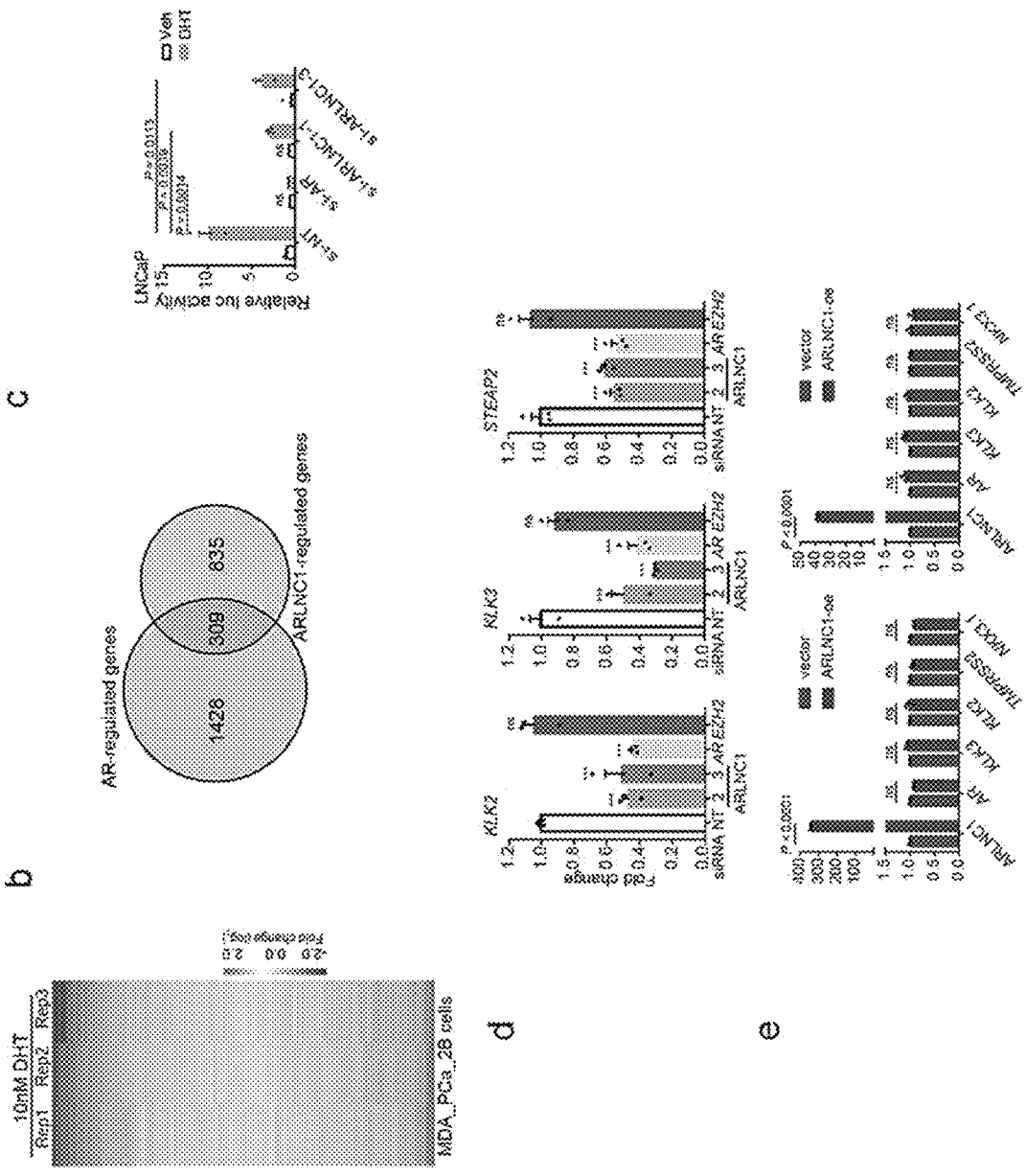

FIG. 13 shows a positive feedback loop between ARLNC1 and AR signaling. (a) Reproducibility of expression profiling following 10 nM DHT treatment in MDA-PCa-2b cells. (b) Overlap between genes differentially expressed upon AR knockdown and ARLNC1 knockdown in MDA-PCa-2B cells. (c) siRNA knockdown of ARLNC1 in LNCaP cells impaired AR signaling by AR reporter gene assay. (d) qRT-PCR analysis of KLK2, KLK3, and STEAP2, in MDA-PCa-2b cells transfected with siRNAs against ARLNC1, AR, EZH2, or non-specific control. (e) qPCR analysis of ARLNC1 and AR signaling genes in LNCaP cells (Left panel) and MDA-PCa-2b cells (Right panel) transfected with ARLNC1 expressing vector or control vector.

Figure 14:
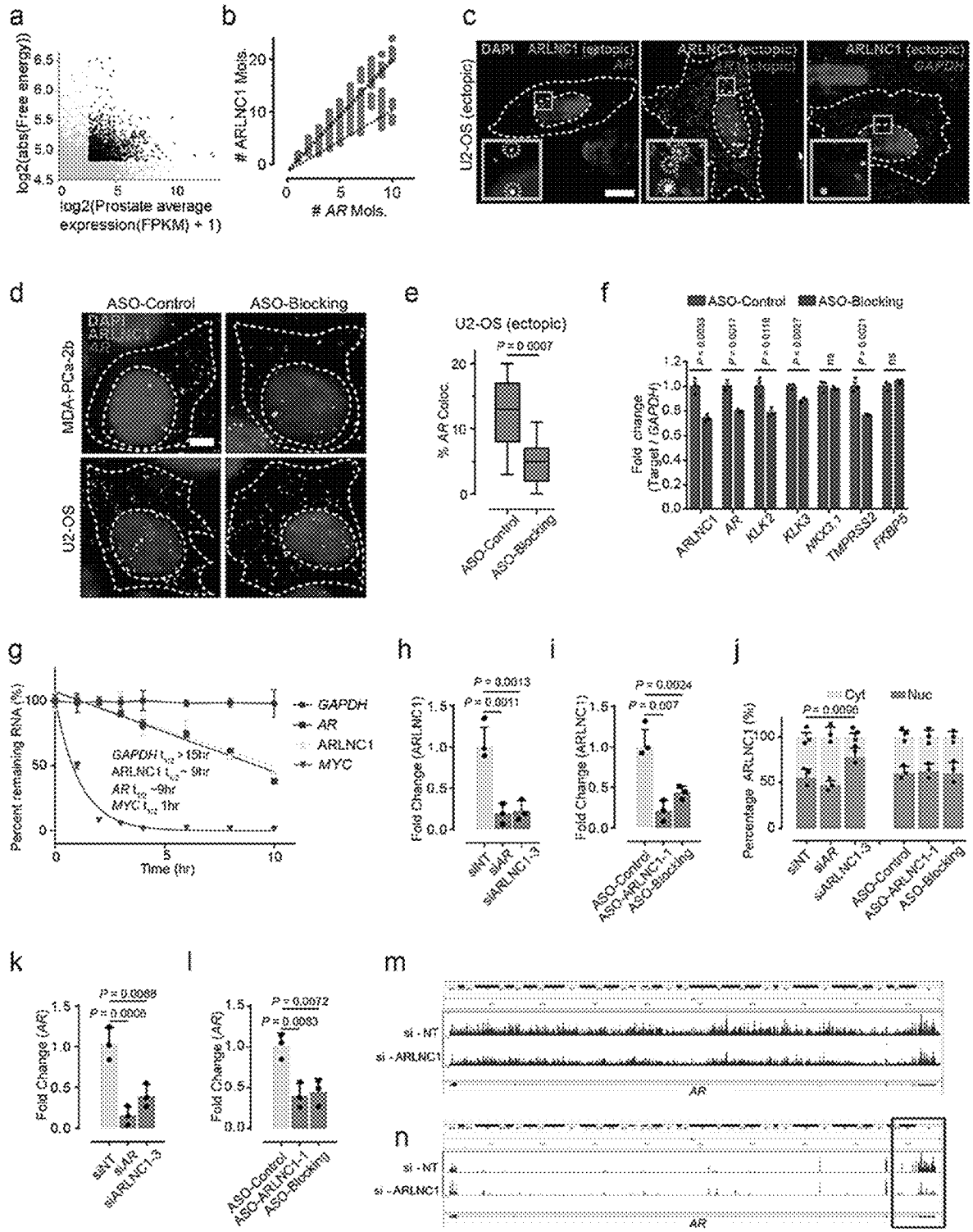

FIG. 14 shows post-transcriptional regulation of AR by ARLNC1. (a) In silico prediction of ARLNC1 RNA-binding partners, with y-axis representing log 2-absolute RNA binding energy between ARLNC1 and various RNA species, while x-axis depicting log 2-average expression level of these RNAs in prostate cancer. (b) Stoichiometry of ARLNC1:AR colocalization. (c) Representative pseudocolored images of U2-OS cells ectopically expressing ARLNC1 alone (green, left and right panels), or both ARLNC1 and AR (middle panel), and stained for the appropriate transcripts and DAPI. (d-e) Representative pseudo-colored images of MDA-PCa-2b cells or U2-OS cells stained for DAPI (nucleus) and ARLNC1 and AR transcripts, following treatment of blocking ASOs targeting the ARLNC1:AR 3'UTR interaction. Quantification of colocalization in U2-OS cells are depicted in (e) as a box plot, whereas quantifications of colocalization in MDA-PCa-2b cells are in FIG. 6f. (f) qPCR analysis of ARLNC1, AR transcript and AR signaling gene (KLK2, KLK3, NKX3-1, TMPRSS2, FKBP5) expression in LNCaP cells transfected with control ASO or blocking oligos targeting the interaction sites between ARLNC1 and AR 3'UTR. (g) Half-life of GAPDH, AR, ARLNC1, and MYC RNA transcripts in LNCaP cells. (h-i) Quantification of ARLNC1 levels, as measured by smFISH, after treatment of MDA-PCa-2b cells with siRNA against AR (siAR), siRNA against ARLNC1 (siARLNC1-3), ASO against ARLNC1 (ASO-ARLNC1-1) or blocking ASO against AR-ARLNC1 colocalizing segment (ASO-Blocking). Data were normalized to siNT (h) or ASO-Control (i). (j) Nucleo-cytoplasmic distribution of ARLNC1 after appropriate treatment of MDA-PCa-2b cells with siRNA against AR (siAR), siRNA against ARLNC1 (siARLNC1-3), ASO against ARLNC1 (ASO-ARLNC1-1) or blocking ASO against AR-ARLNC1 colocalizing segment (ASO-Blocking). (k-l) Quantification of AR levels, as measured by smFISH, after treatment of MDA-PCa-2b cells with siRNA against AR (si-AR), siRNA against ARLNC1 (si-ARLNC1-3), ASO against ARLNC1 (ASO-ARLNC1-1) or blocking ASO against AR-ARLNC1 colocalizing segment (ASO-Blocking). Data were normalized to siNT (k) or ASO-Control (l). Mean±s.e.m. are shown, n=3 independent experiments and 60 cells analyzed for each sample. (m-n) BrU-seq alignment track (m) and BrUChase-seq alignment track (n) at AR gene locus.

Figure 15:
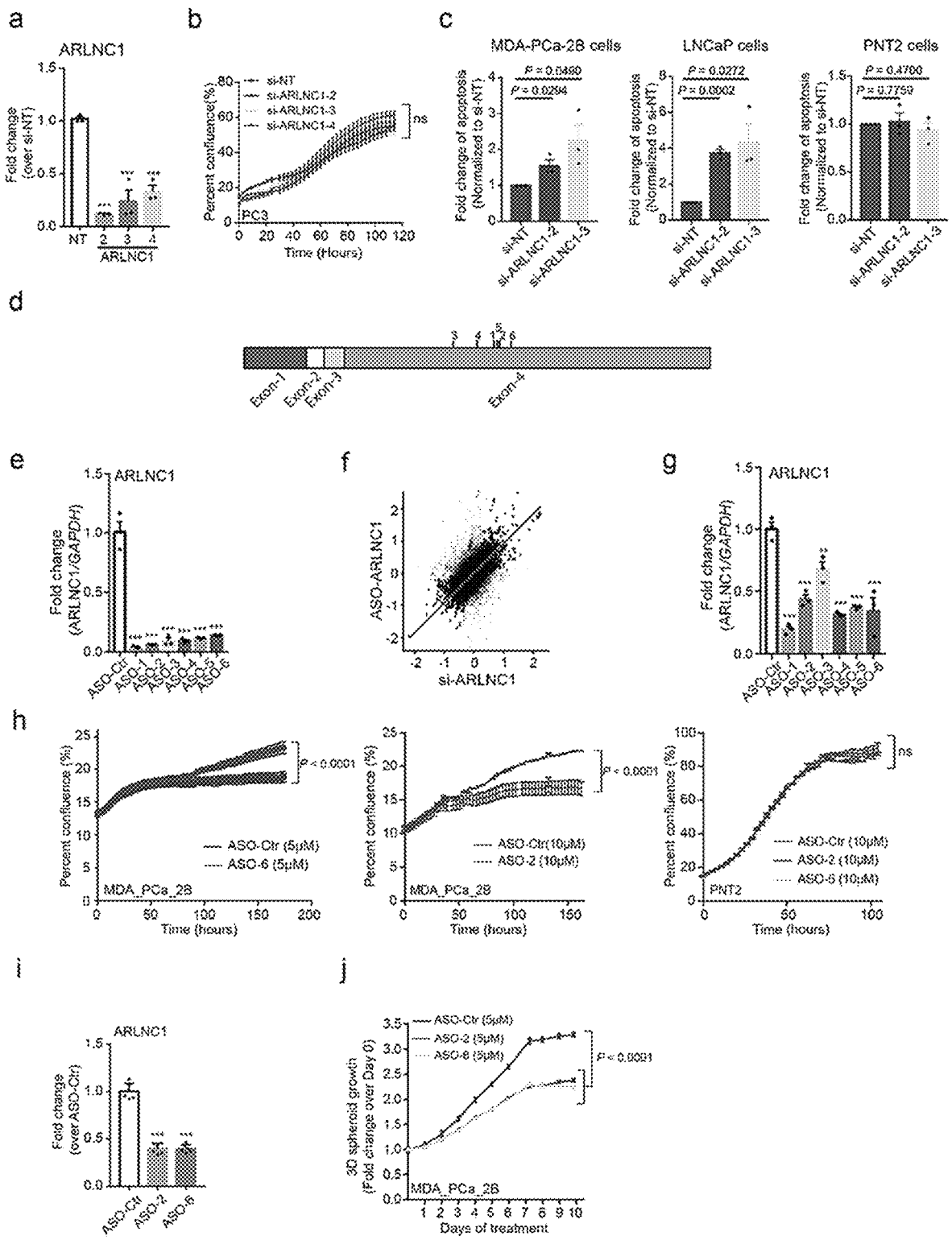

FIG. 15 shows evaluation of the phenotypic effect of ARLNC1 in vitro. (a) Knockdown efficacy of three independent siRNAs targeting ARLNC1 in MDA-PCa-2b cells. (b) ARLNC1 siRNA transfection has no effect on cell proliferation in ARnegative prostate cancer cells, PC3. (c) Increased apoptosis observed in MDA-PCa-2b and LNCaP cells 48 hours after transfected with ARLNC1 siRNAs. (d) Positions of ARLNC1 antisense oligo (ASO)-targeting sites (1 to 6) is indicated on the schematic representation of the ARLNC1 transcript. (e) MDA-PCa-2b cells were transfected with six independent ASOs targeting ARLNC1. (f) Correlation analysis of siRNA-mediated knockdown and ASO-mediated knockdown of ARLNC1 among replicated microarray experiments in MDA-PCa-2b cells (n=2 biological replicates per ASO treatment group and n=3 biological replicates per siRNA treatment group). (g) Free-uptake efficacy of ARLNC1 ASOs was examined in MDA-PCa-2B cells 72 hours post ASO addition to the culture medium (10 μM). (h) Free-uptake treatment of ASOs targeting ARLNC1 resulted in retarded growth of MDA-PCa-2b cells in vitro. (i-j) ARLNC1 ASOs inhibit MDA-PCa-2b cell proliferation in 3D-sphere models.

Figure 16:
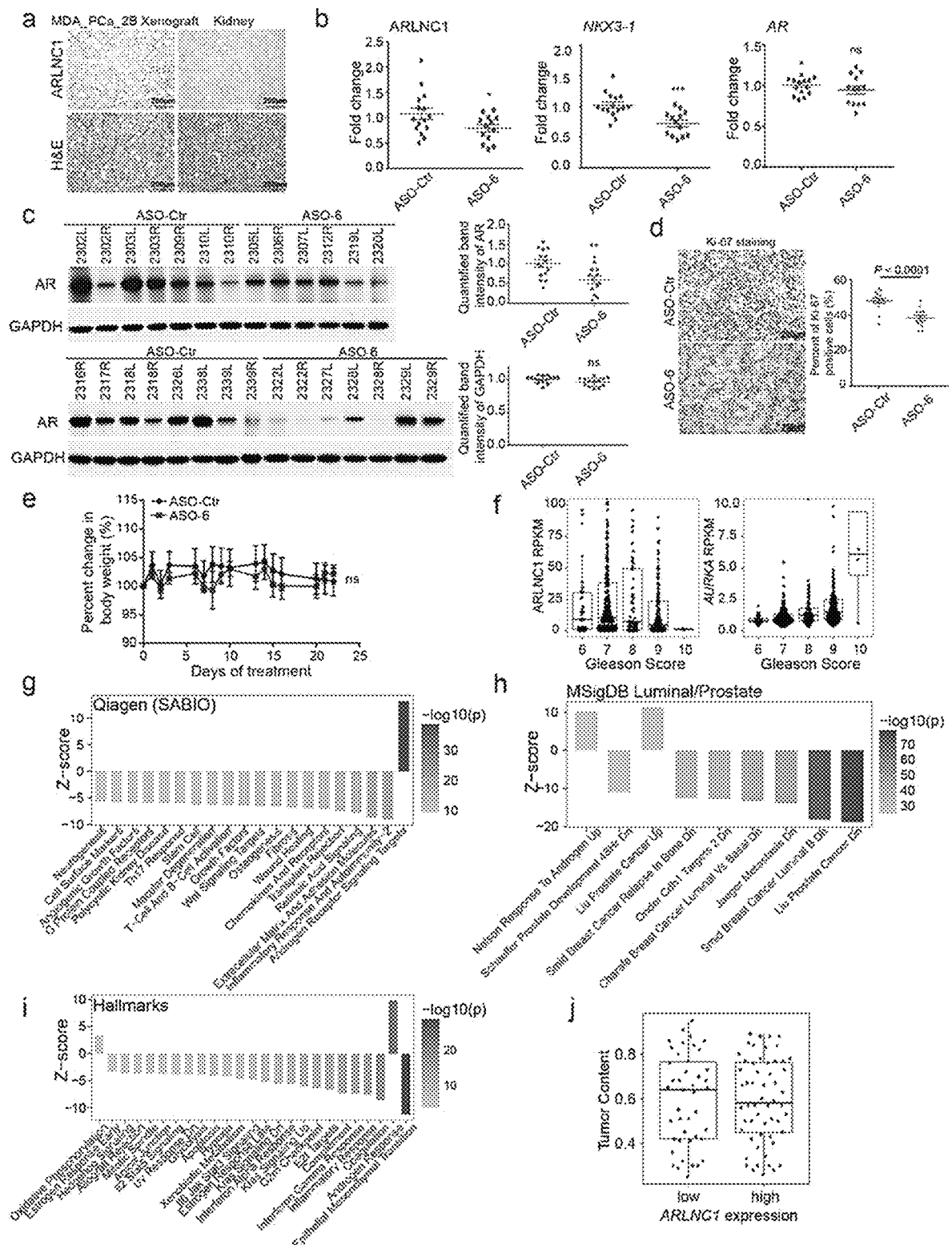

FIG. 16 shows that knockdown of ARLNC1 by ASOs inhibits tumor growth in vivo. (a) Representative image of in situ hybridization for ARLNC1 in MDA-PCa-2b cell line-derived xenograft. (b) qRT-PCR analysis of ARLNC1, NKX3-1 and AR transcripts in MDA-PCa-2b xenografts treated with control ASO (n=15) or ASO targeting ARLNC1 (n=13). (c) Left: Immunoblots of AR and GAPDH in MDA-PCa-2b xenografts treated with control ASO (n=15) or ASO targeting ARLNC1 (n=13). Right: Relative intensity of the bands was quantified using ImageJ. (d) Left: Immunohistochemistry staining for Ki67 in MDA-PCa-2b xenograft treated with control ASO or ASO against ARLNC1. Right: Summary of Ki67 tumor staining for control (n=15) or ARLNC1 ASO-treated tumors (n=13) shows significant difference in Ki67 staining intensity. (e) Percent change in mice body weight over the time of ASO treatment in MDA-PCa-2b xenografts treated with control ASO (n=15) or ASO targeting ARLNC1 (n=13). (f) ARLNC1 expression levels are not associated with Gleason score. (g) Curated pathway signature analysis between ARLNC1 high (top-quartile) and ARLNC1 low (bottom-quartile) mCRPC samples (n=100). (h) Signatures associated with prostate cancer and luminal differentiation were selected from the MSigDB and contrasted between ARLNC1 high (top-quartile) and ARLNC1 low (bottom-quartile) mCRPC samples (n=100). (i) Cancer hallmark signature analysis between ARLNC1 high expression (top-quartile) and ARLNC1 low expression (bottom-quartile) mCRPC samples (n=100 samples). (j) Tumor content estimated from whole-exome sequencing is compared between ARLNC1 high (top-quartile) and ARLNC1 low (bottom-quartile) expression in mCRPC samples (n=100).

DEFINITIONS

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of cancer. A subject suspected of having cancer may also have one or more risk factors. A subject suspected of having cancer has generally not been tested for cancer. However, a "subject suspected of having cancer" encompasses an individual who has received a preliminary diagnosis but for whom a confirmatory test has not been done or for whom the level or severity of cancer is not known.

As used herein, the term "subject diagnosed with cancer" refers to a subject who has been tested and found to have cancer. As used herein, the term "initial diagnosis" refers to a test result of initial disease that reveals the presence or absence of disease.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., ARlnc1 inhibitor described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include, but are not limited to, single-stranded and double-stranded compounds, such as, antisense oligonucleotides, siRNAs and shRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases. "Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Oligonucleotide" means a polymer of linked nucleosides each of which can be modified or unmodified, independent one from another.

DETAILED DESCRIPTION OF THE DISCLOSURE

Provided herein are compositions and methods for treating cancer. In particular, provided herein are compositions, methods, and uses of inhibitors of ARlnc1 for treating cancer.

Long non-coding RNAs (lncRNAs) are a class of transcripts with diverse and largely uncharacterized biological functions[1-3]. Through cross-talk with chromatin, DNA, RNA species, and proteins, lncRNAs function via chromatin remodeling, transcriptional and post-transcriptional regulation[4-9]. High-throughput RNA sequencing (RNA-Seq) has enabled the identification of lncRNAs with oncogenic and tumor suppressive roles, including involvement in the pathogenesis of prostate cancer (PCa)[7,10-12]. Primary PCa is often hormone-dependent and relies on signaling through the androgen receptor (AR); therefore, the majority of patients are responsive to front-line treatment with androgen deprivation therapy (ADT)[13-15]. However, approximately 20% of cases progress to an incurable stage of the disease known as castration-resistant prostate cancer (CRPC), which still critically relies on AR signaling[16,17], as evidenced by the clinical benefit afforded through the use of enzalutamide[18-21] or abiraterone[22-24]. While substantial efforts have been undertaken to identify mechanisms of sustained AR signaling in CRPC (e.g., AR mutations, AR splice variants, and alternative activation pathways)[25-31], few studies have investigated the role of AR-regulated lncRNAs. Therefore, described herein is a comprehensive RNA-Seq profiling investigation of AR-regulated, cancer-associated lncRNAs from prostate cancer cell lines and patient tissue samples. During such experiments, ARlnc1 was identified as a target in prostate cancer.

Accordingly, provided herein are compositions and methods for treating cancer by inhibiting the expression and/or function of ARlnc1.

I. Inhibitors

In some embodiments, the ARlnc1 inhibitor is selected from, for example, a nucleic acid (e.g., siRNA, shRNA, miRNA or an antisense nucleic acid), a small molecule, a peptide, or an antibody.

In some embodiments, the ARlnc1 inhibitor is a nucleic acid. Exemplary nucleic acids suitable for inhibiting ARlnc1 (e.g., by preventing expression of ARlnc1) include, but are not limited to, antisense nucleic acids and RNAi. In some embodiments, nucleic acid therapies are complementary to and hybridize to at least a portion (e.g., at least 5, 8, 10, 11, 12, 13, 14, 15, 16, 17, 18, 19, or 20 nucleotides) of ARlnc1.

In some embodiments, compositions comprising oligomeric antisense compounds, particularly oligonucleotides are used to modulate the function of nucleic acid molecules encoding ARlnc1, ultimately modulating the amount of ARlnc1 expressed. This is accomplished by providing antisense compounds that specifically hybridize with one or more nucleic acids encoding ARlnc1. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of ARlnc1 proteins in the cell.

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the R.sub.1SC pathway and include, without limitation, siRNA, ssRNA and microRNA mechanisms; and occupancy based mechanisms. Certain antisense compounds may act through more than one such mechanism and/or through additional mechanisms.

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include .beta.-D-ribonucleosides, .beta.-D-deoxyribonucleosides, 2'-modified nucleosides (such 2'-modified nucleosides may include 2'-MOE and 2'-O—CH.sub.3, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X—Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound has a gapmer motif in which the gap consists of 6, 7, 8, 9, 10, 11, 12, 13, 14, 15, or 16 linked nucleosides.

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is (AB).sub.xA.sub.y wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type.

In certain embodiments, oligonucleotides having such an alternating motif also comprise a modified 5' terminal nucleoside, such as those of formula IIc or IIe.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Additional modifications are described, for example, in U.S. Pat. No. 9,796,976, herein incorporated by reference in its entirety.

In some embodiments, nucleic acids are RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, ARlnc1.

An "RNA duplex" refers to the structure formed by the complementary pairing between two regions of a RNA molecule. The RNA using in RNAi is "targeted" to a gene in that the nucleotide sequence of the duplex portion of the RNAi is complementary to a nucleotide sequence of the targeted gene. In certain embodiments, the RNAi is are targeted to the sequence encoding ARlnc1. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter. The nucleic acid sequence can also include a polyadenylation signal. In some embodiments, the polyadenylation signal is a synthetic minimal polyad n certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of ARlnc1.

In some embodiments, hybridization occurs between an antisense compound disclosed herein and an ARlnc1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ARlnc1 nucleic acid).

Non-complementary nucleobases between an antisense compound and an ARlnc1 nucleic acid may be tolerated provided that the antisense compound remains able to specifically hybridize to a target nucleic acid. Moreover, an antisense compound may hybridize over one or more segments of an ARLNC1 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an ARlnc1 nucleic acid, a target region, target segment, or specified portion thereof. Percent complementary of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Alnc1 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ARlnc1 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Alnc1 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. In certain embodiments, the antisense compounds are complementary to at least an 18 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

The present disclosure contemplates the use of any genetic manipulation for use in modulating the expression of ARlnc1. Examples of genetic manipulation include, but are not limited to, gene knockout (e.g., removing the ARlnc1 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Exemplary methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice.

Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety. Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 1999/02685 herein incorporated by reference in its entirety). Exemplary dose levels of adenoviral vector are preferably $10^8$ to $10^{11}$ vector particles added to the perfusate.

In some embodiments, CRISPR/Cas9 systems are used to delete or knock out genes. Clustered regularly interspaced short palindromic repeats (CRISPR) are segments of prokaryotic DNA containing short, repetitive base sequences. These play a key role in a bacterial defence system, and form the basis of a genome editing technology known as CRISPR/Cas9 that allows permanent modification of genes within organisms.

In some embodiments, the present disclosure provides antibodies that inhibit ARlnc1. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, candidate ARlnc1 inhibitors are screened for activity (e.g., using the methods described herein or another suitable assay).

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

II. Methods of Treating Cancer

Provided herein are methods of treating cancer (e.g., prostate cancer). In some embodiments, a sample of tumor or cancerous tissue from the subject is first tested for expression of ARlnc1. In some embodiments, treatment is administered to individuals with expression of ARlnc1 and/or individuals with levels of expression of ARlnc1 greater than the levels in non-cancerous tissue. In some embodiments, samples of tumor or cancer tissue are tested during treatment in order to determine whether or not to continue treatment.

In some embodiments, the compounds and pharmaceutical compositions described herein are administered in combination with one or more additional agents, treatment, or interventions (e.g., agents, treatments, or interventions useful in the treatment of cancer).

In some embodiments, ARlnc1 inhibitors are co-administered with an anti-cancer agent (e.g., chemotherapeutic). The present disclosure is not limited by type of anti-cancer agent co-administered.

EXPERIMENTAL

The following examples are provided in order to demonstrate and further illustrate certain preferred embodiments and aspects of the present disclosure and are not to be construed as limiting the scope thereof.

Example 1

Methods

Cell Lines.

Cell lines were purchased from the American Type Culture Collection (ATCC) and maintained using standard media and conditions. VCaP cells were maintained in DMEM (Invitrogen) supplemented with 10% fetal bovine serum (FBS). LNCaP cells were maintained in RPMI 1640 (Invitrogen) supplemented with 10% FBS. MDA-PCa-2b cells were maintained in ATCC-formulated F-12K medium, supplemented with 20% FBS, 25 ng/ml cholera toxin, 10 ng/ml mouse epidermal growth factor, 100 µg/ml hydrocortisone, 0.005 mM phosphoethanolamine, 45 nM selenous acid, and 0.005 mg/ml bovine insulin. All cell lines were grown at 37° C. in 5% $CO_2$ cell culture incubators, genotyped by DNA fingerprinting analysis, and tested for mycoplasma infection every two weeks. All cell lines used in this study were mycoplasma-negative.

DHT treatment was performed to identify AR-regulated genes. DHT was purchased from Sigma-Aldrich and used at a final concentration of 10 nM. VCaP and LNCaP cells were grown in charcoal-stripped serum containing media for 48 hours and then stimulated with 10 nM DHT for six or 24 hours.

RNA-Seq.

Total RNA was extracted from LNCaP and VCaP cells following DHT treatment using the miRNeasy kit (QIAGEN). RNA quality was assessed using the Agilent Bioanalyzer. Each sample was sequenced using the Illumina HiSeq 2000 (with a 100-nt read length) according to published protocols[52].

RNA-Seq Data Analysis to Identify AR-Regulated Genes.

RNA-Seq data were analyzed as previously described[53]. Briefly, the strand-specific paired-end reads were inspected for sequencing and data quality (e.g. insert size, sequencing adapter contamination, rRNA content, sequencing error rate). Libraries passing QC were trimmed of sequencing adapters and aligned to the human reference genome, GRCh38. Expression was quantified at the gene level using the "intersection non-empty" mode[54] as implemented in featureCounts[55] using the Gencode v22[56] and/or MiTranscriptome assemblies[10]. All pairwise differential expression analyses were carried out using the voom-limma approach[57,58] with all default parameters. Relative expression levels (FPKMs, fragments per kilobase of transcript per million mapped reads) were normalized for differences in sequencing depth using scaling factors obtained from the calcNormFactors (default parameters) function from edgeR[59].

AR-regulated genes (ARGs) were identified from expression data of VCaP and

LNCaP cells treated with DHT after six and 24 hours using three linear models: separate models for each of the cell lines treating the two time-points as biological replicates, and a merged model with all treated samples as replicates. ARGs were defined as genes that were significant (P value<0.1 and absolute log fold-change>2) in both separate models and/or the merged model.

Identification of Prostate Cancer Associated Protein-Coding Genes and lncRNAs.

Raw RNA-Seq data for primary and metastatic patients were obtained from the TCGA/PRAD and PCF/SU2C projects, respectively. External transcriptome samples were re-analyzed using in-house pipelines (see above) to facilitate direct comparisons of expression levels and identification of DEGs. Pan-cancer analyses based on the MiTranscriptome assembly[10] were leveraged as FPKMs and enrichment scores (SSEA) computed as part of that project. To visualize data, fold changes were computed relative to median expression levels estimated across the combined (normal, primary, metastatic) cohorts and subjected to unsupervised hierarchical clustering separately within each cohort. Tissue lineage (prostate) and prostate cancer-specific genes were identified using the sample set enrichment analysis (SSEA) method as previously described[10]. Briefly, the SSEA test was used to determine whether each gene was significantly associated with a set of samples (e.g. prostate cancer), or cancer progression in a given lineage (e.g. prostate normal to prostate cancer). The genes were ranked according to their strength of association.

Oncomine Concept Analysis of the ARlnc1 Signature.

Genes with expression levels significantly correlated with ARlnc1 were separated into positively and negatively correlated gene lists. These two lists were then imported into Oncomine as custom concepts and queried for association (similarity) with other prostate cancer concepts housed in Oncomine. All the prostate cancer concepts with odds ratio>2.0 and p-value<1×10$^{-4}$ were selected. For simplicity, top concepts (based on odds ratios) were selected for representation. We exported these results as the nodes and edges of a concept association network and visualized the network using Cytoscape version 3.3.0. Node positions were computed using the Edge-weighted force directed layout in Cytoscape using the odds ratio as the edge weight. Node positions were subtly altered manually to enable better visualization of Mode labels[60].

Chromatin Immunoprecipitation (ChIP)-Seq Data Analysis.

ChIP-Seq data from published external and in-house data sets, GSE56288 and GSE55064, were reanalyzed using a standard pipeline. Briefly, groomed reads (vendor QC, adapter removal) were aligned to the GRCh38 reference genome using STAR settings that disable spliced alignment: outFilterMismatchNoverLmax: 0.05, outFilterMatchNmin: 16, outFilterScoreMinOverLread: 0, outFilterMatchNminOverLread: 0, alignIntronMax: 1. Improperly paired alignments and non-primary alignments were discarded. Peaks were called using MACS2 (callpeak—broad—qvalue 0.05—broad-cutoff 0.05 and callpeak—call-summits—qvalue 0.05)[62] and Q (−n 100000)[57]. ChIP enrichment plots were computed from alignment coverage files (BigWig[63]) as trimmed (trim=0.05) smooth splines (spar=0.05). The baseline (non-specific) ChIP signal was estimated from genomic windows furthest from the center of the queried region (peak summit, transcription start site) and subtracted from each signal before plotting.

AR Binding Motif Search.

Unsupervised motif search was carried out using MEME[59]. For each AR ChIP-Seq dataset, the 10,000 most significant AR-binding sites were identified, pruned of likely artifacts, and reduced[64] to a set of most significant, recurrent "uni" AR peaks. DNA sequences (GRch38) from the uni-peak regions overlapping promoters (5 kb upstream, 1 kb downstream of the assembled or known TSS) of ARGs were used as input to MEME (default parameters).

Chip-Qpcr Analysis.

AR ChIP was performed following a previous protocol[32]. Antibodies: AR, Millipore Cat #06-680; FOXA1, Thermo Fisher Cat #PAS-27157; NKX3-1, CST Cat #83700S.) Quantitative PCR (qPCR) analysis was performed using primers listed in Table 1. Primers targeting CYP2B7 promoter were purchased from CST, Cat #84846.

RNA In Situ Hybridization (RNA ISH) on Tissue Microarray.

In situ hybridization assays were performed on tissue microarray sections from Advanced Cell Diagnostics, Inc. as described previously[7]. In total, 133 tissue samples were included, including 11 from benign prostate, 85 from localized prostate cancer, and 37 from metastatic prostate cancer. ARlnc1 ISH signals were examined in morphologically-intact cells and scored manually by a study, using a previously described expression value scoring system[65]. For each tissue sample, the ARLNC1 product score was averaged across evaluable TMA tissue cores. Mean ARLNC1 product scores were plotted in FIG. 2e.

RACE.

5' and 3' RACE were performed to determine the transcriptional start and termination sites of ARlnc1, using the GeneRacer RLM-RACE kit (Invitrogen), according to the manufacturer's instructions.

Northern Blot Analysis.

To validate the presence of ARlnc1 in MDA-PCa-2b cells, Northern blotting was performed using the NorthernMax Kit (Ambion) following the manufacturer's protocol. Briefly, 20 µg of total RNA was extracted from MDA-PCa-2b or DU145 cells, denatured with formaldehyde loading dye solution for 10 minutes at 70° C., and separated on a 1% agarose formaldehyde gel. The RNA was then transferred to nylon membrane (Roche), cross-linked to the membrane (UV Stratalinker 1800; Stratagene), and the membrane was pre-hybridized in ultrahybridization solution at 68° C. for 1 hour. Hybridization followed at 68° C. overnight with the ARlnc1-specific biotinylated riboprobe added to the ultra-hybridization solution. The membrane was washed, and the bound biotinylated probe was detected with the CDP-Star Chemiluminescent Substrate (Sigma-Aldrich). For the synthesis of ARlnc1-specific biotinylated riboprobe, biotin was randomly incorporated into the ARlnc1 antisense RNA upon transcription using ARlnc1 full-length PCR product as template (Roche). The primer sequences used for generating the probes are given in Table 1.

RNA Isolation and cDNA Synthesis.

Total RNA from cell lines was isolated using QIAzol Lysis reagent (QIAGEN) and miRNeasy kit (QIAGEN) with DNase I digestion according to manufacturer's instructions. cDNA was synthesized using Superscript III (Invitrogen) and random primers (Invitrogen).

qRT-PCR Analysis.

Relative RNA levels determined by qRT-PCR were measured on an Applied Biosystems 7900HT Real-Time PCR System, using Power SYBR Green MasterMix (Applied Biosystems). All of the primers were obtained from Integrated DNA Technologies (IDT), and gene-specific sequences are listed in Table 1. GAPDH, HMBS, or ACTB were used as internal controls for quantification of gene targets. The relative expression of RNAs was calculated using ΔΔCt method.

Cytoplasmic and Nuclear RNA Purification

Cytoplasmic and nuclear fractionation was performed using the NE-PER nuclear extraction kit (Thermo Scientific) according to manufacturer's instructions. RNA was extracted using the previously mentioned protocol.

siRNA-Mediated Knockdown.

siRNA oligonucleotides targeting ARLNC1, AR, FOXA1, BRD4, NKX3-1, LSD1, IRF1, POU1F1, or EZH2 and a non-targeting siRNA were purchased from Dharmacon. (si-AR-pool, Cat #L-003400-00-0005; si-FOXA1, Cat #LU-010319-00-0005; si-BRD4, Cat #LU-004937-00-0002; si-NKX3-1, Cat #LU-015422-00-0005; si-LSD1, Cat #LU-009223-00-0002; si-IRF1, Cat #LU-011704-00-0005; si-POU1F1, Cat #LU-012546-00-0005; si-EZH2, Cat #L-004218-00-0005; si-NT, Cat #D-001810-01-05.) siRNA sequences for ARLNC1 knockdown are listed in Table 1. For AR knockdown, two more siRNAs were purchased from Life Technologies (#HSS179972, #HSS179973). Transfections with siRNA (50 nM) were performed with Lipofectamine RNAiMAX according to the manufacturer's instructions. RNA and protein were harvested for analysis 72 hours after transfection.

ASO-Mediated Knockdown.

Antisense oligos targeting ARlnc1 were obtained from Ionis Pharmaceuticals. Transfections with ASOs (50 nM) were performed with Lipofectamine RNAiMAX according to the manufacturer's instructions. RNA and protein were harvested for analysis 72 hours after transfection.

Gene Expression Profiling.

Total RNA was extracted following the aforementioned protocol. RNA integrity was assessed using the Agilent Bioanalyzer. Microarray analysis was carried out on the Agilent Whole Human Oligo Microarray platform, according to the manufacturer's protocol. siRNA-mediated knockdown experiments were run in technical triplicates, comparing knockdown samples treated with two independent ARlnc1 siRNAs to samples treated with non-targeting control siRNA. ASO-mediated knockdown experiments were run in technical replicates, comparing knockdown samples treated with two ARlnc1 ASOs to samples treated with non-targeting control. An AR signature was generated using MDA-PCa-2b cells treated with 10 nM DHT, in technical triplicates.

Analysis of Agilent 44k microarrays was carried out using limma and included background subtraction (bc.method="half", offset=100) and within-array normalization (method="loess"). Between array quantile normalization of average expression levels (but not log-fold changes) was performed using the function normalizeBetweenArrays (method="Aquantile"). Control probes and probes with missing values were excluded from further analyses. Probes were annotated to Gencode v22 genes using the mapping downloaded from Ensembl (efg_agilent_wholegenome_4x44k_v2). Probes originally annotated as AK093002 were used to detect ARlnc1. Differentially-expressed genes following ARlnc1 knock-down in MDA-PCA-2b cells were identified from triplicate biological repeats using adj.P.Val<0.1 and absolute log fold-change>0.6 cut-offs. Consensus targets of ARlnc1 knockdown using siRNA and ASOs were identified using a merged linear model (all 10 samples treated replicates) and a P value<0.001 cut-off.

Gene Set Enrichment Analysis.

Enrichment analyses for custom and experimentally-derived signatures (i.e. AR targets, genes up- and down-regulated following DHT treatment) were carried out using the nonparametric GSEA software with all default settings. For Gene Ontology (GO) term enrichment, we applied the parametric randomSet[66] enrichment statistic to voom-limma estimated fold-changes (see above).

Overexpression of ARlnc1.

Full-length ARlnc1 was amplified from MDA-PCa-2b cells and cloned into the pCDH clone and expression vector (System Biosciences). Insert sequences were validated by Sanger sequencing at the University of Michigan Sequencing Core. Full-length ARlnc1 sequence is listed in Table 2.

Single Molecule Fluorescent In Situ Hybridization (smFISH).

smFISH and image analysis was performed as described[67,68]. Probe sequences targeting AR, ARlnc1, PCAT1, DANCR, EZH2 and FOXA1 were designed using the probe design software in https://www.biosearchtech.com/stellaris-designer and are listed in Table 3. TERRA probes were designed as described[69]. Other probes were purchased directly from the LGC-Biosearch. U2-OS cells were seeded in 6-well dishes and transfected with ARlnc1 alone or in combination with AR expression vector using Fugene-HD (Promega) according to the manufacturer's protocol. Cells were incubated for 24 hours, reseeded into 8-well chambered coverglasses, and formaldehyde-fixed for smFISH (as described above) after 24 hours. smFISH was carried out according to the above protocol. Number of molecules within large foci was calculated based on the scaled intensity of individual molecules of the appropriate RNA.

RNA In Vitro Transcription.

Linearized DNA templates for full-length ARlnc1, ARlnc1 fragments, ARlnc1 deletion, antisense ARlnc1, LacZ, SCHLAP1-AS, THOR, and AR-3'UTR-1-980 were synthesized using T7-containing primers. Sequences were confirmed by Sanger sequencing at the University of Michigan Sequencing Core. In vitro transcription assays were performed with T7 RNA polymerase (Promega) according to the manufacturer's instructions. For BrU-labeled RNA synthesis, 5-Bromo-UTP was added to the incubation system. At the end of transcription, DNA templates were removed by Turbo DNase (ThermoFisher), and RNA was recovered using RNA Clean and Concentrator Kit (Promega). RNA size and quality was further confirmed by the Agilent Bioanalyzer.

RNA-RNA In Vitro Interaction Assay.

For each interaction assay, 25 µl of Protein A/G Magnetic Beads (Pierce) were washed twice with RIP Wash Buffer (Millipore, Cat #CS203177) before incubating with BrU antibody for one hour at room temperature. After antibody conjugation, beads were washed twice with RIP Wash Buffer and then resuspended in Incubation Buffer containing RIP Wash Buffer, 17.5 mM EDTA (Millipore, Cat #CS203175), and RNase Inhibitor (Millipore, Cat #CS203219). For validation of ARlnc1 and AR 3'UTR binding in vitro, equal amounts (5 pmol) of BrU-labeled RNAs (ARlnc1, ARlnc1-AS, LacZ, SCHLAP1-AS, THOR) were incubated with beads in Incubation Buffer for two hours at 4° C. Following incubation, 2.5 pmol of AR 3'UTR-1-980 RNA fragment was added into individual tubes and incubated overnight at 4° C. After incubation, beads were washed six times with RIP Wash Buffer. To recover RNA, beads were digested with proteinase K buffer containing RIP Wash Buffer, 1% SDS (Millipore, Cat #CS203174), and 1.2 µg/µL proteinase K (Millipore, Cat #CS203218) at 55° C. for 30 minutes with shaking. After digestion, RNA was extracted from supernatant using the miRNeasy kit (QIAGEN), and reverse transcription was performed using the Superscript III system (Invitrogen). The amount of AR 3'UTR-1-980 recovered in each interaction assay was quantified by qPCR analysis. Data were normalized to ARlnc1-AS control, using ΔCt method.

To identify the sites in ARlnc1 that mediate interaction with AR 3'UTR, an RNA-RNA interaction assay was performed following the aforementioned protocol, using BrU-labeled RNAs: ARlnc1, ARlnc1-AS, ARlnc1 fragments (ARlnc1-1-1300, ARlnc1-1301-2786, ARlnc1-1-700, ARlnc1-701-1300), and ARlnc1 deletion (ARlnc1-del-701-1300).

To further validate the interaction, antisense oligos blocking the interaction sites (blocking ASO, Ionis Pharmaceuticals) were used. In-vitro interaction assays between ARlnc1 and AR 3'UTR were performed following the aforementioned protocol, with the addition of control ASO or blocking ASO pool. Data were normalized to the control ASO, using the ΔCt method.

RNA Stability Assay.

LNCaP cells were treated with 5 µg/mL of actinomycin D for various times as indicated in the figure. RNA was extracted at different time points using QIAzol Lysis reagent (QIAGEN) and the miRNeasy kit (QIAGEN). Real-time RT-PCR was carried out as described above. RNA half-life ($t_{1/2}$) was calculated by linear regression analysis (GraphPad Prism® software).

Cell Proliferation Assay.

To test the effects of knocking down ARlnc1 on cell proliferation, MDA-PCa-2b or LNCaP cells were seeded into 24-well plates in quadruplicate and allowed to attach. Cells were then transfected with siRNAs or ASOs using Lipofectamine RNAiMAX. Cell proliferation was determined by IncuCyte live-cell imaging system (Essen Biosciences).

Apoptosis Analysis.

MDA-PCa-2b, LNCa,P and PNT2 cells were grown in 6-well plates and transfected with nonspecific siRNA or siRNAs targeting ARlnc1. Apoptosis analysis was performed 48 hours after transfection, using Dead Cell Apoptosis Kit (Molecular Probes #V13241) according to manufacturer's instructions.

Immunoblot Analysis.

Cells were lysed in RIPA lysis and extraction buffer (Thermo Scientific #89900) supplemented with protease inhibitor cocktail (ROCHE #11836170001). Protein concentrations were quantified using the DC protein assay (BIO-RAD), and protein lysates were boiled in sample buffer. Protein extracts were then loaded and separated on SDS-PAGE gels. Blotting analysis was performed with standard protocols using polyvinylidene difluoride (PVDF) membrane (GE Healthcare). Membranes were blocked for 60 minutes in blocking buffer (5% milk in a solution of 0.1% Tween-20 in Tris-buffered saline (TBS-T)) and then incubated overnight at 4° C. with primary antibody. After three washes with TBS-T, membranes were incubated with HRP-conjugated secondary antibody. Signals were visualized with an enhanced chemiluminescence system as described by the manufacturer (Thermo Scientific Pierce ECL Western Blotting Substrate). Primary antibodies used in this study were: Androgen Receptor (1:1000 dilution, Millipore, #06-680, rabbit), GAPDH (1:5000 dilution, Cell Signaling, #3683, rabbit), PSA (1:5000 dilution, Dako, #A0562, rabbit), and cleaved PARP (1:1000 dilution, Cell Signaling, #9542, rabbit)

Androgen Receptor Reporter Gene Assay.

Dual luciferase reporter assays were performed using Cignal Androgen Receptor Reporter Kit (Qiagen) according to the manufacturer's instructions. Briefly, MDA-PCa-2b cells and LNCaP cells were co-transfected with siRNAs (nonspecific, targeting AR or ARlnc1) and reporter vectors (negative control or AR reporter), using Lipofectamine 2000 transfection reagent (Thermo Fisher Scientific). 40 hours after transfection, DHT (or ethanol vehicle control) was added to induce AR signaling. The Dual Luciferase assay was conducted eight hours after DHT stimulation, using the Dual Luciferase Reporter Assay System from Promega (Cat #1910). Reporter activity was analyzed based on ratio of Firefly/*Renilla* to normalize for cell number and transfection efficiency.

In Vivo Experiments.

For tumor generation with shRNA-mediated knockdown, shRNA targeting ARLNC1 was cloned in pSIH1-H1-copGFP-T2A-Puro (System Biosciences). Lentiviral particles were generated at the University of Michigan Vector Core. LNCaP-AR cells were infected with lentivirus expressing ARLNC1 shRNA for 48 hours. Knockdown of ARLNC1 was confirmed by qPCR analysis. Male athymic nude mice were randomized into two groups at six to eight weeks of age. 5 million cells expressing sh-ARLNC1 or sh-vector were injected into bilateral flanks of mice. Caliper measurements were taken in two dimensions twice a week by an investigator blinded to the study objective and used to calculate tumor volume. The study was terminated when the tumor volume reached 1000 mm$^3$. For ASO treatment in vivo, six to eight week old male athymic nude mice were inoculated subcutaneously with MDA-PCa-2b cells suspended in matrigel scaffold in the posterior dorsal flank region (5 million cells/site, two sites/animal). When the mean tumor volume reached approximately 150 mm$^3$, mice were randomized into two groups, respectively treated with ARLNC1-specific or control ASO. ASOs, dosed 50 mg/kg, were subcutaneously injected between the scapulae once daily for three periods of five days on/two days off. Tumor size was measured twice per week using a digital caliper by a researcher blinded to the study design. Mouse body weights were monitored throughout the dosing period. When average tumor size in the control group reached 1500 mm$^3$, mice were sacrificed and the primary tumors were excised for weight determination. One-third of the resected specimen was placed in 10% formalin buffer, and the remaining tissue was snap frozen.

BrU-Seq and BrUChase-Seq.

BrU-seq and BrUChase-seq assays were performed as previously described[65,66] with MDA-PCa-2b cells treated with either siNT or siARlnc1 BrU-labeling was performed for 30 minutes, and chase experiments were performed for 6 h.

Statistical Analysis.

Statistical analysis was performed using Graphpad Prism 6 software. Data were presented as means±s.e.m. All experimental assays were performed in triplicate unless otherwise specified. Statistical analyses shown in figures represent two-tailed t-tests, one-way ANOVA, two-way ANOVA or Kruskal-Wallis rank sum test, as indicated. $p<0.05$ were considered significant. Details regarding the statistical methods employed during microarray, RNA-Seq and ChIP-Seq data analysis were included in aforementioned methods for bioinformatic analyses.

Data Availability.

RNA-seq and Microarray data will be deposited into Gene Expression Omnibus upon manuscript acceptance.

Results

Analysis of Androgen Receptor-Regulated Transcriptome in Prostate Cancer

To nominate AR-regulated genes (ARGs), RNA-Seq was performed on AR-dependent VCaP and LNCaP prostate cancer cell lines, stimulated with an AR ligand, dihydrotestosterone (DHT), for six and 24 hours (FIG. 9a). 1702 genes were identified that were concordantly induced or repressed in VCaP and LNCaP at both time points (FIG. 1a, FIG. 9b-c), including over 500 lncRNAs (FIG. 1a, FIG. 9d); these data indicate that a large portion of the AR transcriptome remains uncharacterized, specifically considering that the molecular heterogeneity of prostate cancer cannot be fully reflected by a small number of cell lines.

Figure 9:
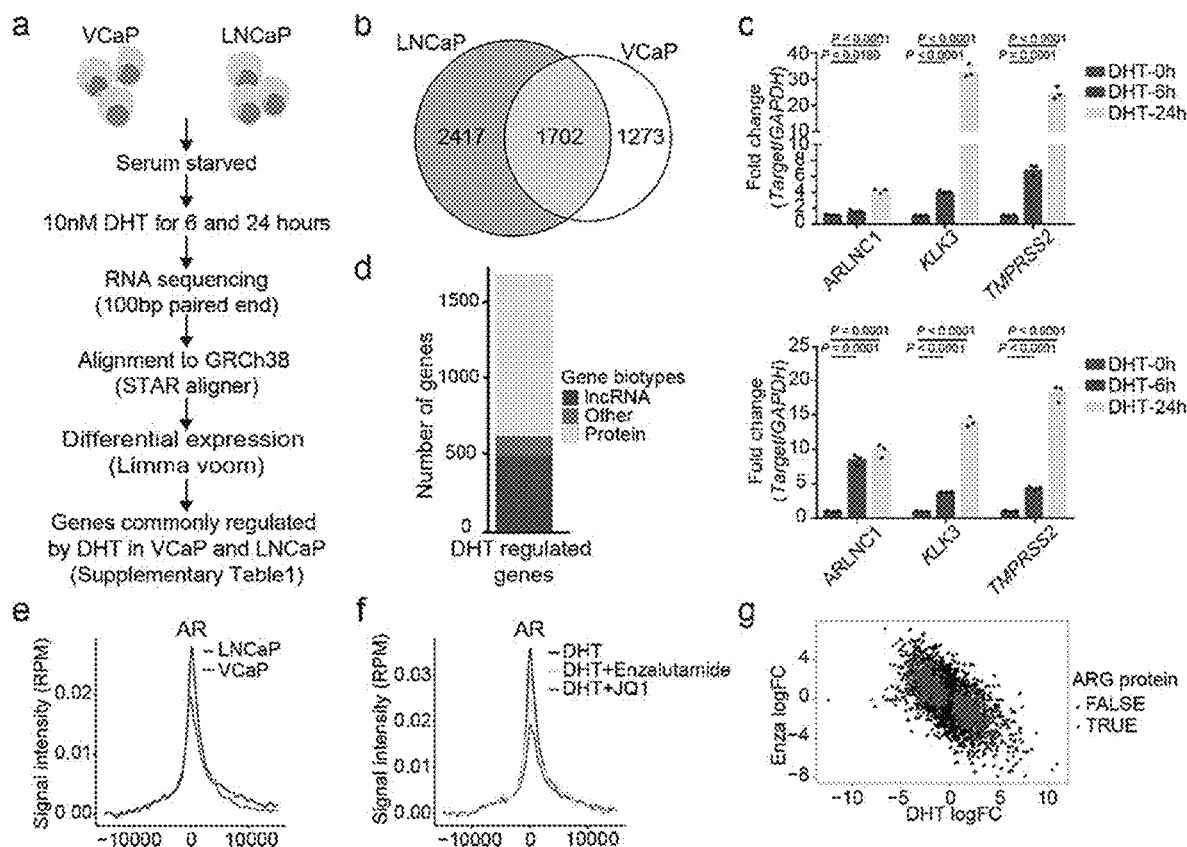
FIG. 9 shows landscape of AR-regulated transcriptome in prostate cancer. (a) A schematic illustration of the procedure used to discover AR-regulated genes (ARGs) in LNCaP and VCaP prostate cancer cell lines. (b) Venn diagram indicating the overlap between AR-regulated genes in LNCaP and VCaP cells. (c) qPCR analysis of ARLNC1 expression and AR signaling gene (KLK3, TMPRSS2) expression in LNCaP cells (top panel) and VCaP cells (bottom panel), following DHT treatment of 6 hours or 24 hours. (d) Bar plot depicting the distribution of gene biotypes (protein, lncRNA, and other) of all overlapped ARGs identified in both LNCaP and VCaP cells. (e) Aggregate ChIP-Seq enrichment profile depicting AR ChIP-Seq signaling density on ARG promoters in LNCaP and VCaP cells. (f) Aggregate ChIP-Seq enrichment profile illustrating AR ChIP-Seq signaling density on ARG promoters in LNCaP cells following DHT stimulation, AR antagonist (enzalutamide) treatment, or BRD4 inhibitor (JQ1) treatment. (g) Transcriptional response to DHT and enzalutamide treatment in VCaP cells, plotting AR regulated protein-coding genes (top panel), or AR regulated lncRNAs (bottom panel). (h) Motif discovery analysis of the top 250 AR ChIP-Seq peaks on AR promoters identifies a binding motif similar to the canonical AR response element. (i) Aggregated ChIPSeq enrichment profiles depicting ChIP-Seq signal density on direct ARG promoters for H3K27ac, H3K4me1, H3K4me3, H3K36me3, Pol II, and BRD4 in LNCaP cells. (j) Pie chart showing prostate cell line or tissue distribution of direct ARGs with AR binding at transcription start sites (TSS) in ChIP-Seq. (k-l) Cumulative distribution plots of distances between transcription start sites (TSS) of genes to nearest AR peak. (k) AR binding near ARGs in benign prostate, prostate cancer tissues (PCa), and prostate cell lines. (l) Comparison of distances between AR binding sites for ARGs and genes not regulated by AR.
Figure 9:
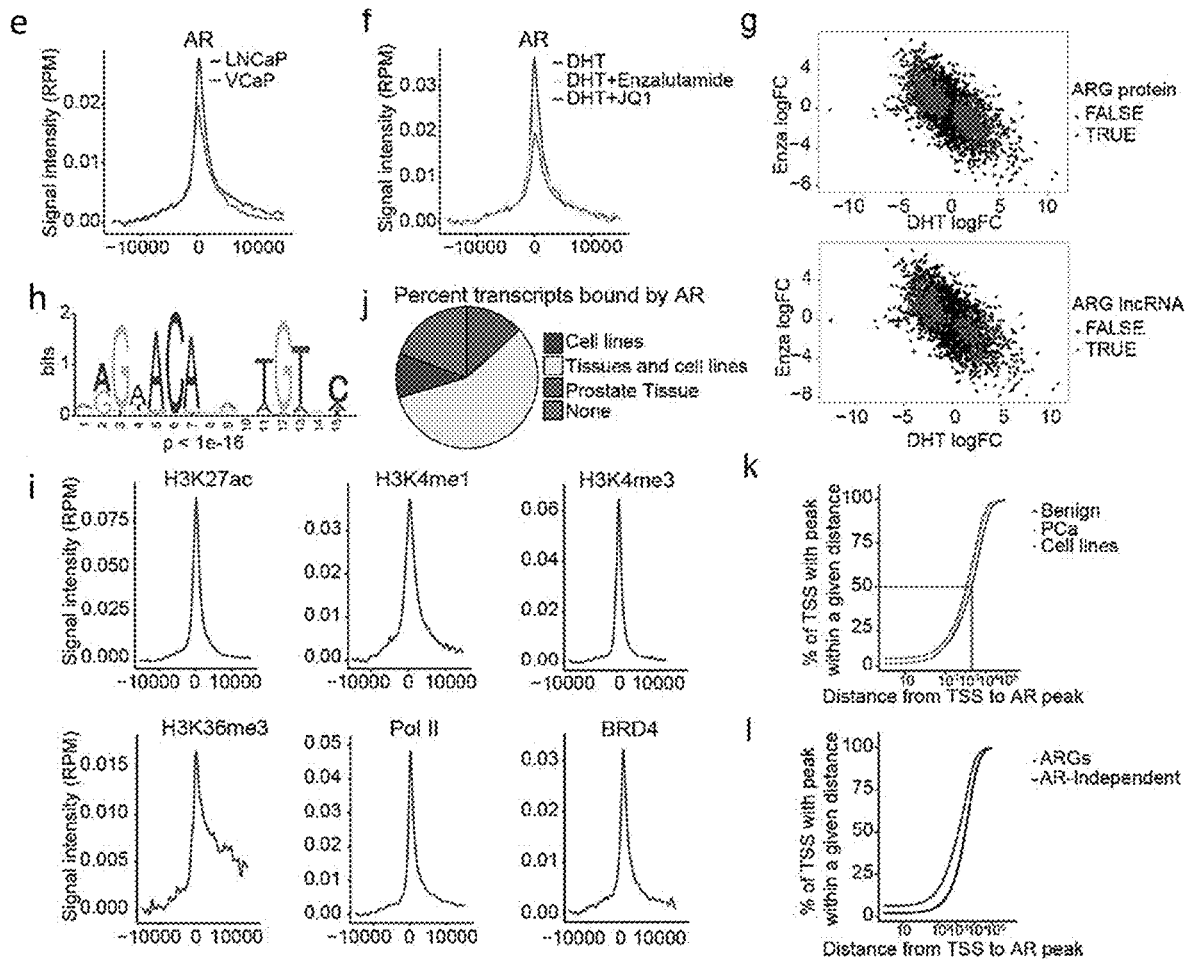

To differentiate between direct and indirect ARGs, previously published AR chromatin immunoprecipitation (ChIP)-Seq data from LNCaP and VCaP cells were analyzed[32]. For direct AR targets, increased levels of AR binding at transcription start sites (TSS) in both LNCaP and VCaP cells was observed (FIG. 9e). The binding levels were decreased following treatment with an AR antagonist (enzalutamide) (FIG. 9f), and the binding sites revealed a de novo motif identical to the canonical AR response element[33] (FIG. 9h). A total of 987 genes were categorized as direct ARGs, including 341 lncRNAs (lncARG). Within these genes, an enrichment of chromatin marks associated with "open" chromatin (H3K27ac, H3K4me1), active promoters (H3K4me3), and transcription (H3K36me3) was observed, which together with Pol-II occupancy are recognized as manifestations of active gene expression (FIG. 9i). BET family proteins, such as BRD4, recognize acetylated histones and have been shown to promote AR transcriptional activity[32]. Consistently, the co-localization of BRD4 and AR at promoters of direct AR responsive genes and the loss of AR following treatment with a bromodomain inhibitor (JQ1) was observed (FIG. 9f, i). It was determined whether ARGs identified from cell lines were also targeted by AR in normal prostate tissues and primary tumors. The dataset from Pomerantz et. al was queried for the presence of AR peaks within ARG promoters[34]. Remarkably, the majority of ARG promoters were TSS-proximally bound by AR in both tissues and cell lines (FIG. 9j,k); conversely, AR-independent genes were distal to AR binding sites (FIG. 9l).

Figure 1:
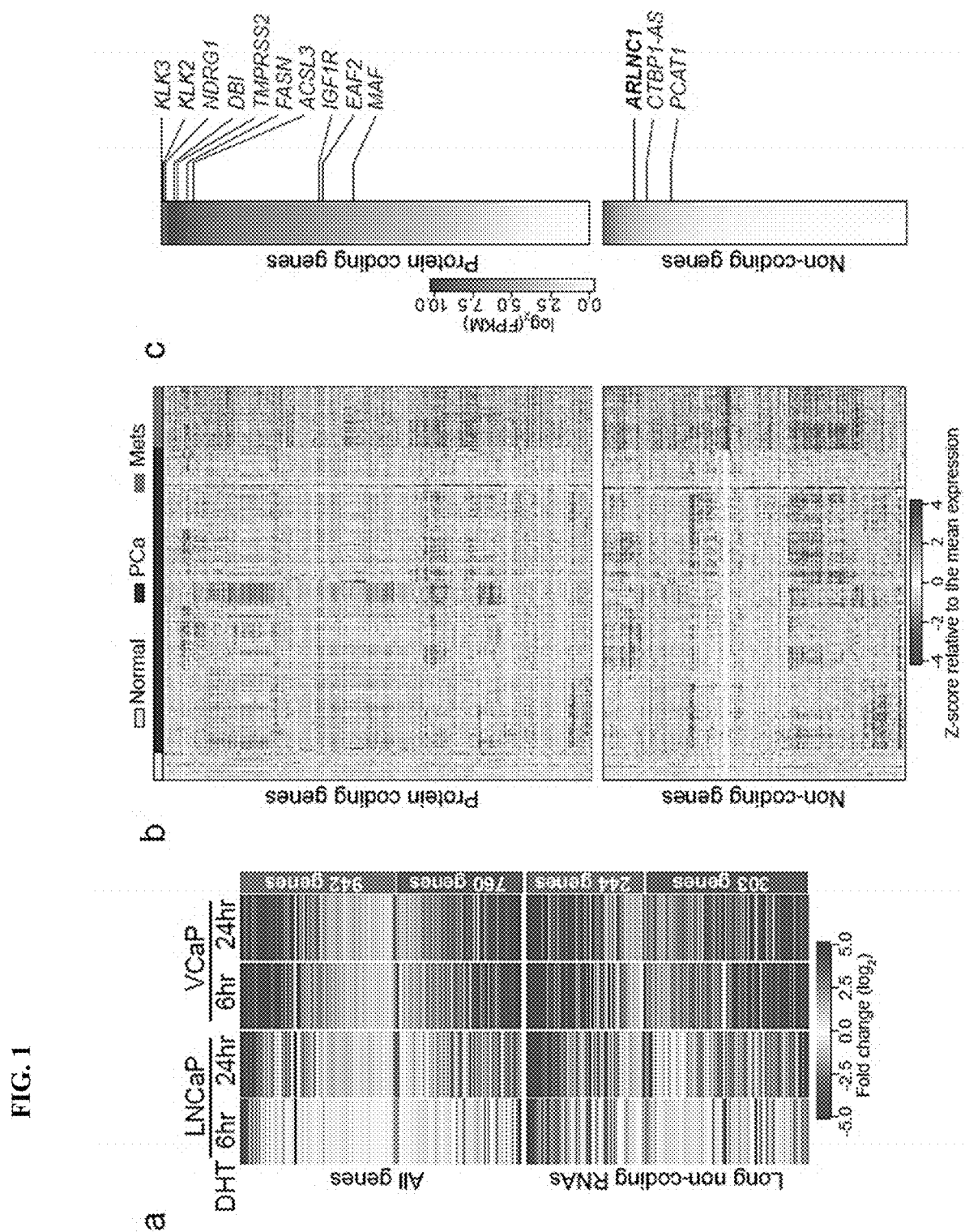
FIG. 1 shows identification of AR regulated genes in prostate cancer. a, The androgen-regulated transcriptome of prostate cancer cells. b, The landscape of transcriptomic alterations of prostate cancer progression. c, A heatmap representation of ranked gene expression levels in prostate tissues.

Finally, it was confirmed that the AR-regulated genes were also expressed in human prostate tissues. RNA-Seq data from normal prostate, clinically-localized PCa (The Cancer Genome Atlas, TCGA)[35], and metastatic CRPC (Stand Up to Cancer-Prostate Cancer Foundation, SU2C-PCF)[35] were interrogated (FIG. 1b). This revealed remarkable heterogeneity in the expression of ARGs during prostate cancer progression to metastatic disease. Compared to protein-coding genes, non-coding ARGs were detected at lower overall levels (FIG. 1c), although ~10% of them showed robust expression of over 10 FPKM on average across prostate cancer samples.

ARLNC1 is a Prostate Lineage-Specific lncRNA with Elevated Expression in Cancer

Figure 2:
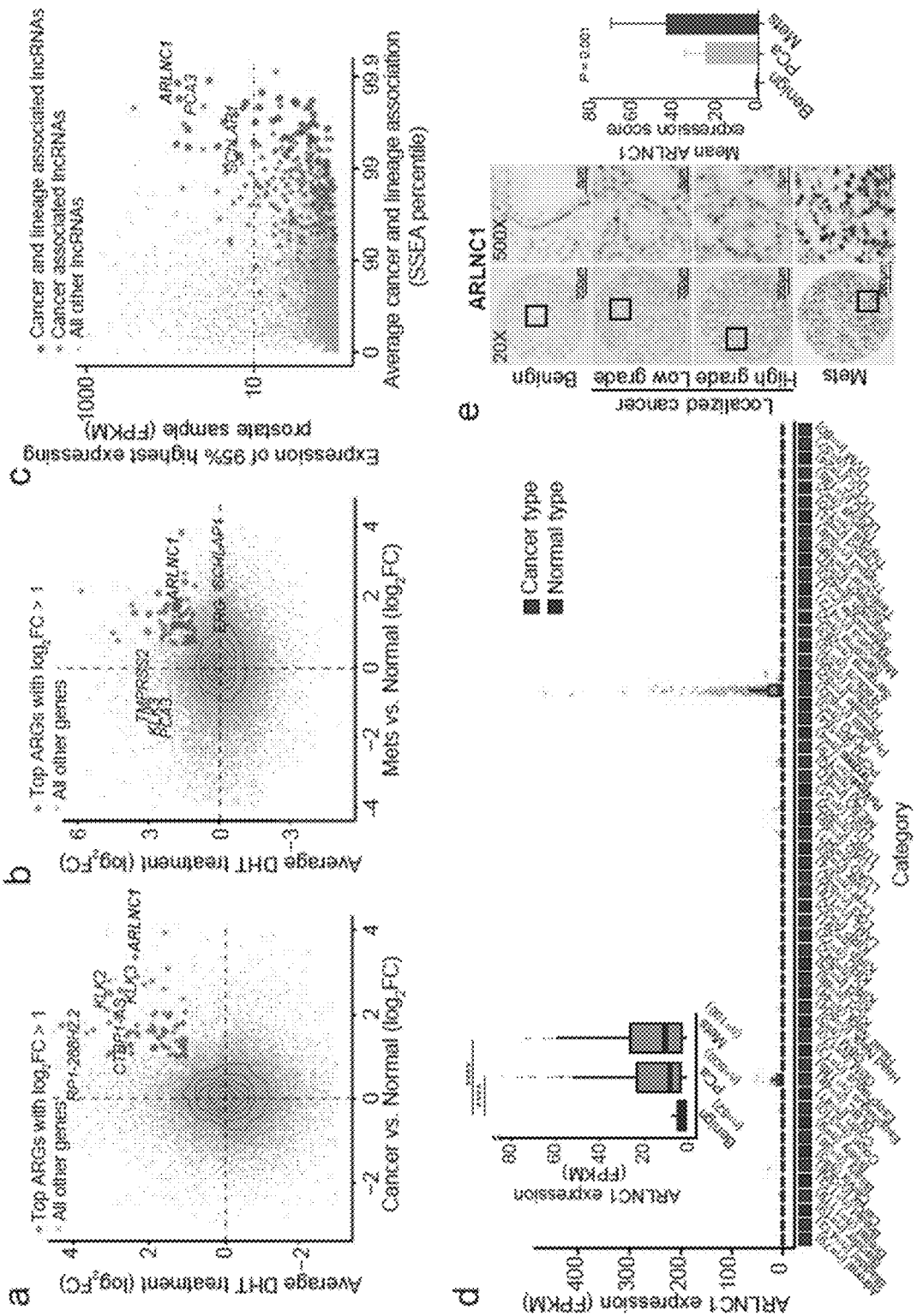
FIG. 2 shows nomination and in situ characterization of ARLNC1 in prostate cancer. a-b, Identification of androgen-regulated transcripts elevated in prostate cancer progression. Y-axis depicts log 2-fold change of gene expression upon DHT stimulation, and x-axis indicates log 2-gene expression level difference between benign (n=52 samples) and localized prostate cancer (n=500 samples) (a), or expression level differences between benign (n=52 samples) and metastatic prostate cancer (n=100 samples) (b). c, Nomination of prostate cancer- and lineage-associated lncRNAs based on expression levels. d, Relative expression (FPKM) of ARLNC1 across different cancer types in the TCGA cohort. Inset: relative expression (FPKM) of ARLNC1 across benign (n=52 samples), localized (n=500 samples), and metastatic (n=100 samples) prostate cancer. e, In situ hybridization of ARLNC1 in human prostate cancer tissue microarray.

It was hypothesized that lncRNAs associated with PCa progression and castration-resistance should either be upregulated if they enhance AR signaling or, conversely, downregulated if they attenuate AR signaling. Their expression is also expected to be AR-dependent and lineage-restricted if they are part of bona fide physiological feedback loops. Accordingly, a top-down strategy was developed in order to establish and prioritize clinically-relevant, prostate cancer and lineage-specific lncARGs. First, genes were identified that were both directly regulated by AR in VCaP/LNCaP cell lines and upregulated in primary (FIG. 2a) or metastatic cancer (FIG. 2b) compared to normal tissue. Canonical AR targets, including KLK3, KLK2, and TMPRSS2, were among the most differentially expressed protein coding genes. Importantly, this approach highlighted several novel lncARGs, including ARlnc1 (ENSG00000260896, PRCAT47[10]), and validated previously identified lncARGs, such as CTBP1-AS[36] (FIG. 2a-b). ARlnc1 was found to be one of the most differentially expressed AR-regulated genes in both localized and metastatic PCa (FIG. 2a-b, FIG. 10a-b).

Next, the prostate lineage and cancer specificity of prostate cancer-associated lncRNAs was identified by leveraging the MiTranscriptome assembly[10], an online resource to interrogate lncRNA expression across a multitude of tissue and tumor types, and Sample Set Enrichment Analysis (SSEA), which indicates the strength of cancer and lineage association[10]. After applying an expression level filter (10 FPKM at the 95th percentile), 12 of the most prostate lineage and prostate cancer-specific lncRNAs were identified (FIG. 2c, FIG. 10c-d); five of these lncRNAs were regulated by AR. Across these analyses, ARlnc1 was the top prioritized transcript, warranting further investigation.

Figure 10:
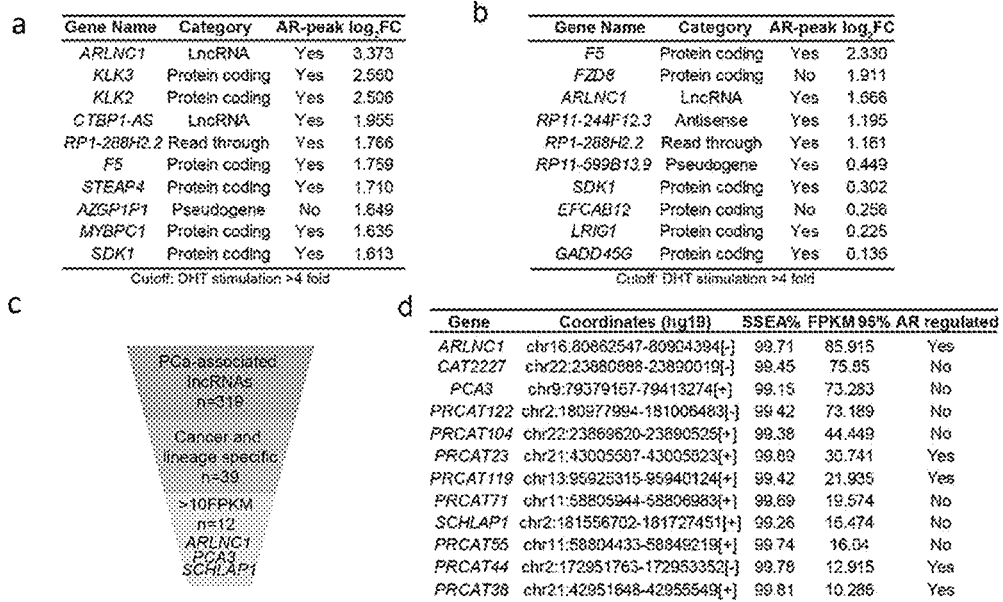
FIG. 10 shows that ARLNC1 is prioritized as a lineage-specific, cancer-associated lncRNA in prostate cancer. (a) The top ten AR-regulated, localized prostate cancer-associated genes identified in FIG. 2a, after applying an expression filter of at least four fold change (log 2FC=2) upon DHT stimulation and at least 1 FPKM average expression in prostate cancer tissues. (b) The top ten AR-regulated, metastatic prostate cancer-associated genes identified in FIG. 2b, after applying an expression filter of at least four fold change (log 2FC=2) upon DHT stimulation and at least 1 FPKM average expression in prostate cancer tissues. (c) Schematic illustration of the procedure used to nominate prostate lineage-specific, cancer-associated lncRNAs in prostate cancer. (d) The top twelve prostate tissue-specific, prostate cancer-associated lncRNAs identified in FIG. 2c, after applying an expression filter of at least 10 FPKM in the prostate samples in the top 5% based on gene expression level (n=7,256 samples). (e) Relative expression (FPKM) of ARLNC1 across a panel of normal tissues in GTEx normal tissue RNA-seq cohort (n=9,435 samples) (f) Tissue and cancer-specific expression of ARLNC1 according to MiTranscriptome. (g) Oncomine concepts analysis of genes positively (top panel) or negatively (bottom panel) correlated with ARLNC1.
Figure 10:
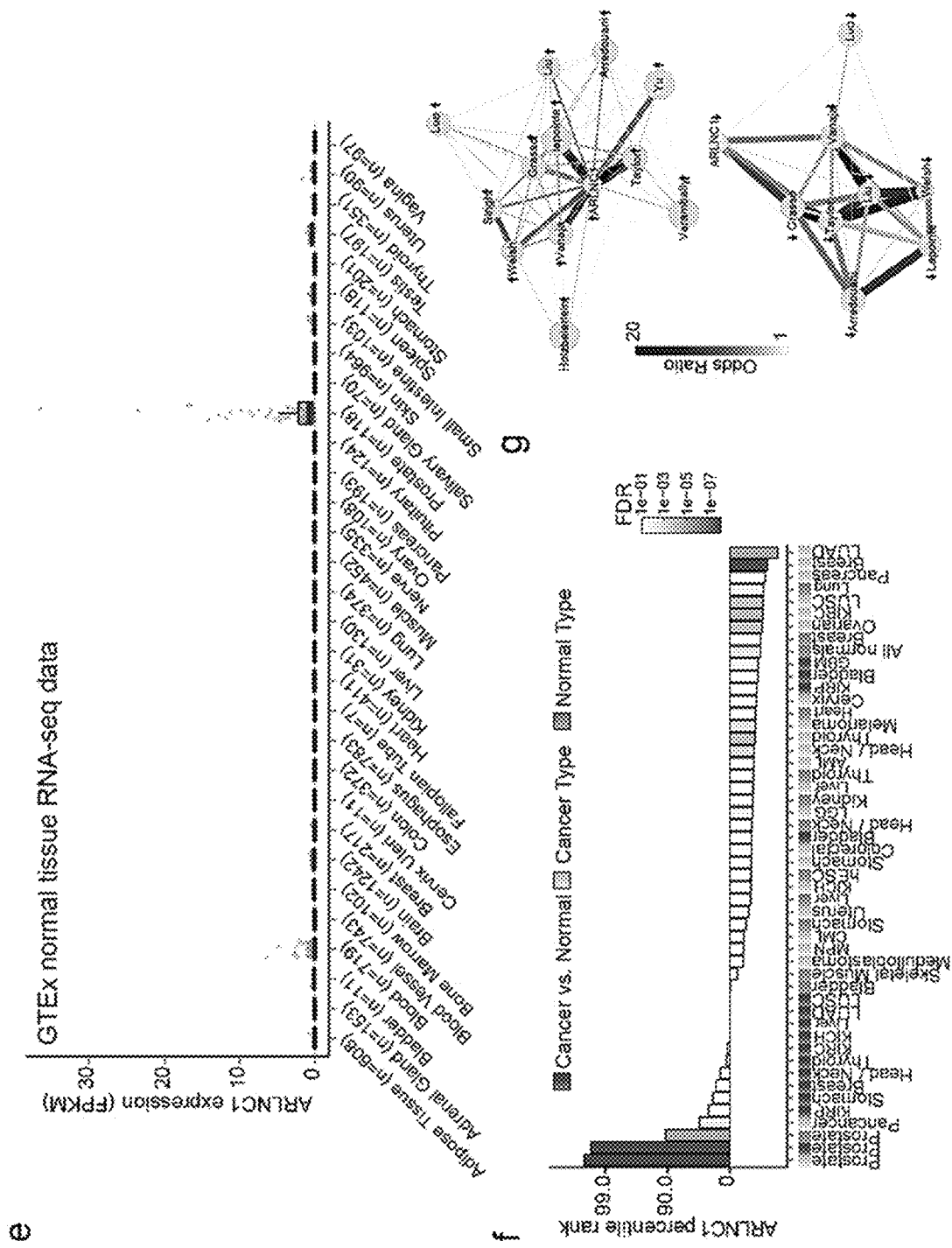
Figure 11:
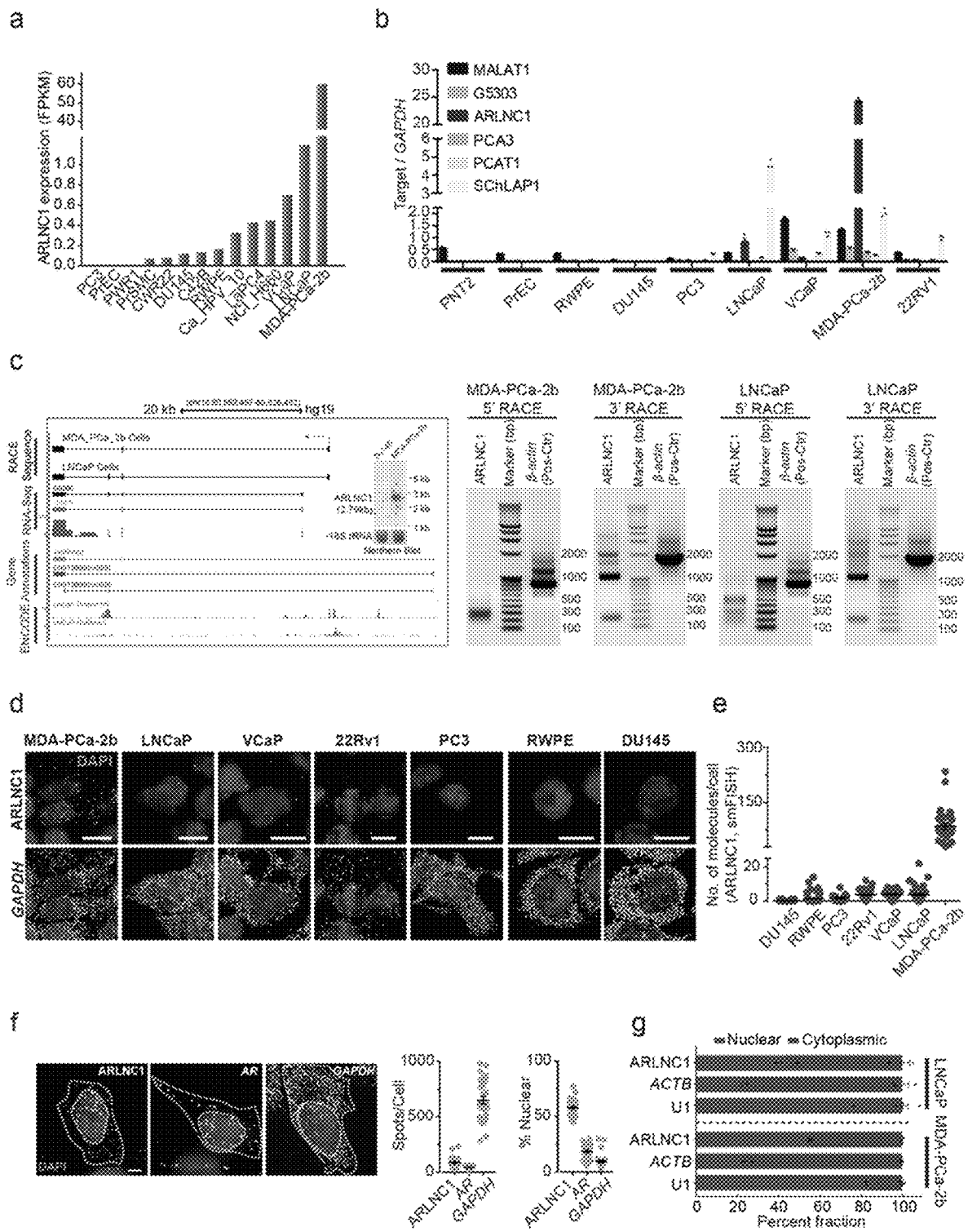
FIG. 11 shows characterization of ARLNC1 and its expression. (a) Relative expression of ARLNC1 (FPKM) across 14 prostate cancer cell lines. (b) qPCR analysis of ARLNC1 expression in nine prostate cancer cell lines. (c) Left: Representative image of ARLNC1 gene structure in MDA-PCa-2b and LNCaP cells, generated from RACE analysis. (d) smFISH images depicting localization of ARLNC1 transcripts in a panel of prostate cancer cell lines.

Expression of ARlnc1 was interrogated across cancer and normal tissue RNA-Seq samples from TCGA and the Genotype-Tissue Expression (GTEX) project[37,38], respectively. In the TCGA cohort, ARlnc1 exhibited a highly prostate cancer-specific expression pattern, with little to no expression in other tumor types (FIG. 2d). Similarly, in the GTEX normal tissue cohort, its expression was limited to the prostate (FIG. 10e). Within prostate tissue, ARlnc1 expression, as assessed by RNA-Seq and in situ hybridization was significantly higher in localized and metastatic prostate cancers compared to benign tissues (FIG. 2d inset, FIG. 2e). In an extensive differential expression analysis using MiTranscriptome, ARlnc1 was found to be among the top 1% of genes most unregulated in prostate cancer and specific to the prostate lineage, with no significant associations in other tissues (FIG. 10f). Additionally, the protein-coding genes that were most correlated with ARlnc1 were found to be associated with prostate cancer progression in multiple ONCOMINE clinical datasets' (FIG. 10g). Together, these results confirm that ARlnc1 expression is restricted to prostate cancer and associated with AR signaling throughout prostate cancer progression. To functionally characterize ARlnc1, appropriate prostate cancer cell lines with moderate to high levels of ARlnc1 expression were identified using in house RNA-Seq data (FIG. 11a). Supporting the association of AR with ARlnc1, ARlnc1 expression was highly enriched in AR-positive cell lines, with the highest expression in MDA-PCa-2b and LNCaP cells. In addition, qPCR analysis for the ARLNC1 transcript also demonstrated that this gene was expressed highest in MDA-PCa-2b and LNCaP cell lines (FIG. 11b). According to existing annotations, ARlnc1 is located on chromosome 16 and has several isoforms that differ in exon and TSS usage. Random amplification of cDNA ends (RACE) was performed in MDA-PCa-2b and LNCaP cells to determine the exact structure of ARlnc1. A dominant TSS for ARlnc1 was found MDA-PCa-2b cells, and the 2.8 kb ARlnc1 isoform was further confirmed by northern blot analysis (FIG. 11c). Single molecule fluorescent in situ hybridization (smFISH) revealed approximately 100 molecules of ARlnc1 transcripts existed per MDA-PCa-2b cell (FIG. 11d-e). Using smFISH and qPCR, it was also found that ARLNC1 molecules were distributed equally between the nuclear and cytoplasmic cellular compartments (FIG. 11f-g).

ARLNC1 Transcription is Directly Regulated by AR

Figure 3:
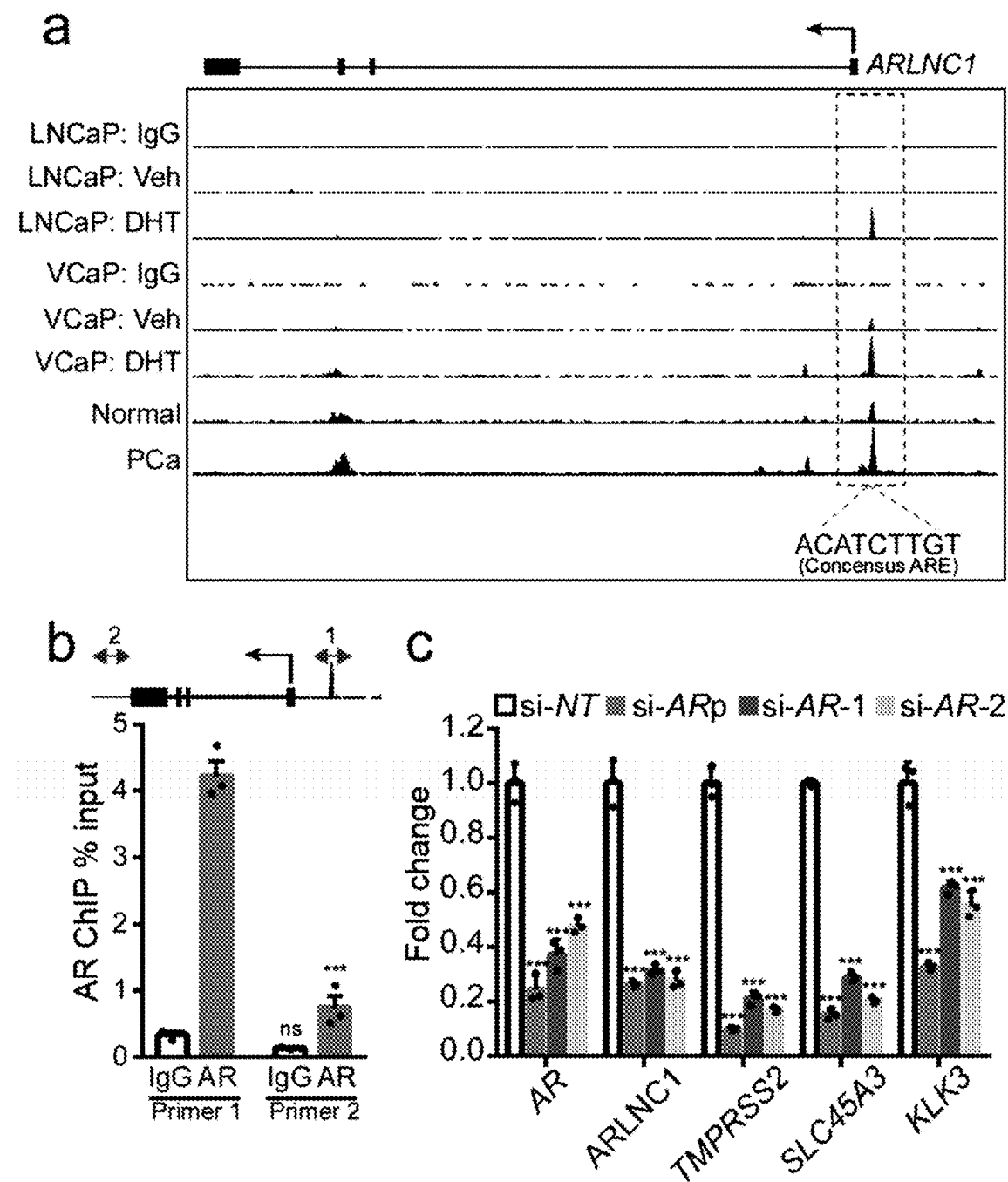
FIG. 3 shows that ARLNC1 is directly regulated by AR. a, AR ChIP-Seq in prostate cancer cell lines and tissues. Top, AR or control (IgG) ChIP-Seq results across the ARLNC1 locus in LNCaP and VCaP cells with vehicle (ethanol) treatment or DHT treatment. Bottom, AR ChIP-Seq in benign prostate and clinically-localized prostate cancer tissue. b, ChIP-qPCR in MDA-PCa-2b cells showing AR or IgG enrichment (ChIP/input) over ARLNC1 promoter region (Primer 1) or control region (Primer 2). Top: schematic of amplicon locations for ChIP-qPCR validation. c, AR and AR target gene (ARLNC1, TMPRSS2, SLC45A3, and KLK3) expression in MDA-PCa-2b cells transfected with control siRNA (si-NT) or siRNAs against AR (si-AR-pool, si-AR-1, si-AR-2).

Since ARlnc1 was identified as an AR-regulated lncRNA, AR ChIP-Seq data from DHT-stimulated VCaP and LNCaP cells was interrogated for AR binding sites. An androgen-induced AR peak directly at the annotated promoter of ARlnc1 was identified in both VCaP and LNCaP cells (FIG. 3a). This AR binding site was also observed in prostate tissue samples and contained a canonical AR binding motif (ARE)[33] (FIG. 3a). These observations were corroborated in MDA-PCa-2b cells, which showed the highest level of ARlnc1 expression, by ChIP-qPCR (FIG. 3b). Considering the observation that ARlnc1 expression is prostate tissue-specific, while AR expression is not as much, other transcription factors and epigenetic modifiers that control ARlnc1 expression were identified (FIG. 12a). Motif analysis of ARlnc1 promoter region identifies several transcription factor binding motifs, including a FOXA1-responsive motif. To further validate ARLNC1 gene regulation by AR and FOXA1, ARLNC1 transcript levels were evaluated following AR or FOXA1 knockdown. AR or FOXA1 loss resulted in decreased expression of ARLNC1, along with other canonical AR target genes that served as positive controls (FIG. 3c, FIG. 12b). ChIP-seq and ChIP-PCR analysis additionally confirmed the putative FOXA1 binding motif on the ARLNC1 promoter (FIG. 12c). Together, these observations indicate that ARLNC1 is directly regulated by AR and modestly regulated by FOXA1, which, partially explains the tissue-specific expression pattern of ARLNC1, as expression of these two factors overlaps nearly exclusively in prostate tissue[37,38] (FIG. 12d).

ARLNC1 Regulates AR Signaling

Figure 4:
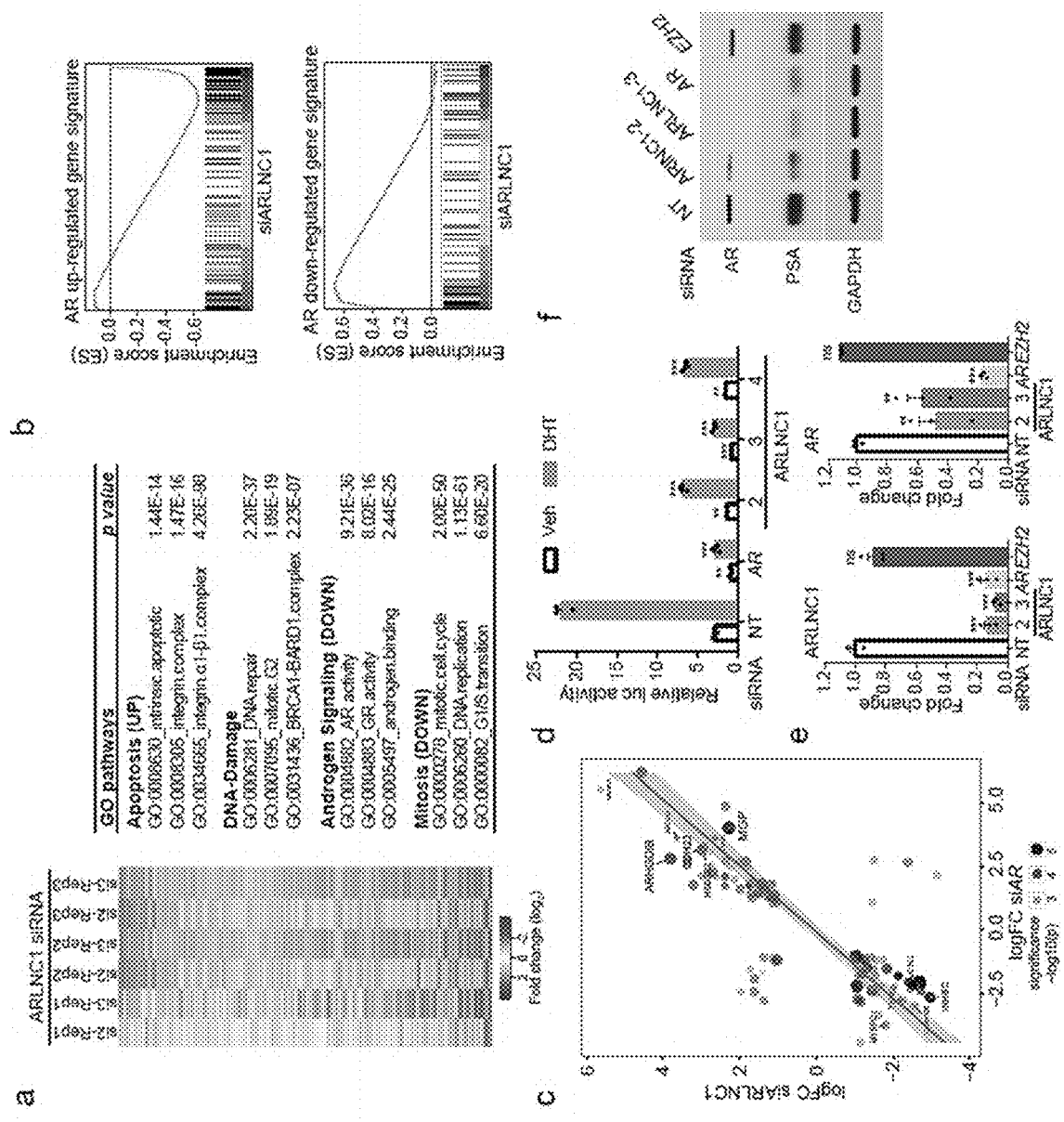
FIG. 4 shows that ARLNC1 loss attenuates AR signaling. a, Gene expression profiling for ARLNC1 knockdown in MDA-PCa-2b cells (n=3 biologically independent cell cultures for each siRNA). b, Gene Set Enrichment Analysis (GSEA) showing significant enrichment of ARLNC1-regulated gene set with respect to the AR target gene sets (n=3 independent gene expression profiles). c, Comparison of ARLNC1-regulated and AR target genes based on RNA-seq following knockdown of AR and ARLNC1. d, siRNA knockdown of ARLNC1 in MDA-PCa-2b cells impairs AR signaling by AR reporter gene assay. e, qRT-PCR analysis of ARLNC1 and AR in MDA-PCa-2b cells transfected with siRNAs against ARLNC1, AR, EZH2, or non-specific control (NT). f, Immunoblot of AR, PSA, and GAPDH in MDA-PCa-2b cells transfected with siRNAs against ARLNC1, AR, EZH2, or non-specific control (NT).

To determine the function of ARlnc1 in prostate cancer, gene expression profiling of MDA-PCa-2b cells transfected with siRNAs targeting ARlnc1 was performed (FIG. 4a). Enrichment analysis of the gene expression data revealed the deregulation of four main biological activities: apoptosis, cell proliferation, DNA damage response, and androgen signaling (FIG. 4a). A significant decrease in AR target gene expression was particularly interesting given the fact that ARlnc1 is regulated by AR, indicating a positive feedback loop between ARlnc1 and AR signaling. To confirm this observation, an AR target gene signature was generated from MDA-PCa-2b cells stimulated with DHT (FIG. 13a) and GSEA analysis was performed using this gene signature (FIG. 4b). Knockdown of ARlnc1 led to suppression of genes positively regulated by AR and upregulation of genes negatively regulated by AR in MDA-PCa-2b cells (FIG. 4b-c, FIG. 12b). This was further confirmed by AR reporter activity assay (FIG. 4d, FIG. 13c), as well as qPCR analysis of AR target genes (FIG. 13d). ARlnc1 knockdown also had a significant effect on the mRNA and protein levels of AR (FIG. 4e-f), indicating direct regulation of AR by ARlnc1. However, it was found that ARlnc1 overexpression did not have any effect on AR and its signaling cascade (FIG. 13e).

In Situ Co-Localization of ARLNC1 and AR Transcripts

Figure 5:
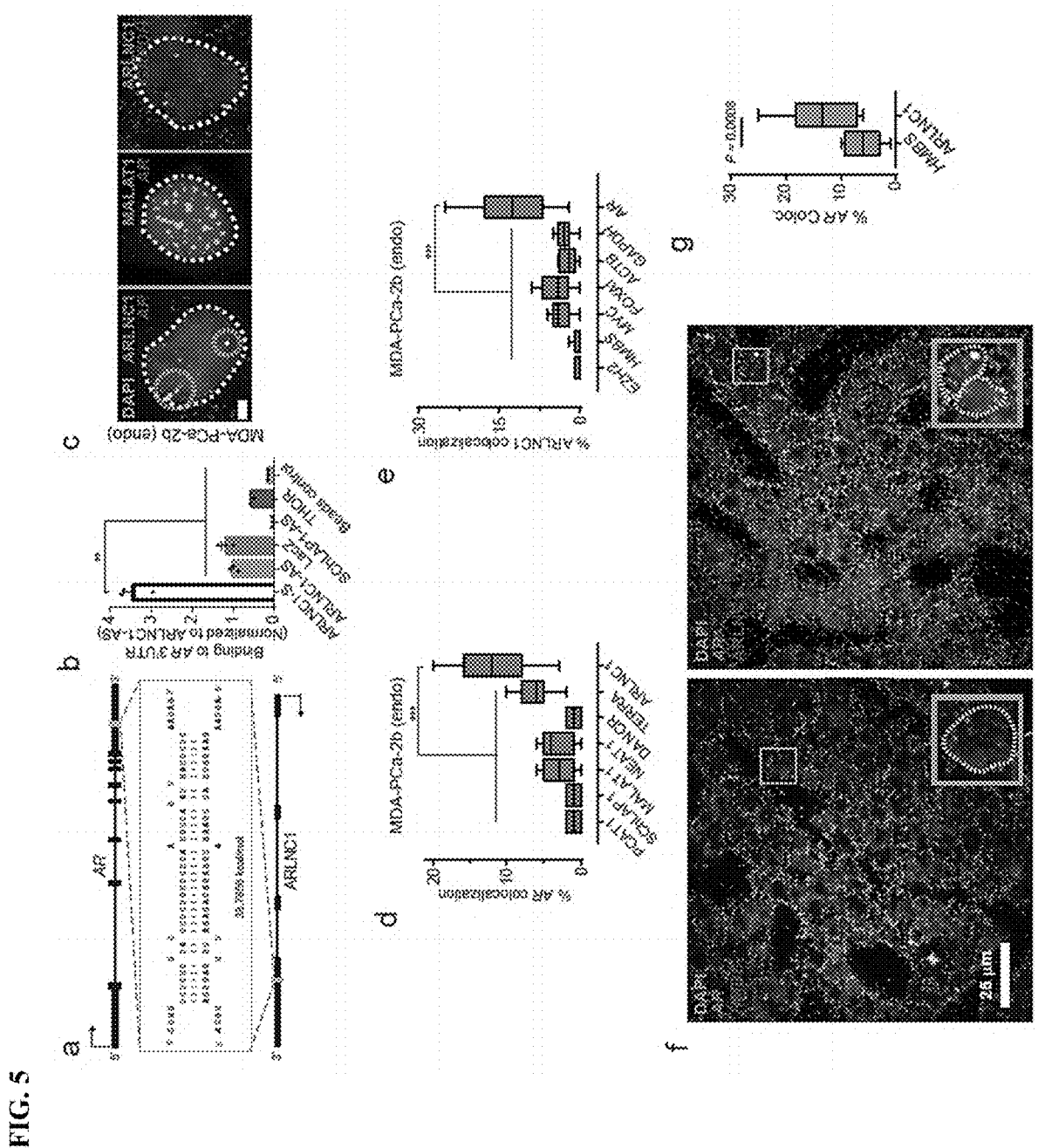
FIG. 5 shows In situ co-localization between AR mRNA and ARLNC1 in prostate cancer cells. a, Schematic of predicted RNA-RNA interaction between ARLNC1 and 3'UTR of AR. b, ARLNC1 interacts with AR 3'UTR in an in vitro RNA-RNA interaction assay. c-e, smFISH depiction of AR-ARLNC1 colocalization in situ. Representative pseudo-colored images of MDA-PCa-2b cell nuclei (c) stained for the appropriate endogenous (endo) transcripts and DAPI (nucleus). Scale bar, 5 µm. Quantification of the percentage of AR or ARLNC1 molecules co-localizing with a panel of lncRNAs (d) or mRNAs (e) respectively. Orange circles represent regions of colocalization. Center line and whiskers depict the median and range respectively and box extends from 25th to 75th percentiles (n=50 cells for each sample aggregated from 3 independent experiments). f-g, Representative pseudo-colored images of ARLNC1 positive prostate cancer tissues (f) stained with DAPI (nucleus) and AR, HMBS, or ARLNC1 transcripts (smFISH). Quantification of the percentage of AR molecules (g) colocalizing with HMBS or ARLNC1 is also depicted in box plot.

Non-coding RNAs have been shown to target mRNAs via direct or indirect RNA-RNA interaction[9, 40, 42]. To identify target mRNAs that could interact with ARlnc1, an unbiased prediction of RNA-RNA interactions was performed using IntraRNA[43, 44]. The 3' UTR of the AR transcript was identified as a target of ARlnc1 (FIG. 5a, FIG. 14a). An in vitro RNA-RNA interaction assay between the 3'UTR of AR and full-length ARlnc1 confirmed this in silico prediction (FIG. 5b). To evaluate this interaction in the context of cellular environment, multiplexed smFISH for AR and ARLNC1 transcripts was performed in MDA-PCa-2b cells. Upon co-staining MDA-PCa-2b cells with AR and a panel of lncRNAs, or ARlnc1 and a panel of mRNAs, specific colocalization was observed between AR and ARlnc1 transcripts in the nucleus within foci that were typically larger than individual molecules (FIG. 5c-e). The extent of colocalization was much higher than that expected from co-incidental colocalization with an abundant transcript, such as MALAT1 or GAPDH (FIG. 5c-e). More specifically, colocalization typically occurred at a stoichiometry of 2:1 ARlnc1:AR, accounting for ~10-20% of all AR and ARlnc1 transcripts in the cell (FIG. 14b). Furthermore, AR-ARlnc1 colocalization is observed in ARlnc1-positive prostate cancer tissues.

Figure 6:
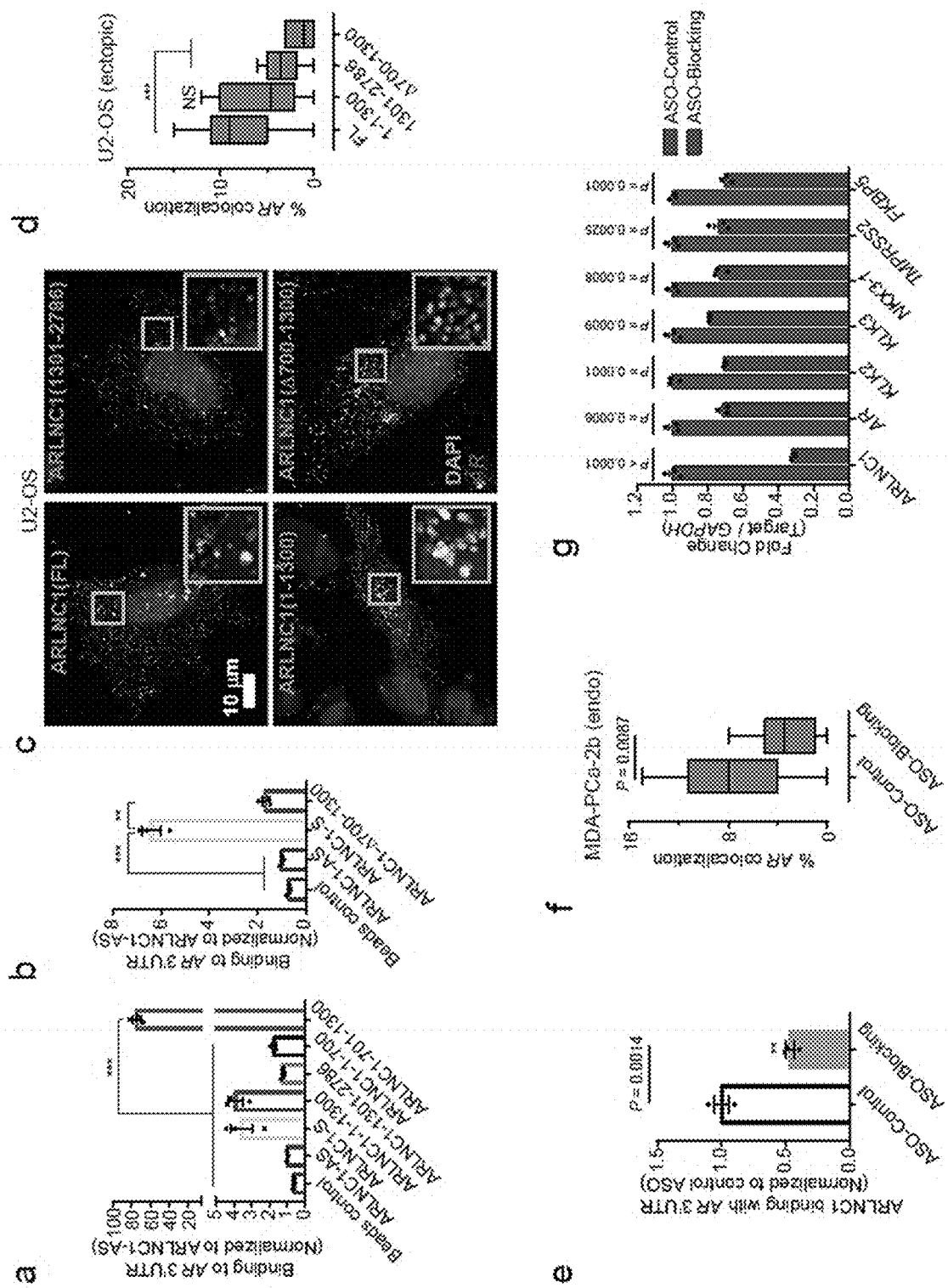
FIG. 6 shows identification of ARLNC1 fragment mediating RNA-RNA interaction with AR mRNA. a, In vitro RNA-RNA interaction assay identifies nucleotides 700-1300 on ARLNC1 as critical binding sites to AR 3'UTR-1-980. b, Deletion of nucleotides 700-1300 on ARLNC1 results in impaired binding to AR 3'UTR, as shown by in vitro RNA-RNA interaction assay. c, Representative pseudo-colored images of U2-OS cells stained for DAPI (nucleus), ARLNC1 and AR transcripts. d, Quantification of the percent of AR molecules colocalizing with various ARLNC1 fragments. e, Antisense oligos targeting sites 700-1300 on ARLNC1 transcript (Blocking ASO pool) inhibit ARLNC1 interaction with AR 3'UTR. f, smFISH shows that ASOs targeting 700-1300 nt on ARLNC1 transcript (ASO-Blocking) inhibit ARLNC1 colocalization with AR in situ.
Figure 7:
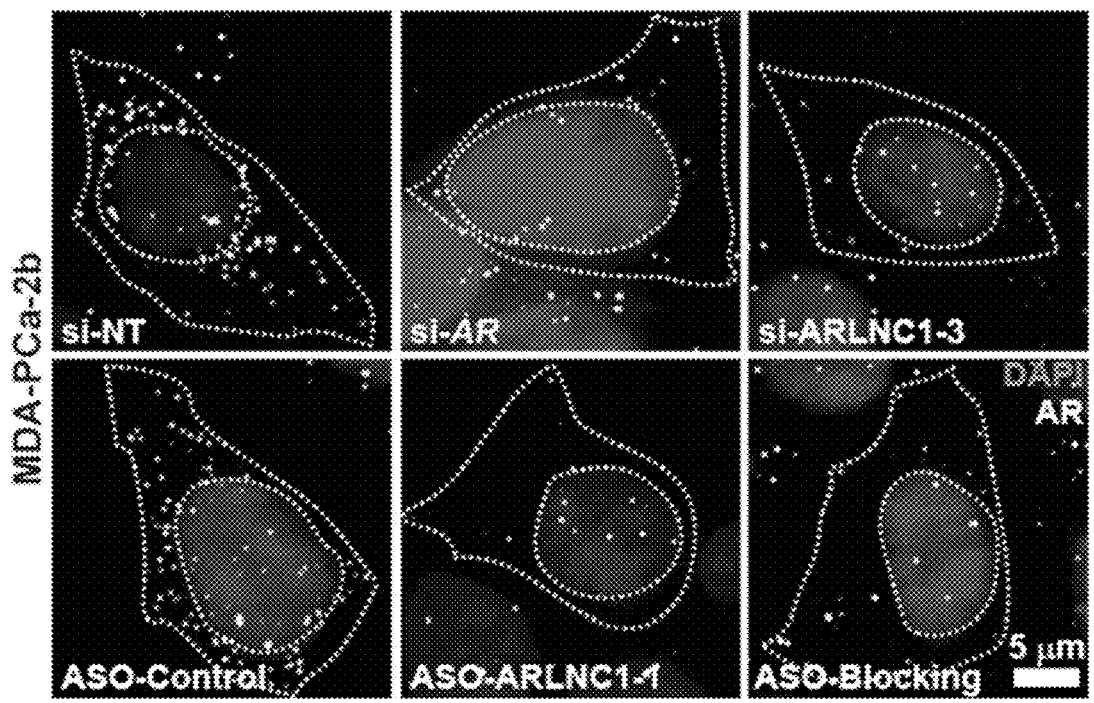
FIG. 7 shows that ARLNC1 regulates cytoplasmic level of AR transcript. a, ARLNC1 regulates AR post-transcriptionally by specifically affecting cytoplasmic AR mRNA. b, Fractional column plots depicting the nucleo-cytoplasmic distribution of AR mRNA after various treatment conditions in (a), as computed using smFISH.
Figure 7:
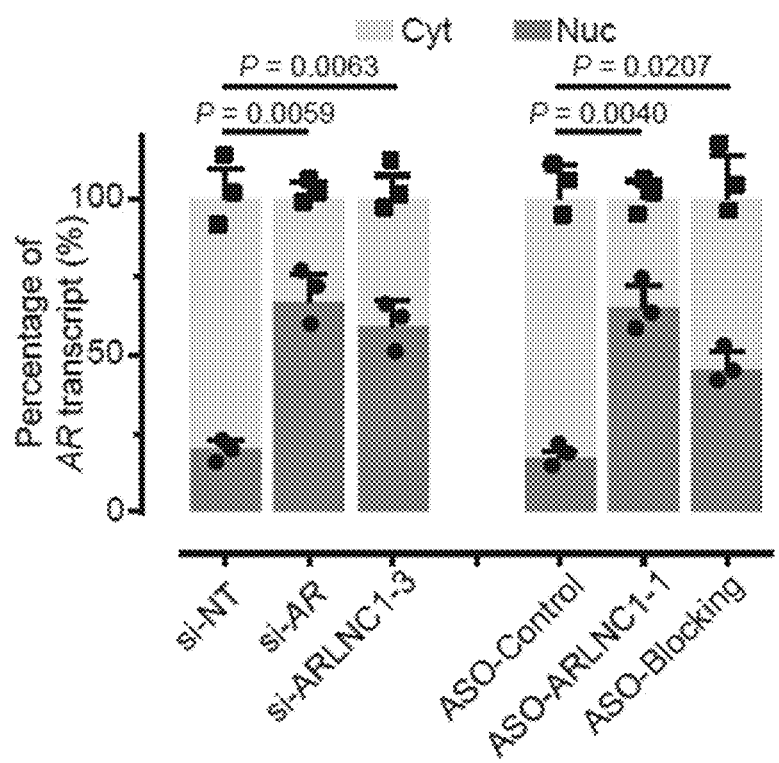

Using in vitro RNA-RNA binding assay, nucleotides (nt) 700-1300 of ARlnc1 were identified as critical for binding to the AR 3'UTR (FIG. 6a-b). To confirm this observation within the cellular context, different fragments of ARlnc1 were ectopically overexpressed together with AR in U2OS osteosarcoma cells, In this exogenous system, colocalization between AR and ARlnc1 was additionally demonstrated, wherein colocalization was dependent on the presence of 700-1300 nt of ARlnc1 (FIG. 6c-d, FIG. 14c). Furthermore, incubation with antisense oligos blocking the interaction site led to a significant reduction in ARlnc1-AR interaction in vitro and in situ (FIG. 6e-f, FIG. 14d-e). Decreased AR signaling was also observed following blocking of this interaction (FIG. 6g, FIG. 14f).

ARLNC1 Regulates the Cytoplasmic Levels of AR Transcripts

The mechanism of ARlnc1-mediated AR regulation was investigated. The stability of these two transcripts was monitor and it was found that AR and ARlnc1 have similar half-lives of approximately 9 hours (FIG. 14g). As ARlnc1 depletion resulted in a striking reduction of AR protein levels, much more than that explained by AR transcript reduction, it was hypothesized that ARlnc1 affects AR post-transcriptionally. To test this hypothesis, sub-cellular localization of AR transcripts was performed using smFISH after depleting ARlnc1. Successful in situ knockdown of ARlnc1 was confirmed using siRNAs, antisense oligos (ASOs) and the blocking oligos targeting ARlnc1-AR interaction (Blocking-ASOs) in MDA-PCa-2b cells (FIG. 14h-i). Quantification of the sub-cellular distribution of ARlnc1 indicated that the nuclear fraction of ARlnc1 was enriched only in the si-ARlnc1 condition (FIG. 14j), as expected for siRNAs that are typically more functional in the cytosol[45]. ARlnc1 knockdown or blocking AR-ARlnc1 interaction mediated a drastic reduction in cytoplasmic levels of AR transcript, but did not affect nuclear AR transcript levels, thereby resulting in an increased nuclear AR fraction (FIG. 7a-b, FIG. 14k-l). This observation was further supported by BrU-seq and BrU-chase-seq, high-throughput tools that monitors transcript synthesis and stability. Upon ARlnc1 knockdown, while synthesis rate of AR transcript remains the same (FIG. 14m), while the stability of the transcript decreases, preferentially through the 3'UTR region (FIG. 14n). Taken together, the data indicate that ARlnc1 regulates the cytoplasmic levels of AR transcripts and that transcriptional coupling between AR and ARlnc1 transcripts is mediated by direct interactions which are encoded in their sequences.

Inhibition of ARLNC1 Delays Prostate Cancer Growth In Vitro and In Vivo

Figure 8:
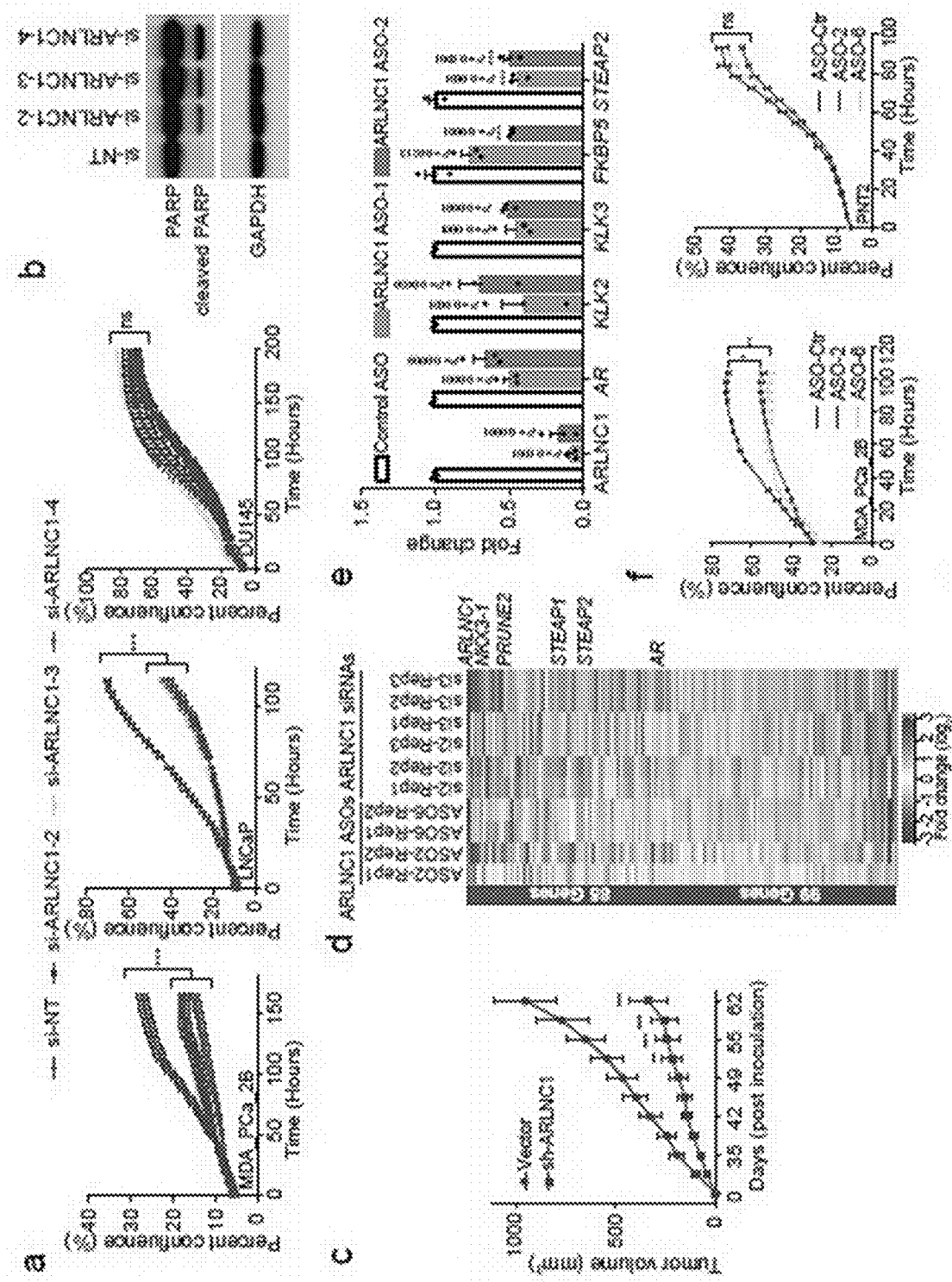
FIG. 8 shows ARLNC1 as a therapeutic target in AR-positive prostate cancer models. a, siRNA knockdown of ARLNC1 in vitro in AR-positive prostate cancer cell lines (MDA-PCa-2b and LNCaP) inhibits cell proliferation. b, ARLNC1 loss leads to increased apoptosis as shown by western blot analysis of PARP and cleaved PARP in LNCaP cells following ARLNC1 knockdown. c, Tumor growth of LNCaP-AR cells expressing shRNA targeting ARLNC1 or shRNA vector. d, Gene expression profiling for siRNA-mediated or ASO-mediated ARLNC1 knockdown in MDA-PCa-2b cells. e, qRT-PCR analysis of ARLNC1, AR, and AR targets (KLK2, KLK3, FKBP5, and STEAP2) in MDA-PCa-2b cells transfected with ASOs against ARLNC1. f, Transfection of ASOs targeting ARLNC1 in AR-positive MDA-PCa-2b cells inhibits cell proliferation. g-h, Effect of ASO treatment on the growth of MDA-PCa-2b xenografts in male NOD-SCID mice, with control ASO (n=15) or ARLNC1 ASO (n=13) treatment subcutaneously at 50 mg/kg, five times per week for three weeks. Tumors were measured by caliper bi-weekly (g) and tumor weights were measured at end point (h). i, Model depicting positive feedback loop between ARLNC1 and AR that is critical for prostate cancer growth.
Figure 8:
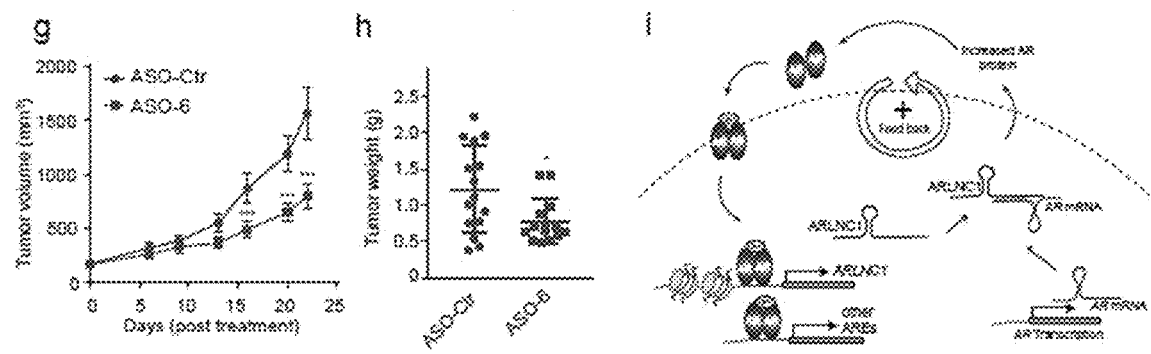

Having established a role for ARlnc1 in the regulation of AR signaling, the biological effects of ARlnc1 were further evaluated in prostate cancer cell lines. GO analysis of the knockdown microarray data showed that ARlnc1-regulated genes were involved in cell proliferation and apoptosis (FIG. 4a). Knockdown of ARlnc1 had a significant effect on the proliferation of AR-dependent MDA-PCa-2b and LNCaP cells, while no effect in AR-negative Du145 and PC3 cells (FIG. 8a, FIG. 15a-b). Knockdown of ARlnc1 also led to an increase in apoptosis in AR-positive prostate cancer cells (FIG. 8b, FIG. 15c). These results translated to effects in vivo, as cells expressing shRNA targeting ARlnc1 formed smaller tumors in mice compared to cells expressing non-targeting shRNA (FIG. 8c), indicating that ARlnc1 is an important survival factor for AR-dependent prostate cancer.

Since modulation of ARlnc1 levels resulted in a striking proliferation phenotype, it was contemplated that ARlnc1 inhibition finds use therapeutically for the treatment of prostate cancer. Antisense oligos (ASOs) have recently been shown to be effective in targeting RNA in vivo[46-49], thus, ASOs targeting ARlnc1 (FIG. 15d) were generated. Transfection of ASOs exhibited strong knockdown efficiency (FIG. 15e), and ASO-mediated knockdown resulted in similar effects on gene expression profiling as siRNA (FIG. 8d-e, FIG. 15f). Furthermore, AR-positive cells transfected with ARlnc1 ASOs exhibited retarded growth, similar to siRNA (FIG. 8f). To evaluate the therapeutic use of ARlnc1 ASOs in vivo, the cellular free uptake efficiency of ARlnc1 ASOs, a prerequisite for ASO therapeutic use, was evaluated. Several ASOs significantly reduced ARlnc1 levels through free uptake (FIG. 15g). Free uptake of ARlnc1 ASOs led to a significant decrease in the proliferation capacity of MDA-PCa-2b cells in both normal cell culture and 3D sphere conditions (FIG. 15h-j). Treatment of mice bearing MDA-PCa-2b xenografts with ARlnc1-targeting ASO led to significant decreases in tumor growth compared to control ASO (FIG. 8g-h, FIG. 16a-e). Taken together, these data demonstrate that ARlnc1 plays a critical role in the proliferation of AR-dependent prostate cancer and can be effectively exploited as a therapeutic target, especially considering the association of this lncRNA with aggressive androgen signaling (FIG. 16f-j).

As AR signaling remains a significant driver of CRPC pathogenesis, it is imperative to generate novel strategies for targeting of the pathway. Even with the addition of enzalutamide or abiraterone to CRPC treatment regimens, progression invariably occurs. Exploiting players other than AR itself that are pivotal to maintaining the magnitude of the androgen response is an alternative approach. This example describes a comprehensive profiling of AR-regulated, prostate cancer-associated lncRNAs and functionally characterized the top-ranking candidate, ARlnc1. A positive feedback loop between ARlnc1 and AR that maintains the androgen transcriptional program in AR-positive prostate cancer cells, specifically through regulating the cellular levels of AR, was identified (FIG. 8i). As a non-coding regulator of AR signaling, ARlnc1 provides a mechanistic biomarker and a therapeutic target for prostate cancer; acting upstream of AR signaling also presents the possibility that targeting of ARlnc1 may afford an additional option to patients that have de novo or acquired resistance to therapies targeting AR itself (e.g., enzalutamide or abiraterone). Furthermore, specific antisense nucleotides targeting ARlnc1, which are shown to be only expressed in the prostate, can circumvent undesirable side effects that occur in other tissues with exposure to androgen synthesis inhibitors or antiandrogens.

TABLE 1

|        |                  |                                                              | SEQ ID NO |
|--------|------------------|--------------------------------------------------------------|-----------|
| Primer | ARLNC1-NB-F1     | TCCTGAGCCGAAAATAAGGA                                         | 181       |
| Primer | ARLNC1-NB-T7-R1  | GATCACTAATACGACTCACTATAGGGAGAGGAGACCCTCATTTCCTTCCAGCTT       | 1         |
| Primer | ARLNC1-5RACE-R1  | AAGAGCCATGGAACCAGCACCTGAA                                    | 2         |
| Primer | ARLNC1-5RACE-R2  | GGGAACGAGTTCCAGTGGACAAGGT                                    | 3         |
| Primer | ARLNC1-3RACE-F1  | GGCTCTTCCTGAGCCGAAAATAAGG                                    | 4         |
| Primer | ARLNC1-3RACE-F2  | CTCGTTCCCATCTACCCTCCACTCT                                    | 5         |
| Primer | GAPDH-F          | CCATCACCATCTTCCAGGAGCGA                                      | 6         |
| Primer | GAPDH-R          | GGTGGTGAAGACGCCAGTGGA                                        | 7         |
| Primer | ACTB-F           | CACCATTGGCAATGAGCGGTTC                                       | 8         |
| Primer | ACTB-R           | AGGTCTTTGCGGATGTCCACGT                                       | 9         |
| Primer | HMBS-F           | ACGGCTCAGATAGCATACAAGAG                                      | 10        |
| Primer | HMBS-R           | GTTACGAGCAGTGATGCCTACC                                       | 11        |
| Primer | AR-F             | CAGTGGATGGGCTGAAAAAT                                         | 12        |
| Primer | AR-R             | GGAGCTTGGTGAGCTGGTAG                                         | 13        |
| Primer | ARLNC1-F         | CCTTGTCCACTGGAACTCGT                                         | 14        |
| Primer | ARLNC1-R         | TATAACCTTGGGGGCCATGA                                         | 15        |
| Primer | TMPRSS2-F        | CAGGAGTGTACGGGAATGTGATGGT                                    | 16        |
| Primer | TMPRSS2-R        | GATTAGCCGTCTGCCCTCATTTGT                                     | 17        |
| Primer | MYC-F            | GCTCGTCTCAGAGAAGCTGG                                         | 18        |
| Primer | MYC-F            | GCTCAGATCCTGCAGGTACAA                                        | 19        |
| Primer | KLK2-F           | GGCTCTGGACAGGTGGTAAAGA                                       | 20        |
| Primer | KLK2-R           | CGGTAATGCACCACCTTGGTGT                                       | 21        |
| Primer | KLK3-F           | ACGCTGGACAGGGGGCAAAAG                                        | 22        |
| Primer | KLK3-R           | GGGCAGGGCACATGGTTCACT                                        | 23        |
| Primer | FKBP5-F          | GCGAAGGAGAAGACCACGACAT                                       | 24        |
| Primer | FKBP5-F          | TAGGCTTCCCTGCCTCTCCAAA                                       | 25        |
| Primer | SLC45A3-F        | TCGTGGGCGAGGGCTGTA                                           | 26        |
| Primer | SLC45A3-R        | CATCCGAACGCCTTCATCATAGTGT                                    | 27        |

TABLE 1-continued

| | | | SEQ ID NO |
|---|---|---|---|
| Primer | ETV1-F | GCAAGAAGGCTTCCTGGCTCAT | 28 |
| Primer | ETV1-R | CCTTCCCGATACATTCCTGGCT | 29 |
| Primer | STEAP2-F | AAAATTTTACATGCCCTGTAATGGA | 30 |
| Primer | STEAP2-R | TCTGTATGGAAAAGGATGGTAGCA | 31 |
| Primer | NKX3.1-F | CAGTCCCTACTGAGTACTCTTTCTCTC | 32 |
| Primer | NKX3.1-R | CACAGTGAAATGTGTAATCCTTGC | 33 |
| Primer | POU1F1-F | TCACAGTGCTGCCGAGTGTCTA | 34 |
| Primer | POU1F1-R | CCATAGGTTGATGGCTGGTTTCC | 35 |
| Primer | IRF1-R | TAGCATCTCGGCTGGACTTCGA | 37 |
| Primer | FOX41-F | GCAATACTCGCCTTACGGCTCT | 38 |
| Primer | FOX41-R | GGGTCTGGAATACACACCTTGG | 39 |
| Primer | BRD4-F | CGCTATGTCACCTCCTGTTTGC | 40 |
| Primer | BRD4-R | ACTCTGAGGACGAGAAGCCCTT | 41 |
| Primer | EZH2-F | GACCTCTGTCTTACTTGTGGAGC | 42 |
| Primer | EZH2-R | CGTCAGATGGTGCCAGCAATAG | 43 |
| Primer | LSD1-F | CTCTTCTGGAACCTCTATAAAGC | 44 |
| Primer | LSD1-R | CATTTCCAGATGATCCTGCAGCAA | 45 |
| Primer | AR-3'UTR-F | TTCCCATTGTGGCTCCTATC | 46 |
| Primer | AR-3'UTR-R | GTGGCTGGCACAGAGTAGTG | 47 |
| Primer | AR-3'UTR1-980-T7-F | GATCACTAATACGACTCACTATAGGGAGAGGAGAAGCATTGGAAACCCTATTTCC | 48 |
| Primer | AR-3'UTR-1-980-R | GAACTCGAGGCCAAGTTTTGGCTGAAGAG | 49 |
| Primer | AR-3'UTR-1-1988-R | GAGTTCATGGGTGGCAAAGTAT | 50 |
| Primer | LacZ-T7-F | GATCACTAATACGACTCACTATAGGGAGAGGAGAGTCGTTTTACAACGTCGTGACTG | 51 |
| Primer | LacZ-R | GTACGGGGTATACATGTCTGACA | 52 |
| Primer | ARLNC1-S-T7-F | GATCACTAATACGACTCACTATAGGGAGAGGAGAAAAAGTACTGTAGCCTTCAGTAATTC | 53 |
| Primer | ARLNC1-S-R | TTGGCACAGAAGCAGTACACAC | 54 |
| Primer | ARLNC1-AS-F | AAAAGTACTGTAGCCTTCAGTAATTC | 55 |
| Primer | ARLNC1-S-T7-R | GATCACTAATACGACTCACTATAGGGAGAGGAGATTGGCACAGAAGCAGTACACAC | 56 |
| Primer | ARLNC1-de1700-1300-F | GAAATAGTGCCTTTGTGTATATTCTGCCTA | 57 |
| Primer | ARLNC1-de1700-1300-R | TAGGCAGAATATACACAAAGGCACTATTTC | 58 |
| Primer | ARLNC1-Frag-700-R | CAAAGGCACTATTTCCAGAT | 59 |
| Primer | ARLNC1-Frag-1300-R | GAACACAGATTCACCTTTTC | 60 |
| Primer | ARLNC1-Frag-T7-1301-F | GATCACTAATACGACTCACTATAGGGAGAGGAGATGTATATTCTGCCTAAGGCA | 61 |
| Primer | ARLNC1-Frag-T7-701-F | GATCACTAATACGACTCACTATAGGGAGAGGAGACGGATATAAGTTAGGTAAAA | 62 |
| Primer | ARLNC1-promoter-primer1-F | TTAACTCTGGTCTCCCCAACA | 63 |

TABLE 1-continued

| | | | SEQ ID NO |
|---|---|---|---|
| Primer | ARLNC1-promoter-primer1-R | GAGATTAAAGCTGAATTTGCTGGT | 64 |
| Primer | ARLNC1-promoter-primer2-F | TGTTGCAATGTCACCACCTT | 65 |
| Primer | ARLNC1-promoter-primer2-R | AGCAGGTAAAGCGACAGGAA | 66 |
| Primer | KLK3-promoter-primer-F | GCCTGGATCTGAGAGAGATATCATC | 67 |
| Primer | KLK3-promoter-primer-R | ACACCTTTTTTTTTCTGGATTGTTG | 68 |
| shRNA | sh-ARLNC1 | GCAGUAAGUGGAAGAGUUC | 69 |
| siRNA | si-ARLNC1-2 | GCAGUAAGUGGAAGAGUUC | 70 |
| siRNA | si-ARLNC1-3 | CUUCCUGAGCCGAAAAUAA | 71 |
| siRNA | si-ARLNC1-4 | AGGAAACUCCAUAGACCUU | 72 |

TABLE 2

(SEQ ID NO: 73)
AAAAGTACTGTAGCCTTCAGTAATTCTTTCCATGAGTATTTGCTCGTGCT

ATTTTTTTTTCAGTCTTTATTTTTCCCAAATTATCCTTCCCCTCTCTTAA

TTTGAATGAATAGAAGGTTCTAGATTTATGGGTTTTTTTTTTTTTAATCT

TTTTCTTTTTTGAGACAGACTCTCACTCTCGGGCTGGAGTGCAGCGGCAT

GATCTCGGCTCACTGCAACCTCTGCCTCCCGGGTTCATGTAATTCTCATG

CCTCAGCCTCCCAAGTAGCTGGGATTACAGGCACACGCCACCATGCCTGG

CTGATTTAAGATTATTTTTTCACAAAACTTTGAAGACATATCTTCTTAT

CTTCTGGCTTCTGTTGTTGTTCATTTACAGGTTTTCAGGTGCTGGTTCCA

TGGCTCTTCCTGAGCCGAAAATAAGGAAACTCCATAGACCTTGTCCACTG

GAACTCGTTCCCATCTACCCTCCACTCTATCCAGCCCCATGAGGACAAGG

AACATGATTGGTTTTGCTCACTGCCGTATCTTCCGTACCTAGTACGTAAC

AGGACATCAATAAATATTAGTTGAATGGAAGATTAAATCAACAAAATGGG

TGATGGATCTCTGCAGTAAGTGGAAGAGTTCTTCATGGCCCCCAAGGTTA

TATCCATCTAGAACTTCAGCACGTAATTTCATCTGGAAATAGTGCCTTTG

CGGATATAAGTTAGGTAAAACTGAAGATGAGATCATACTGGATTAGGATG

GGATCTAAATCCAATGAAAATGTCTTCATAAAAAACAGGAAAGAACCCAT

AGAAACACAAGGAAGAAGGTCATGTGAAGATGGAGGCAGAGATTGGAGGG

ATGCAGCCACCGGCCCAGGAATGCCAGCAGCCACCCAGAAGCTGGAAGGA

AATGAGGGATTCTCTCCTAGAACCTTTAGAGAGAACATGGTCCTGTGAAC

AGCTTGATTTTGGACTTGCCCATAGCTTGTATACTCTTACTTTGGATACA

ATTTTATCCAAACTTGGCTAAACAGTTTCTCAGCCTATGGAAAATTTAAA

ATGGAGAAGATTCAACTCGATTCTTACAGATTCAAAGCAAGAAAATGATG

GGAACATAGGAGGAGACCAAGAAAGCCTATAAAAAGCAAAATATGAAGT

GAACATTGTGGTAGCTTTAAGATGTTTAGTGTAGCTGCAGGCACCCTATA

TABLE 2-continued

CACATGAAAACCCCCAAGGGGAATCCCCATATCACAGTGTAGTGTGATAT

TTGACATTCGTGATCATCTAGAGATGTACAGAAAAGGTGAATCTGTGTTC

TGTATATTCTGCCTAAGGCAAAGAAATGTTTAGCTCTCTTTAAAATAGTT

CCATAATTTTTCTAAAAAGCTTTGCTTGAAAACTGTAAGCTTCCCATAT

CTGGAGCATTTCACTTTAAATATTTGGATAAATATGTTATCTTCTTACTT

GGACATTTCATGTGTTTAGGGATTGTCTTCTAAATTCTTCCTAATTCATA

TAGCTGCTAACACTTCCCGCAGAGCTAAACCATTACAGATATGAAATAAA

GACCTATTGATTTGACTTACTTTTACTTGTAAAACCTTCTGAGTGTTATA

ACCTCATTTAATCTTTCAGCATTTACAGTTTCAAGAGTTTGTGTCACAAT

TAGAAGAATTCAGCTGCACCTCCAAGTGACAGCAGTTGCTCTGGTTGGTG

GGTGATCTCAGGAGGCTTGAGAATTGCTTTGTCTGTGAGGGAAGTAAGAC

ATTTTCAGAGCCCCACTTTAGAAGGTGTGAACTGGCTAGATAATGAACCC

CAGGGCTAACGCTGCTATAGCAGTGGGAAGGAGGTGATGGGTTTTCAGTT

TGGACCTCAAACATCAATACCCTCCTGGTACGGGGAGGAACAGAGTCCCT

CCTTTACTTCTCCATTAGAAAGAATGAGATGGCAAGACAATGAAACAGGC

AAAGTGAACAGAGATGCAAGCAAAATTCAGGTGAGAGAGCCAGAGCATC

ACTCAGCCATTCCTGACATGTAAAACAGGCAACTAGAAATTTGCAGAAAG

GAAGCGAAGTCTCCATAAAGATGTTTTTAAAGTGAGCTTGAAGTATTTGG

AGACAATTCAGTGTTACATAAAATCTGCAAATCTCTGGATAAAGAAGCAG

AGATCCCAGCATGGGACAAATGGAGCCTCAAAAGTGGGAAGAAGACAGAG

AAGACCAGGGCAGAATGCATCTCTTCCTTTCTCTTGGCTTTCCTGGATAA

GGACTGCATCATTCCTGTGGAAGGACAGGCCATCAGCTCCGAAACACTGT

ATGTATTTTCCAGTATATACTGCTAGCTGTGTGATGTTGGGAAAATTTGT

TACCCTGTCTAACCCCCACTTCCCTCATCTGTAAAATGGAAATAATGATA

GTACCTACCTATCTCATAGGTGGCAACTACAAGGGGCAGCACACTCAGGG

TABLE 2-continued

AATTAAGGAAGTTTCAGTGAACATCAACTTTATGAACACAGTGTTCATAA

AGGCAGGTCAGTGCAGTGGTTTGGGAGCCAGGAGAAGCACGTGGGCCGGA

GTGTGCCTGCAGGAGACAAGGTCAGAGATGTTGCTAATAATGGAGAATAA

AGGATGCATTCTCATTACTGACCTTGGAGTCGTTCATTCATTCCCAGAAT

GTGTTTTGTCAGCTTACTAAAACACTAAGTTAAATAATCCCAGGTTTTGT

TTATTATAGATACTAGGACTTAGTGGACCCAAGGTTAATGACATCCAGAG

TAGACAAACATCAAGTGTGTACTGCTTCTGTGCCAA

TABLE 3

| Gene | Sequence (5'-3') | SEQ ID NO |
|---|---|---|
| ARLNC1 (31 probes) | ctagaaccttctattcattc | 74 |
| | gaacaacaacagaagccaga | 75 |
| | catgaaccagcaccctgaaa | 76 |
| | tggagtaccttattacgg | 77 |
| | gaacgagttccagtggacaa | 78 |
| | taaccttgggggcatgaag | 79 |
| | gtgctgaagttctagatgga | 80 |
| | agcagctatatgaattagga | 81 |
| | gtttagctctgcgggaagtg | 82 |
| | ggictaatacatatctgt | 83 |
| | caaccagagcaactgctgtc | 84 |
| | atgtcttacttccctcacag | 85 |
| | cttctaaagtggggctctga | 86 |
| | tcattatctagccagttcac | 87 |
| | cactgctatagcagcgttag | 88 |
| | aactgaaaacccatcacctc | 89 |
| | gggtattgatgtttgaggtc | 90 |
| | taaaggagggactctgttcc | 91 |
| | tgccatctcattctttctaa | 92 |
| | tcactttgcctgtttcattg | 93 |
| | tcaggaatggctgagtgatg | 94 |
| | ttctagttgcctgttttaca | 95 |
| | gtctccaaatacttcaagct | 96 |
| | caggaatgatgcagtcctta | 97 |
| | tacatacagtgtttcggagc | 98 |
| | aacttccttaattccctgag | 99 |
| | gcctttatgaacactgtgtt | 100 |
| | aacatctctgaccttgtctc | 101 |
| | catcctttattctccattat | 102 |
| | tgtttgtctactctggatgt | 103 |
| | gcacagaagcagtacacact | 104 |
| AR (62 probes) | aaagctcctcggtaggtctt | 105 |
| | cacgctctggaacagattct | 106 |
| | tgaaggttgctgttcctcat | 107 |
| | cagcagggacaacgtggatg | 108 |
| | tgcttaagccggggaaagtg | 109 |
| | aggatgtctttaaggtcagc | 110 |
| | aagtgcccctaagtaattg | 111 |
| | ttggcgttgtcagaaatggt | 112 |
| | cgacactgccttacacaact | 113 |
| | aaaagtggggcgtacatgca | 114 |
| | caatggggcacaaggagtgg | 115 |
| | agcagagaacctttgcattc | 116 |
| | cagtatcttcagtgctcttg | 117 |
| | cccttgaaaggggaatactc | 118 |
| | ttctagccccttggtgtaac | 119 |
| | tagacgagcagttcaagtgc | 120 |
| | ccggacttgtagagagacag | 121 |
| | gtagtcgcgactctggtacg | 122 |
| | ccagagccagtggaaagttg | 123 |
| | ttgatgcgagcgtgggatg | 124 |
| | aagagagtgtgccaggatga | 125 |
| | catacaactggccttcttcg | 126 |
| | acacatcaggtgcggtgaag | 127 |
| | gactgggatagggcactctg | 128 |
| | ccatttcgcttttgacacaa | 129 |

TABLE 3-continued

| Gene | Sequence (5'-3') | SEQ ID NO |
|---|---|---|
| | taaggtccggagtagctatc | 130 |
| | caatgggcaaaacatggtcc | 131 |
| | cttctggggtggaaagtaat | 132 |
| | catctccacagatcaggcag | 133 |
| | tccatagtgacacccagaag | 134 |
| | tcagcgggctcttttgaagaa | 135 |
| | caagtttcttcagcttccgg | 136 |
| | tcctcctgtagtttcagatt | 137 |
| | tgtgacactgtcagcttctg | 138 |
| | ctgacattcatagccttcaa | 139 |
| | gcttccaggacattcagaaa | 140 |
| | acacactacacctggctcaa | 141 |
| | caaggctgcaaaggagtcgg | 142 |
| | ccagttcattgaggctagag | 143 |
| | cacttgaccacgtgtacaag | 144 |
| | cacgtgtaagttgcggaagc | 145 |
| | aggagtactgaatgacagcc | 146 |
| | catggcaaacaccatggcc | 147 |
| | cattggtgaaggatcgccag | 148 |
| | aagtagagcatcctggagtt | 149 |
| | attgaaaaccagatcagggg | 150 |
| | ctgtacatccgggacttgtg | 151 |
| | ttgagagaggtgcctcattc | 152 |
| | tgatttggagccatccaaac | 153 |
| | tcatgcacaggaattcctgg | 154 |
| | atgctgaagagtagcagtgc | 155 |
| | tttttgattttcagccat | 156 |
| | ccttgatgtagttcattcga | 157 |
| | gcatgcaatgatacgatcga | 158 |
| | agcaggatgtgggattttt | 159 |
| | ttggtgagctggtagaagcg | 160 |
| | aagtgaactgatgcagctct | 161 |
| | ccatgtgtgacttgattagc | 162 |
| | atcatttccggaaagtccac | 163 |
| | cttgcacagagatgatctct | 164 |
| | tttcccagaaaggatcttgg | 165 |
| | ggtgtggaaatagatgggct | 166 |
| PCAT1 (29 probes) | gcctatgcagatatccaata | 167 |
| | aagggtacagatgctttctc | 168 |
| | gacctgtgggaattcataca | 169 |
| | agaggttcctttcttcatta | 170 |
| | taggtagctctttgtactca | 171 |
| | gctatgcatcttatatccttt | 172 |
| | tctttaattgctcaggttcc | 173 |
| | caagtgccagttaagtgtga | 174 |
| | ggccttattaagatgggatc | 175 |
| | cttatccattggtgtttctg | 176 |
| | cacttagaggcacatgggaa | 177 |
| | ttaaagtccagttaggttcc | 178 |
| | tttctcttctcacttctagt | 179 |
| | ttatcttgggaggttccaat | 180 |
| | catggtcttatgtatctgcg | 182 |
| | caaaggcgttggtgatgttg | 183 |
| | gtctttgtcgacttccaatg | 184 |
| | gcttcaatgattcctctcaa | 185 |
| | atggtcaacattgcgttctt | 186 |
| | cacccacttatcaagttttt | 187 |
| | tttggattttttgctgagctc | 188 |
| | ggttattgttgttgcgtaga | 189 |
| | cccaaatccacttttcattg | 190 |
| | attgctggttgccatatata | 191 |
| | gctcattgatttgttgagca | 192 |
| | aacttttgaagcgctgcttg | 193 |
| | aactatgtagcccaatttgt | 194 |
| | ttgaaagcgtgttctgcat | 195 |
| | gtgcgtcaggattcgacaaa | 196 |
| DANCR (30 probes) | cgggaagactctgggcaagg | 197 |
| | cgggcgcacaaaccagagag | 198 |
| | gcaactccagctgacaaaga | 199 |
| | cgaaaccgctacatagtga | 200 |
| | aactcctggagctcaaggtc | 201 |
| | acttccgcagacgtaagaga | 202 |
| | tgcgctaagaactgaggcag | 203 |
| | ataccagcaacaggacattc | 204 |
| | gggatagttggcttaagtca | 205 |

TABLE 3-continued

| Gene | Sequence (5'-3') | SEQ ID NO |
|---|---|---|
| | ggcactttcctattgtaact | 206 |
| | cacgtggttgctacaagtta | 207 |
| | cagcattgtcactgctctag | 208 |
| | aacatgaagcacctgctaca | 209 |
| | acagcgtgaaacttgtagag | 210 |
| | gcttttgtaggttcatgact | 211 |
| | gctgagcatcttcaaagatt | 212 |
| | ggtcttggagaaatttcaga | 213 |
| | gcatgatcctgttttgttca | 214 |
| | tgcagcttgggtgtgtattc | 215 |
| | gccaaaccaaaatagggcta | 216 |
| | tgtggctgaagatctcatgg | 217 |
| | ggaagattttatctcctgc | 218 |
| | acttgcagctgatgaaagct | 219 |
| | tcggttactcaaatagcca | 220 |
| | gtcacccacagaatccaatt | 221 |
| | tgatgtgcaaagcggtcatc | 222 |
| | gaaggtaaggatgataccca | 223 |
| | tttgactggcacaaaaggtt | 224 |
| | ggtgatgacatatcaagagc | 225 |
| | agccaagacaagtggcaatt | 226 |
| EZH2 (34 probes) | ccaacaaactggtcccttct | 227 |
| | gtactctgattttacacgct | 228 |
| | aacctcttgagctgtctcag | 229 |
| | ctaacttcatcagctcgtc | 230 |
| | cttcgctgtaccattcttg | 231 |
| | aagtcactggtcaccgaaca | 232 |
| | atgggatgacttgtgttgga | 233 |
| | agcaactgcattcagagtct | 234 |
| | ataaaattctgctgtagggg | 235 |
| | ctgttcggtgagttctttat | 236 |
| | gtacattcaggaggaagtgc | 237 |
| | catcgcctacagaaaagcgt | 238 |
| | gcacttacgatgtaggaagc | 239 |
| | gttgggtgttgcatgaaaag | 240 |
| | ctgtgttcttccgcttataa | 241 |
| | aaggtagttgtctagagct | 242 |
| | aatgctggtaacactgtggt | 243 |
| | gtgagagcagcagcaaactc | 244 |
| | tgctactgttattgggaagc | 245 |
| | ttccagcacattaatggtgg | 246 |
| | ttggtgtagacaccgagaa | 247 |
| | ggactctaaacattgaggct | 248 |
| | taacctagcaatggcacaga | 249 |
| | ctgtctacatgttttggtcc | 250 |
| | ctggagctatgatgctagat | 251 |
| | ctgtatctttctgcagtgtg | 252 |
| | aaacatggttagaggagccg | 253 |
| | tggatgatcacagggttgat | 254 |
| | atcacacaagggcacgaact | 255 |
| | agatggtgccagcaatagat | 256 |
| | tgataaaaatcccccagcct | 257 |
| | tctccacagtattctgagat | 258 |
| | gatggctctcttggcaaaaa | 259 |
| | aaaaacagctcttcgccagt | 260 |
| FOXA1 (47 probes) | tgcccaatacaaccatccag | 261 |
| | catcttcacagttcctaaca | 262 |
| | tgtctgcgtagtagctgttc | 263 |
| | aggtgttcatggagttcatg | 264 |
| | tcgtagtcatggtgttcatg | 265 |
| | gttggcataggacatgttga | 266 |
| | cgcagtcatgctgttcatgg | 267 |
| | tagctgcgcttgaacgtctt | 268 |
| | gagatgtacgagtagggcgg | 269 |
| | ctggatggccatggtgatga | 270 |
| | atgatccactggtagatctc | 271 |
| | tgccggtaataggggaagag | 272 |
| | agccgttctcgaacatgttg | 273 |
| | tgcttctcgcacttgaagcg | 274 |
| | ctggagtcttcaactccgag | 275 |
| | aacgggtggttgaaggagta | 276 |
| | ggacatgaggttgttgatgg | 277 |
| | ttgaagtccagcttatgctg | 278 |
| | tattgcagtgcctgttcgta | 279 |
| | caacgtagagccgtaaggcg | 280 |
| | atacacaccttggtagtacg | 281 |
| | aagtgtttaggacgggtctg | 282 |
| | ttgcactgggggaaaggttg | 283 |
| | aaattggtttggggttgtct | 284 |
| | ggatcattaaacttcgcagg | 285 |
| | gtagggggtcaggtaaggag | 286 |
| | attgccacagacctgtaaac | 287 |
| | cttttaagagcctctagtgt | 288 |
| | agcaaatggctctgatgttt | 289 |
| | gcatgtgcataattaagtcc | 290 |
| | acggaggatgtctacacatc | 291 |
| | gcaactcttgagaatgtatc | 292 |
| | ttgggtccttgtaactttc | 293 |
| | attcctgaggaattgattcc | 294 |
| | agaagcagagttcttgaggg | 295 |
| | atgacatgaccatggcactc | 296 |
| | ctctcctccaacattgtaat | 297 |
| | aaatccagctccctataact | 298 |
| | ttgaatcttggaccacgttt | 299 |
| | atggccactatcaataggat | 300 |
| | agcacacgatggcaatgatt | 301 |
| | tccaactgtggaaagtgcat | 302 |
| | gtctggctatactaacacca | 303 |
| | gaacattttccacggcttaa | 304 |
| | gtccttaactgcaaatgatc | 305 |
| | aaacacagaaggcttaagcc | 306 |
| | ttaattctatcagccacagc | 307 |

REFERENCES

1. Mercer, T. R., Dinger, M. E. & Mattick, J. S. Long non-coding RNAs: insights into functions. *Nat Rev Genet* 10, 155-9 (2009).
2. Wang, K. C. & Chang, H. Y. Molecular mechanisms of long noncoding RNAs. *Mol Cell* 43, 904-14 (2011).
3. Rinn, J. L. & Chang, H. Y. Genome regulation by long noncoding RNAs. *Annu Rev Biochem* 81, 145-66 (2012).
4. Rinn, J. L. et al. Functional demarcation of active and silent chromatin domains in human HOX loci by noncoding RNAs. *Cell* 129, 1311-23 (2007).
5. Lee, N., Moss, W. N., Yario, T. A. & Steitz, J. A. EBV noncoding RNA binds nascent RNA to drive host PAXS to viral DNA. *Cell* 160, 607-18 (2015).
6. Wutz, A., Rasmussen, T. P. & Jaenisch, R. Chromosomal silencing and localization are mediated by different domains of Xist RNA. *Nat Genet* 30, 167-74 (2002).
7. Prensner, J. R. et al. The long noncoding RNA SChLAP1 promotes aggressive prostate cancer and antagonizes the SWI/SNF complex. *Nat Genet* 45, 1392-8 (2013).
8. Gupta, R. A. et al. Long non-coding RNA HOTAIR reprograms chromatin state to promote cancer metastasis. *Nature* 464, 1071-6 (2010).
9. Faghihi, M. A. et al. Expression of a noncoding RNA is elevated in Alzheimer's disease and drives rapid feed-forward regulation of beta-secretase. *Nat Med* 14, 723-30 (2008).
10. Iyer, M. K. et al. The landscape of long noncoding RNAs in the human transcriptome. *Nat Genet* 47, 199-208 (2015).
11. Malik, R. et al. The lncRNA PCAT29 inhibits oncogenic phenotypes in prostate cancer. *Mol Cancer Res* 12, 1081-7 (2014).
12. Shukla, S. et al. Identification and Validation of PCAT14 as Prognostic Biomarker in Prostate Cancer. *Neoplasia* 18, 489-99 (2016).

13. Lu-Yao, G. L. et al. Fifteen-year survival outcomes following primary androgen-deprivation therapy for localized prostate cancer. *JAMA Intern Med* 174, 1460-7 (2014).
14. Huggins, C. & Hodges, C. V. Studies on prostatic cancer. I. The effect of castration, of estrogen and of androgen injection on serum phosphatases in metastatic carcinoma of the prostate. 1941. *J Urol* 167, 948-51; discussion 952 (2002).
15. Treatment and survival of patients with cancer of the prostate. The Veterans Administration Co-operative Urological Research Group. *Surg Gynecol Obstet* 124, 1011-7 (1967).
16. Chen, Y., Sawyers, C. L. & Scher, H. I. Targeting the androgen receptor pathway in prostate cancer. *Curr Opin Pharmacol* 8, 440-8 (2008).
17. Wong, Y. N., Ferraldeschi, R., Attard, G. & de Bono, J. Evolution of androgen receptor targeted therapy for advanced prostate cancer. *Nat Rev Clin Oncol* 11, 365-76 (2014).
18. Mukherji, D., Pezaro, C. J. & De-Bono, J. S. MDV3100 for the treatment of prostate cancer. *Expert Opin Investig Drugs* 21, 227-33 (2012).
19. Scher, H. I. et al. Increased survival with enzalutamide in prostate cancer after chemotherapy. *N Engl J Med* 367, 1187-97 (2012).
20. Tran, C. et al. Development of a second-generation antiandrogen for treatment of advanced prostate cancer. *Science* 324, 787-90 (2009).
21. Scher, H. I. et al. Antitumour activity of MDV3100 in castration-resistant prostate cancer: a phase 1-2 study. *Lancet* 375, 1437-46 (2010).
22. Stein, M. N., Goodin, S. & Dipaola, R. S. Abiraterone in prostate cancer: a new angle to an old problem. *Clin Cancer Res* 18, 1848-54 (2012).
23. Reid, A. H. et al. Significant and sustained antitumor activity in post-docetaxel, castration-resistant prostate cancer with the CYP17 inhibitor abiraterone acetate. *J Clin Oncol* 28, 1489-95 (2010).
24. de Bono, J. S. et al. Abiraterone and increased survival in metastatic prostate cancer. *N Engl J Med* 364, 1995-2005 (2011).
25. Watson, P. A., Arora, V. K. & Sawyers, C. L. Emerging mechanisms of resistance to androgen receptor inhibitors in prostate cancer. *Nat Rev Cancer* 15, 701-11 (2015).
26. Antonarakis, E. S. et al. AR-V7 and resistance to enzalutamide and abiraterone in prostate cancer. *N Engl J Med* 371, 1028-38 (2014).
27. Attard, G., Richards, J. & de Bono, J. S. New strategies in metastatic prostate cancer: targeting the androgen receptor signaling pathway. *Clin Cancer Res* 17, 1649-57 (2011).
28. Hearn, J. W. et al. HSD3B1 and resistance to androgen-deprivation therapy in prostate cancer: a retrospective, multicohort study. *Lancet Oncol* 17, 1435-1444 (2016).
29. Chan, S. C., Li, Y. & Dehm, S. M. Androgen receptor splice variants activate androgen receptor target genes and support aberrant prostate cancer cell growth independent of canonical androgen receptor nuclear localization signal. *J Biol Chem* 287, 19736-49 (2012).
30. Robinson, D. et al. Integrative clinical genomics of advanced prostate cancer. *Cell* 161, 1215-28 (2015).
31. Visakorpi, T. et al. In vivo amplification of the androgen receptor gene and progression of human prostate cancer. *Nat Genet* 9, 401-6 (1995).
32. Asangani, I. A. et al. Therapeutic targeting of BET bromodomain proteins in castration-resistant prostate cancer. *Nature* 510, 278-82 (2014).
33. Roche, P. J., Hoare, S. A. & Parker, M. G. A consensus DNA-binding site for the androgen receptor. *Mol Endocrinol* 6, 2229-35 (1992).
34. Pomerantz, M. M. et al. The androgen receptor cistrome is extensively reprogrammed in human prostate tumorigenesis. *Nat Genet* 47, 1346-51 (2015).
35. Cancer Genome Atlas Research, N. The Molecular Taxonomy of Primary Prostate Cancer. *Cell* 163, 1011-25 (2015).
36. Takayama, K. et al. Androgen-responsive long noncoding RNA CTBP1-AS promotes prostate cancer. *EMBO J* 32, 1665-80 (2013).
37. Consortium, G. T. Human genomics. The Genotype-Tissue Expression (GTEx) pilot analysis: multitissue gene regulation in humans. *Science* 348, 648-60 (2015).
38. Mele, M. et al. Human genomics. The human transcriptome across tissues and individuals. *Science* 348, 660-5 (2015).
39. Rhodes, D. R. et al. Oncomine 3.0: genes, pathways, and networks in a collection of 18,000 cancer gene expression profiles. *Neoplasia* 9, 166-80 (2007).
40. Engreitz, J. M. et al. RNA-RNA interactions enable specific targeting of noncoding RNAs to nascent Pre-mRNAs and chromatin sites. *Cell* 159, 188-99 (2014).
41. Kretz, M. et al. Control of somatic tissue differentiation by the long non-coding RNA TINCR. *Nature* 493, 231-5 (2013).
42. Gong, C. & Maquat, L. E. lncRNAs transactivate STAU1-mediated mRNA decay by duplexing with 3' UTRs via Alu elements. *Nature* 470, 284-8 (2011).
43. Wright, P. R. et al. CopraRNA and IntaRNA: predicting small RNA targets, networks and interaction domains. *Nucleic Acids Res* 42, W119-23 (2014).
44. Mann, M., Wright, P. R. & Backofen, R. IntaRNA 2.0: enhanced and customizable prediction of RNA-RNA interactions. *Nucleic Acids Res* 45, W435-W439 (2017).
45. Lennox, K. A. & Behlke, M. A. Cellular localization of long non-coding RNAs affects silencing by RNAi more than by antisense oligonucleotides. *Nucleic Acids Res* 44, 863-77 (2016).
46. Meng, L. et al. Towards a therapy for Angelman syndrome by targeting a long non-coding RNA. *Nature* 518, 409-12 (2015).
47. Wheeler, T. M. et al. Targeting nuclear RNA for in vivo correction of myotonic dystrophy. *Nature* 488, 111-5 (2012).
48. Hua, Y. et al. Antisense correction of SMN2 splicing in the CNS rescues necrosis in a type III SMA mouse model. *Genes Dev* 24, 1634-44 (2010).
49. Evers, M. M., Toonen, L. J. & van Roon-Mom, W. M. Antisense oligonucleotides in therapy for neurodegenerative disorders. *Adv Drug Deliv Rev* 87, 90-103 (2015).
50. Yeap, B. B. et al. Novel binding of HuR and poly(C)-binding protein to a conserved UC-rich motif within the 3'-untranslated region of the androgen receptor messenger RNA. *J Biol Chem* 277, 27183-92 (2002).
51. Lebedeva, S. et al. Transcriptome-wide analysis of regulatory interactions of the RNA-binding protein HuR. *Mol Cell* 43, 340-52 (2011).
52. Prensner, J. R. et al. Transcriptome sequencing across a prostate cancer cohort identifies PCAT-1, an unannotated lincRNA implicated in disease progression. Nat Biotechnol 29, 742-9 (2011).

53. Cieslik, M. et al. The use of exome capture RNA-seq for highly degraded RNA with application to clinical cancer sequencing. Genome Res 25, 1372-81 (2015).
54. Anders, S., Pyl, P. T. & Huber, W. HTSeq—a Python framework to work with high-throughput sequencing data. Bioinformatics 31, 166-9 (2015).
55. Liao, Y., Smyth, G. K. & Shi, W. featureCounts: an efficient general purpose program for assigning sequence reads to genomic features. Bioinformatics 30, 923-30 (2014).
56. Harrow, J. et al. GENCODE: the reference human genome annotation for The ENCODE Project. Genome Res 22, 1760-74 (2012).
57. Law, C. W., Chen, Y., Shi, W. & Smyth, G. K. voom: Precision weights unlock linear model analysis tools for RNA-seq read counts. Genome Biol 15, R29 (2014).
58. Ritchie, M. E. et al. limma powers differential expression analyses for RNA-sequencing and microarray studies. Nucleic Acids Res 43, e47 (2015).
59. Robinson, M. D., McCarthy, D. J. & Smyth, G. K. edgeR: a Bioconductor package for differential expression analysis of digital gene expression data. Bioinformatics 26, 139-40 (2010).
60. Cline, M. S. et al. Integration of biological networks and gene expression data using Cytoscape. Nat Protoc 2, 2366-82 (2007).
61. Zhang, Y. et al. Model-based analysis of ChIP-Seq (MACS). Genome Biol 9, R137 (2008).
62. Hansen, P. et al. Saturation analysis of ChIP-seq data for reproducible identification of binding peaks. Genome Res 25, 1391-400 (2015).
63. Kent, W. J., Zweig, A. S., Barber, G., Hinrichs, A. S. & Karolchik, D. BigWig and BigBed: enabling browsing of large distributed datasets. Bioinformatics 26, 2204-7 (2010).
64. Bailey, T. L. et al. MEME SUITE: tools for motif discovery and searching. Nucleic Acids Res 37, W202-8 (2009).
65. Mehra, R. et al. A novel RNA in situ hybridization assay for the long noncoding RNA SChLAP1 predicts poor clinical outcome after radical prostatectomy in clinically localized prostate cancer. Neoplasia 16, 1121-7 (2014).
66. Newton, M. A., Quintana, F. A., Den Boon, J. A., Sengupta, S. & Ahlquist, P. Random-Set Methods Identify Distinct Aspects of the Enrichment Signal in Gene-Set Analysis. Annals of Applied Statistics 1, 85-106 (2007).
67. Raj, A., van den Bogaard, P., Rifkin, S. A., van Oudenaarden, A. & Tyagi, S. Imaging individual mRNA molecules using multiple singly labeled probes. Nat Methods 5, 877-9 (2008).
68. Niknafs, Y. S. et al. The lncRNA landscape of breast cancer reveals a role for DSCAM-AS1 in breast cancer progression. Nat Commun 7, 12791 (2016).
69. Rossiello, F. et al. DNA damage response inhibition at dysfunctional telomeres by modulation of telomeric DNA damage response RNAs. Nat Commun 8, 13980 (2017).
70. Paulsen, M. T. et al. Coordinated regulation of synthesis and stability of RNA during the acute TNF-induced proinflammatory response. Proc Natl Acad Sci USA 110, 2240-5 (2013).
71. Paulsen, M. T. et al. Use of Bru-Seq and BruChase-Seq for genome-wide assessment of the synthesis and stability of RNA. Methods 67, 45-54 (2014).

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of treating cancer, comprising: administering an agent that blocks the expression or activity of ARlnc1 to a subject diagnosed with cancer under conditions such that a sign or symptom of said cancer is reduced, wherein said agent comprises a nucleic acid.

2. The method of claim 1, wherein said nucleic acid is selected from the group consisting of a siRNA, a shRNA, a miRNA, and an antisense oligonucleotide.

3. The method of claim 1, wherein said cancer is prostate cancer.

4. The method of claim 1, wherein said cancer expresses ARlnc1.

5. The method of claim 4, wherein ARlnc1 is overexpressed in said cancer relative to the level of expression in non-cancerous cells.

6. The method of claim 1, wherein said method further comprises the step of assaying a sample of said cancer for the level of expression of ARlnc1.

7. A method, comprising:
a) assaying a sample from a subject diagnosed with cancer, wherein said sample comprises cancer tissue or cells for the level of expression of ARlnc1; and
b) administering an agent that blocks the expression or activity of ARlnc1 when expression of ARlnc1 is present in said sample, wherein said agent comprises a nucleic acid.

8. The method of claim 7, wherein said nucleic acid is selected from the group consisting of a siRNA, a shRNA, a miRNA, and an antisense oligonucleotide.

9. The method of claim 7, wherein said cancer is prostate cancer.

* * * * *